United States Patent
Peters-Wendisch et al.

(10) Patent No.: US 11,312,981 B2
(45) Date of Patent: Apr. 26, 2022

(54) CAROTENOID AND AMINO ACID BIOSYNTHESIS USING RECOMBINANT CORYNEBACTERIUM GLUTAMICUM

(71) Applicant: UNIVERSITÄT BIELEFELD, Bielefeld (DE)

(72) Inventors: Petra Peters-Wendisch, Bielefeld (DE); Volker Wendisch, Bielefeld (DE); Nadja Alina Henke, Spenge (DE)

(73) Assignee: UNIVERSITÄT BIELEFELD, Bielefeld (DE)

(*) Notice: Subject to any disclaimer, the term of this patent is extended or adjusted under 35 U.S.C. 154(b) by 0 days.

(21) Appl. No.: 16/608,570

(22) PCT Filed: Apr. 26, 2018

(86) PCT No.: PCT/EP2018/060711
§ 371 (c)(1),
(2) Date: Oct. 25, 2019

(87) PCT Pub. No.: WO2018/197608
PCT Pub. Date: Nov. 1, 2018

(65) Prior Publication Data
US 2020/0181660 A1 Jun. 11, 2020

(30) Foreign Application Priority Data
Apr. 27, 2017 (EP) .................... 17168331

(51) Int. Cl.
*C12P 13/08* (2006.01)
*C12P 23/00* (2006.01)
*C12N 1/20* (2006.01)
*C12R 1/15* (2006.01)

(52) U.S. Cl.
CPC ............. *C12P 13/08* (2013.01); *C12P 23/00* (2013.01); *C12N 1/205* (2021.05); *C12R 2001/15* (2021.05); *C12Y 114/11* (2013.01)

(58) Field of Classification Search
CPC . C12P 13/08; C12P 23/00; C12R 1/15; C12Y 114/11; C12Y 114/13129; C12N 9/0071; C12N 9/0073; C07K 14/34
See application file for complete search history.

(56) References Cited

U.S. PATENT DOCUMENTS

2009/0221027 A1  9/2009  Zelder et al.

FOREIGN PATENT DOCUMENTS

WO  2007141111 A2  12/2007

OTHER PUBLICATIONS

Henke et al., Frontiers in Microbiology 8(633):1-15, Apr. 24, 2017.*
Sousa et al., Microbiology 148(Pt5):1291-1303, 2002.*
Anda et al., GenBank accession No. BAT30872, Dec. 3, 2015.*
Anda et al., GenBank accession No. BAT30875, Dec. 3, 2015.*
Anda et al., GenBank accession No. LC066395, Dec. 3, 2015.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Kalinowski et al., Genetic and biochemical analysis of the aspartokinase from Corynebacterium glutamicum. Mol Microbiol. May 1991;5(5):1197-1204.
Kalinowski et al., The complete Corynebacterium glutamicum ATCC 13032 genome sequence and its impact on the production of L-aspartate-derived amino acids and vitamins. J Biotechnol. Sep. 4, 2003;104(1-3):5-25.
Kholy et al., Glutamate Dehydrogenase Is Not Essential for Glutamate Formation by Corynebacterium glutamicum. Appl Environ Microbiol. Jul. 1993;59(7):2329-2331.
Kim and Keasling, Metabolic Engineering of the Nonmevalonate Isopentenyl Diphosphate Synthesis Pathway in *Escherichia coli* Enhances Lycopene Production. Biotechnol Bioeng. Feb. 20, 2001;72(4):408-415.
Kinoshita et al., L-Lysine Production Using Auxotroph (Preliminary report). 1958;4(2):128-129.
Kinoshita et al., Studies on the Amino Acid Fermentation; Part I. Production of L-Glutamic Acid by Various Microorganisms. J Gen Appl Microbiol. 1957;3(3):193-205.
Kinoshita et al., Taxonomical Study of Glutamic Acid Accumulating Bacteria, *Micrococcus glutamicus* nov. sp. Bull Agricul Chem Soc Japan, 1958;22(3):176-185 doi: 10.1080/03758397.1958.10857463.
Kirby and Keasling, Biosynthesis of Plant Isoprenoids: Perspectives for Microbial Engineering. Annu Rev Plant Biol, 2009;60:335-355.
Kircher and Pfefferle, The fermentative production of L-lysine as an animal feed additive. Chemosphere. Apr. 2001;43(1):27-31.
Koller et al., Microalgae as versatile cellular factories for valued products. Algal Research, 2014;6A:52-63.
Krubasik et al., Detailed biosynthetic pathway to decaprenoxanthin diglucoside in Corynebacterium glutamicum and identification of novel intermediates. Arch Microbiol. Sep. 2001;176(3):217-223.
Krubasik et al., Expression and functional analysis of a gene cluster involved in the synthesis of decaprenoxanthin reveals the mechanisms for C50 carotenoid formation. Eur J Biochem. Jul. 2001;268(13):3702-3708.

(Continued)

*Primary Examiner* — Delia M Ramirez

(74) *Attorney, Agent, or Firm* — Acuity Law Group, PC; Michael A. Whittaker

(57) ABSTRACT

The present invention provides a method of producing astaxanthin and lysine in recombinant gram-positive bacteria comprising a nucleic acid sequence encoding for a crtZ-protein from *F. pelagi* and comprises a nucleic acid sequence encoding for a crtW-protein.

13 Claims, 10 Drawing Sheets

Figure 1:
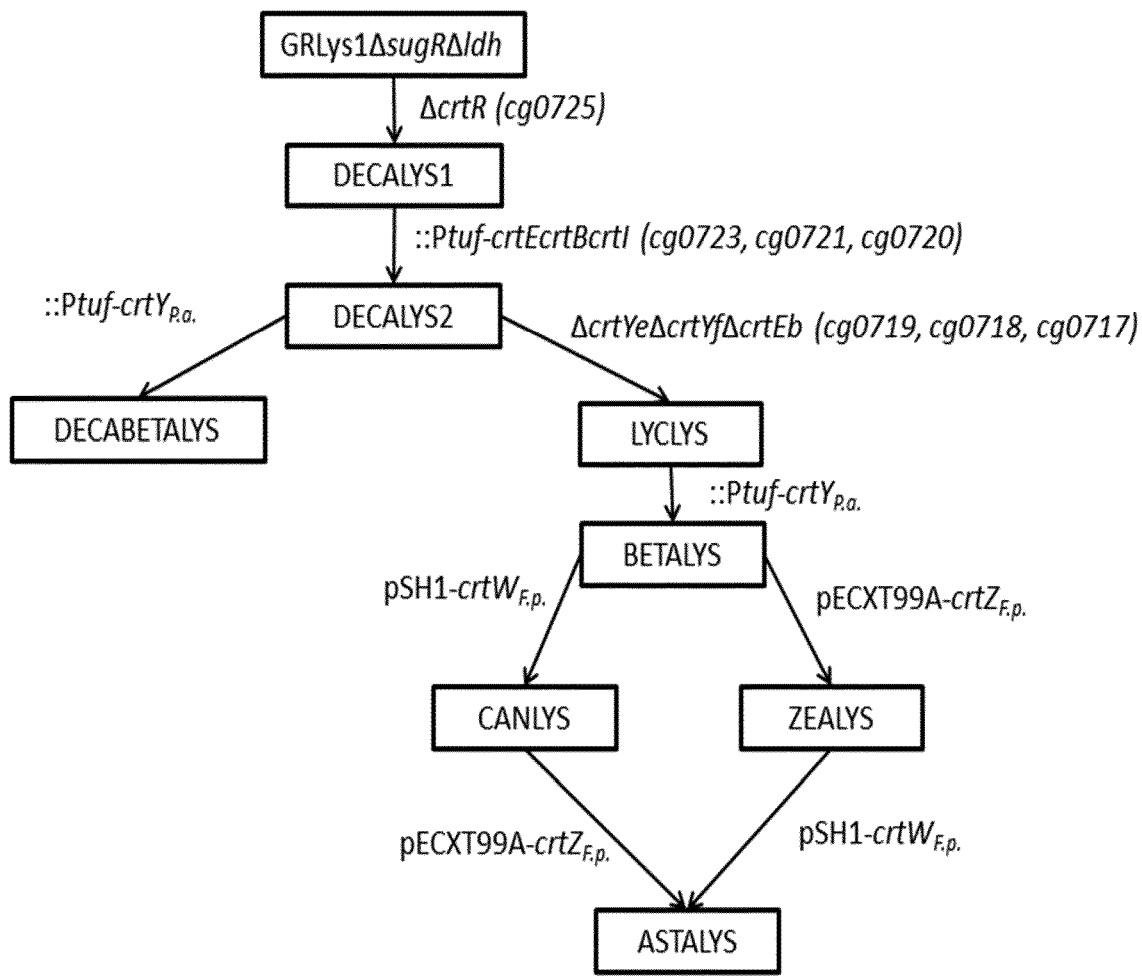

Specification includes a Sequence Listing.

(56) References Cited

OTHER PUBLICATIONS

Kurihara, Glutamate: From discovery as a food flavor to role as a basic taste (umami). Am J Clin Nutr. Sep. 2009;90(3):719S-722S.
Leuchtenberger et al., Biotechnological production of amino acids and derivatives: Current status and prospects. Appl Microbiol Biotechnol. Nov. 2005;69(1):1-8.
Li et al., An economic assessment of astaxanthin production by large scale cultivation of Haematococcus pluvialis. Biotechnol Adv. Nov.-Dec. 2011;29(6):568-574.
Liebl, Corynebacterium Taxonomy. in Eggeling, L. and Bott, M. (eds) Handbook of Corynebacterium glutamicum. Boca Raton, FL: CRC Press, 2005:9-34.
Lorenz and Cysewski, Commercial potential for Haematococcus microalgae as a natural souice of astaxanthin. Trends Biotechnol. Apr. 2000;18(4):160-167.
Lotan and Hirschberg, Cloning and expression in *Escherichia coli* of the gene encoding β-C-4-oxygenase, that converts β-carotene to the ketocarotenoid canthaxanthin in Haematococcus pluvialis. FEBS Lett. 1995;364(2):125-128.
Malin and Bourd, Phosphotransferase-dependent glucose transport in Corynebacterium glutamicum. J Appl Bacteriol. Dec. 1991,71(6):517-523.
Mat-Jan et al., Mutants of *Escherichia coli* Deficient in the Fermentative Lactate Dehydrogenase. J Bacteriol. Jan. 1989;171(1):342-348.
Meiswinkel et al., Crude glycerol-based production of amino acids and putrescine by Corynebacterium glutamicum. Bioresour Technol. Oct. 2013;145:254-258.
Meldrum, Glutamate as a Neurotransmitter in the Brain: Review of Physiology and Pathology. J Nutr. Apr. 2000;130 (4S Suppl):1007S-1015S.
Mimitsuka et al., Metabolic Engineering of Corynebacterium glutamicum for Cadaverine Fermentation. Biosci Biotechnol Biochem. Sep. 2007;71(9):2130-2135.
Misawa et al., Canthaxanthin Biosynthesis by the Conversion of Methylene to Keto Groups in a Hydrocarbon β-Carotene by a Single Gene. Biochem Biophys Res Commun. Apr. 26, 1995;209(3):867-876.
Misawa et al., Structure and Functional Analysis of a Marine Bacterial Carotenoid Biosynthesis Gene Cluster and Astaxanthin Biosynthetic Pathway Proposed at the Gene Level. J Bacteriol. Nov. 1995;177(22):6575-6584.
Mortensen and Skibsted, Importance of Carotenoid Structure in Radical-Scavenging Reactions. J Agric Food Chem. 1997;45(8):2970-2977.
Mortensen et al., Comparative mechanisms and rates of free radical scavenging by carotenoid antioxidants. FEBS Lett. Nov. 24, 1997;418(1-2):91-97.
Mueller and Huebner, Economic Aspects of Amino Acids Production. Adv Biochem Eng Biotechnol. 2003;79:137-170.
Nakayama et al., Studies on Lysine Fermentation I. the Control Mechanism on Lysine Accumulation By Homoserine and Threonine. J Gen Appl Microbiol. 1961;7(3):145-154.
Norris et al., Genetic Dissection of Camtenoid Synthesis in *Arabidopsis* Defines Plastoquinone as an Essential Component of Phytoene Desat urat ion. Plant Cell. Dec. 1995:2139-2149.
Olaizola and Huntley, Recent Advances in Commercial Production of Astaxanthin from Microalgae. In book Recent Advances in Marine Biotechnology. vol. 9. Biomaterials and Bioprocessing (pp. 143-164).
Osborne and Mendel, Amino-Acids in Nutrition and Growth. J Biol Chem. 1914;17:325-349.
Ovie and Eze, Lysine Requirement and its Effect on the Body Composition of Oreochromis niloticous Fingerlings. J Fisheries Aquatic Sci. 2013;8(1)94-100.
Pérez-García et al., Engineering Corynebacterium glutamicum for fast production of L-lysine and L-pipecolic acid. Appl Microbiol Biotechnol. Sep. 2016;100(18):8075-8090.
Peters-Wendisch et al., Engineering biotin prototrophic Corynebacterium glutamicum strains for amino acid, diamine and carotenoid production. J Biotechnol. Dec. 20, 2014;192 Pt B:346-354.
Pfefferle et al., Biotechnological Manufacture of Lysine. Adv Biochem Eng Biotechnol. 2003;79:59-112.
Pfeifer et al., Silencing of cryptic prophages in Corynebacterium glutamicum. Nucleic Acids Res. Dec. 1, 2016;44(21):10117-10131.
Porter and Anderson, The biosynthesis of carotenes. Arch Biochem Biophys. Jun. 1962;97:520-528.
Radmacher et al., Ethambutol, a cell wall inhibitor of Mycobacterium tuberculosis, elicits L-glutamate efflux of Corynebacterium glutamicum. Microbiology (Reading). May 2005;151(Pt 5):1359-1368.
Reardon and Abeles, Mechanism of Action of isopentenyl Pyrophosphate Isomerase: Evidence for a Carbonium on Intermediate. Biochemistry. Sep. 23, 1986;25(19):5609-5616.
Rodríguez-Concepción and Boronat, Elucidation of the Methylerythritol Phosphate Pathway for Isoprenoid Biosynthesis in Bacteria and Plastids. A Metabolic Milestone Achieved through Genomics. Plant Physiol. Nov. 2002;130(3):1079-1089.
Rodriguez-Saiz et al., Xanthophyllomyces dendrorhous for the industrial production of astaxanthin. Appl Microbiol Biotechnol. Oct. 2010;88(3):645-658.
Ronen et al., Regulation of carotenoid biosynthesis during tomato fruit development: expression of the gene for lycopene epsilon cyclase is down- regulated during ripening and is elevated in the mutant Delta. Plant J. Feb. 1999;17(4):341-351.
Sakai et al., Effect of Lignocellulose-Derived Inhibitors on Growth of and Ethanol Production by Growth-Arrested Corynebacterium glutamicum R. Appl Environ Microbiol. Apr. 2007;73(7):2349-2353.
Sandmann and Yukawa, Vitamin Synthesis: Carotenoids, Biotin and Pantothenate. In Handbook of Corynebacterium glutamicum. by Eggeling, and Bott, (eds) CRC express journal. Boca Raton, FL: CRC Press, 2005, pp. 399-417.
Schäfer et al., Small mobilizable multi-purpose cloning vectors derived from the *Escherichia coli* plasmids pK18 and pK19: selection of defined deletions in the chromosome of Corynebacterium glutamicum. Gene. Jul. 22, 1994;145(1):69-73.
Schneider and Wendisch, Putrescine production by engineered Corynebacterium glutamicum. Appl Microbiol Biotechnol. Oct. 2010;88(4):859-868.
Schneider et al., Production of the amino acids L-glutamate, L-lysine, L-omithine and L-arginine from arabinose by recombinant Corynebacterium glutamicum. J Biotechnol. Jul. 10, 2011;154(2-3):191-198.
Schrumpf et al., Isolation and prominent characteristics of an L-lysine hyperproducing strain of Corynebacterium glutamicum. Appl Microbiol Biotechnol. Aug. 1992;37(5):566-571.
Seibold et al., Roles of maltodextrin and glycogen phosphorylases in maltose utilization and glycogen metabolism in Corynebacterium glutamicum. Microbiology (Reading). Feb. 2009;155(Pt 2):347-358.
Abbes et al., Biological properties of carotenoids extracted from Halobacterium halobium isolated from a Tunisian solar saltem. BMC Complement Altern Med. Oct. 4, 2013;13:255.
Agranoff et al., Isopentenol pyrophsophate isomerase. J Amer Chem Soc. 1959;81(5):1254-1255.
Ajinomoto Co. (2015) Analysts' Meeting for FY2015 Consolidated Results. Available at: http://www.ajinomoto.com/en/ir/ir_library/meeting_qa_2015.html (Accessed: Nov. 8, 2016:4 pages).
Ajinomoto Co. (2016a) Food Products Business. Available at: www.ajinomoto.com/en/ir/pdf/Food-Oct2016.pdf. (Oct. 2016:17 pages).
Ajinomoto Co. (2016b) Life Support Business. Available at: http://www.ajinomoto.com/en/ir/pdf/Life_Support-Oct2016.pdf. (Oct. 2016:6 pages).
Armstrong, Eubacteria Show Their True Colors: Genetics of Carotenoid Pigment Biosynthesis from Microbes to Plants. J Bacteriol. Aug. 1994;176(16):4795-4802.
Asai et al., On L-Glutamic Acid Fermentation. Bull Agr Chem Soc Japan. 1957;21(2):134-135.
Baumgart et al., Construction of a Prophage-Free Variant of Corynebacterium glutamicum ATCC 13032 for Use as a Platform

(56) References Cited

OTHER PUBLICATIONS

Strain for Basic Research and Industrial Biotechnology. Appl Environ Microbiol. Oct. 2013;79(19):6006-6015.

BCC Research, The Global Market for Carotenoids—FOD025E. Available at: http://www.bccresearch.com/market-research/food-and-beverage/carotenoids-global-market-report-fod025e.html. Report Overview and Table of Contents only (Jul. 2015:9 pages).

Bhosale and Bernstein, Microbial xanthophylls. Appl Microbiol Biotechnol. Sep. 2005;68(4):445-455.

Biswal, Oxidative stress and astaxanthin: The novel supernutrient carotenoid. Int J Health Allied Sci.2014;3(3):147-153.

Bjerkeng, Carotenoid pigmentation of salmonid fishes—recent progress. In: Cruz-Suárez et al., (Eds.). Avances en Nutrición Acuícola V. Memorias del V Simposium Internacional de Nutrición Acuícola. , Mérida, Yucatán Nov. 19-22, 2000:71-89.

Blombach and Eikmanns, Current knowledge on isobutanol production with *Escherichia coli*, Bacillus subtilis and Corynebacterium glutamicum. Bioeng Bugs. Nov.-Dec. 2011;2(6):346-350.

Blombach and Seibold, Carbohydrate metabolism in Corynebacterium glutamicum and applications for the metabolic engineering of l-lysine production strains. Appl Microbiol Biotechnol. May 2010;86(5):1313-1322.

Bunch et al., The IdhA gene encoding the fermentative lactate dehydrogenase of *Escherichia coli*. Microbiology (Reading). Jan. 1997;143 ( Pt 1 ):187-195.

Burton and Ingold, β-Carotene: An Unusual Type of Lipid Antioxidant. Science. May 11, 1984;224(4649):569-573.

Byrne, 2014 Global BioChem to put the brakes on lysine production. Available at: http://www.feednavigator.com/Suppliers/Global-BioChem-to-put-the-brakes-on-lysine-production (Accessed: Oct. 28, 2016):3 pages.

Choi et al., Characterization of bacterial β-carotene 3,3'-hydroxylases, CrtZ, and P450 in astaxanthin biosynthetic pathway and adonirubin production by gene combination in *Escherichia coli*. Appl Microbiol Biotechnol. Oct. 2006;72(6):1238-1246.

Choi et al., Characterization of two β-carotene ketolases, CrtO and CrtW, by complementation analysis in *Escherichia coli*. Appl Microbiol Biotechnol. Jul. 2007;75(6):1335-1341.

Coryneregnet, Gene: cg2672. Accessed online at: http://coryneregnet.compbio.sdu.dk/v6e/CoryneRegNet/queryElement.php?operon=OP_cg2672 (Accessed: Nov. 6, 2016:3 pages).

Cremer et al., Control of the Lysine Biosynthesis Sequence in Corynebacterium glutamicum as Analyzed by Overexpression of the Individual Corresponding Genes. Appl Environ Microbiol. Jun. 1991;57(6):1746-1752.

Cunningham and Gantt, Genes and Enzymes of Carotenoid Biosynthesis in Plants. Annu Rev Plant Physiol Plant Mol Biol. Jun. 1998;49:557-583.

Cunningham et al., Functional analysis of the beta and epsilon lycopene cyclase enzymes of *Arabidopsis* reveals a mechanism for control of cyclic carotenoid formation. Plant Cell. Sep. 1996;8(9):1613-1626.

Cutzu et al., From crude glycerol to carotenoids by using a Rhodotorula glutinis mutant. World J Microbiol Biotechnol. Jun. 2013;29(6):1009-1017.

Das et al., An update on microbial carotenoid production: application of recent metabolic engineering tools. Appl Microbiol Biotechnol. Dec. 2007;77(3):505-512.

de la Fuente et al., High-titer production of astaxanthin by the semi-industrial fermentation of Xanthophyllomyces dendrorhous. J Biotechnol. Jul. 20, 2010;148(2-3):144-146.

Eggeling and Sahm, L-Glutamate and L-lysine: traditional products with impetuous developments. Appl Microbiol Biotechnol. 1999;52(2):146-153.

Eikmanns et al., Amplification of three threonine biosynthesis genes in Corynebacterium glutamicum and its influence on carbon flux in different strains. Appl Microbiol Biotechnol. Feb. 1991;34(5):617-622.

Engels and Wendisch, The DeoR-Type Regulator SugR Represses Expression of ptsG in Corynebacterium glutamicum. J Bacteriol. Apr. 2007;189(8):2955-2966.

Gassel et al., Multiple improvement of astaxanthin biosynthesis in Xanthophyllomyces dendrorhous by a combination of conventional mutagenesis and metabolic pathway engineering. Biotechnol Lett. Apr. 2013;35(4):565-569.

Georgi et al., Lysine and glutamate production by Corynebacterium glutamicum on glucose, fructose and sucrose; Roles of malic enzyme and fructose-1,6-bisphosphatase. Metab Eng. Jul. 2005;7(4):291-301.

Giacometti, Free and Bound Glutamate in Natural Products. Glutamic Acid: Advances in biochemistry and physiology, 1979:25-34.

Goldstein and Brown, Regulation of the mevalonate pathway. Nature. Feb. 1, 1990;343(6257):425-430.

Goodwin et al., Biosynthesis of Carotenoids, in The Biochemistry of the Carotenoids: vol. 1 Plants. 2nd edn, 1980;33-76.

Goodwin et al., Nature and Properties, in The Biochemistry of the Carotenoids: vol. 1 Plants. II. 1980;1-32. doi: 10.1007/978-94-009-5860-9.

Gopinath et al., Amino acid production from rice straw and wheat bran hydrolysates by recombinant pentose-utilizing Corynebacterium glutamicum. Appl Microbiol Biotechnol. Dec. 2011;92(5):985-996.

Grand View Research (2015) Global Amino Acids Market by Product (L-Glutamate, Lysine, Methionine, Threonine, Tryptophan, Leucine, Iso-Leucine, Valine, Glutamine, Arginine), By Source, By Application Expected to Reach USD 35.40 Billion By 2022. Available at: https://www.grandviewresearch.com/press-release/global-amino-acids-market (Accessed: Oct. 26, 2016:3 pages).

Guerin et al., Haematococcus astaxanthin: Applications for human health and nutrition. Trends Biotechnol. May 2003;21(5):210-216.

Han, Monosodium Glutamate as a Chemical Condiment. Ind Eng Chem. Oct. 1929;21(10):984-987.

Harker and Bramley, Expression of prokaryotic 1-deoxy-D-xylulose-5-phosphatases in *Escherichia coli* increases carotenoid and ubiquinone biosynthesis. FEBS Lett. Apr. 1, 1999;448(1): 115-119.

Heider et al., Production and glucosylation of C50 and C40 carotenoids by metabolically engineered Corynebacterium glutamicum. Appl Microbiol Biotechnol. Feb. 2014;98(3):1223-1235.

Heider et al.., Optimization of the IPP precursor supply for the production of lycopene, decaprenoxanthin and astaxanthin by Corynebacterium glutamicum. Front Bioeng Biotechnol. Aug. 20, 2014;2:28.

Henke et al., Production of the Marine Carotenoid Astaxanthin by Metabolically Engineered Corynebacterium glutamicum. Mar Drugs. Jun. 30, 2016;14(7):124.

Holm and Sander, Dali: a network tool for protein structure comparison. Trends Biochem Sci. Nov. 1995;20(11):478-480.

Holm and Sander, Protein Structure Comparison by Alignment of Distance Matrices. J Mol Biol. Sep. 5, 1993;233(1):123-138.

Holm and Sander, Touring protein fold space with Dali/FSSP. Nucleic Acids Res. Jan. 1, 1998;26(1):316-9.

Hunter, The Non-mevalonate Pathway of Isoprenoid Precursor Biosynthesis. J Biol Chem. Jul. 27, 2007;282(30):21573-21577.

Inui et al., Metabolic Analysis of Corynebacterium glutamicum during Lactate and Succinate Productions under Oxygen Deprivation Conditions. J Mol Microbiol Biotechnol. 2004;7(4):182-196.

Jager et al., Expression of the Bacillus subtilis sacB gene leads to sucrose sensitivity in the gram-positive bacterium Corynebacterium glutamicum but not in Streptomyces lividans. J Bacteriol. Aug. 1992;174(16):5462-5465.

Kajiwara et al., Isolation and functional identification of a novel cDNA for astaxanthin biosynthesis from Haematococcus pluvialis, and astaxanthin synthesis in *Escherichia coli*. Plant Mol Biol. Oct. 1995;29(2):343-352.

Seibold et al., Utilization of soluble starch by a recombinant Corynebacterium glutamicum strain: Growth and lysine production. J Biotechnol. Jul. 13, 2006;124(2):381-391.

Shiio et al., Effect of Biotin on the Bacterial Formation of Glutamic Acid I. Glutamate Formation and Cellular Permeability of Amino Acids. J Biochem. Jan. 1962;51:56-62.

(56) References Cited

OTHER PUBLICATIONS

Simon et al., A Broad Host Range Mobilization System for In Vivo Genetic Engineering: Transposon Mutagenesis in Gram Negative Bacteria. Biotechnol, 1983; 1:784-789.

Song et al., Single-step production of polyhydroxybutyrate from starch by using α-amylase cell-surface displaying system of Corynebacterium glutamicum. J Biosci Bioeng. Jan. 2013;115(1):12-14.

Spektrum—Lexikon der Biochemie (1999) Astaxanthin. Available at: http://www.spektrum.de/lexikon/biochemie/astaxanthin/609 (Accessed: Oct. 18, 2016).

Spektrum—Lexikon der Biologie (1999a) Astaxanthin. Available at: http://www.spektrum.de/lexikon/biologie/astaxanthin/5587 (Accessed: Oct. 18, 2016).

Spektrum—Lexikon der Biologie (1999b) Lysin. Available at: http://www.spektrum.de/lexikon/biologie/lysin/40375 (Accessed: Oct. 31, 2016).

Spektrum—Lexikon der Biologie (1999c) Minimumgesetz. Available at: http://www.spektrum.de/lexikon/biologie/minimumgesetz/43184 (Accessed: Nov. 7, 2016).

Spektrum—Lexikon der Chemie (1998) Lysin. Available at: http://www.spektrum.de/lexikon/chemie/I-lysin/5499 (Accessed: Oct. 31, 2016).

Thompson et al., Clustal W: improving the sensitivity of progressive multiple sequence alignment through sequence weighting, position-specific gap penalties and weight matrix choice. Nucleic Acids Res. Nov. 11, 1994;22(22):4673-4680.

Thulasiram et al., Chimeras of Two Isoprenoid Synthases in Isoprenoid Biosynthesis. Science. Apr. 6, 2007;316(5821):73-76.

Tobias and Arnold, Biosynthesis of novel carotenoid families based on unnatural carbon backbones: A model for diversification of natural product pathways. Biochim Biophys Acta. Feb. 2006;1761(2):235-246 doi: 10.1016/j.bbalip.2006.01.003.

Tsuchidate et al., Glutamate production from β-glucan using endoglucanase-secreting Corynebacterium glutamicum. Appl Microbiol Biotechnol. May 2011;90(3):895-901.

Uhde et al., Glucosamine as carbon source for amino acid-producing Corynebacterium glutamicum. Appl Microbiol Biotechnol. Feb. 2013;97(4):1679-1687.

Unthan et al., Chassis organism from Corynebacterium glutamicum—a top-down approach to identify and delete irrelevant gene clusters. Biotechnol J. Feb. 2015;10(2):290-301.

Vershinin, Biological functions of carotenoids—diversity and evolution. Biofactors. 1999;10(2-3):99-104.

Wendisch et al., Updates on industrial production of amino acids using Corynebacterium glutamicum. World J Microbiol Biotechnol. Jun. 2016;32(6):105.

Wisniewska and Subczynski, Effects of polar carotenoids on the shape of the hydrophobic barrier of phospholipid bilayers. Biochim Biophys Acta. Jan. 19, 1998;1368(2):235-246.

Wu, Amino acids: Metabolism, functions, and nutrition. Amino Acids. May 2009;37(1):1-17.

Yokota and Lindley, Central Metabolism: Sugar Uptake and Conversion, in Eggeling, L. and Bott, M. (eds) Handbook of Corynebacterium glutamicum. Boca Raton, FL: CRC Press, 2005 pp. 215-240.

Zelcbuch et al., Spanning high-dimensional expression space using ribosome-binding site combinatorics. Nucleic Acids Res. May 2013;41(9):e98 (8 pages total).

International Search Report dated Jul. 3, 2018 in PCT/EP2018/060711 (7 pages).

Written Opinion dated Jul. 3, 2018 in PCT/EP2018/060711 (9 pages).

Nadja et al., "Production of the Marine Carotenoid Astaxanthin by Metabolically Engineered Corynebacterium glutamicum", Mar. Drugs, 2016, 14, 124; doi:10.3390/md14070124.

* cited by examiner a) DECA LYS1 b) DECA LYS1 c) DECA LYS2 d) DECA LYS2 e) DECA BETA LYS f) LYC LYS g) BETA LYS h) BETA LYS i) CAN LYS j) ZEA LYS k) ASTA LYS

CAROTENOID AND AMINO ACID BIOSYNTHESIS USING RECOMBINANT CORYNEBACTERIUM GLUTAMICUM

CROSS-REFERENCE TO RELATED APPLICATIONS

The present invention is filed under 35 U.S.C. § 371 as the U.S. national phase of International Application No. PCT/EP2018/060711, filed Apr. 26, 2018, which designated the U.S. and claims the right of priority of European patent application No. 17168331.1, filed with the European Patent Office on Apr. 27, 2017. The entire disclosures of the above-identified priority applications are hereby fully incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 25, 2019, is named SCH-5300-US_SeqListing.txt and is 101 kilobytes in size.

BACKGROUND

Carotenoids are natural pigments that can be ubiquitously found in plants, algae, fungi and bacteria. These pigments form a subfamily of the large and diverse group of terpenoids. Carotenoids can be categorized according to the length of their carbon backbone. Most carotenoids possess a C40 backbone but C30 and C50 carotenoids also occur.

Carotenoids become more important for the health industry due to their beneficial effects on health and their possible pharmaceutical, medical and nutraceutical applications (Belviranli and Okudan, 2015, Antioxidants in Sport Nutrition, M. Lamprecht, Boca Raton Fla., by Taylor & Francis Group, LLC). These days, carotenoids are especially used as food and beverage colorants, animal feed and nutraceuticals.

Although the chemical synthesis of astaxanthin from petrochemical precursors is so far more cost-efficient and more dominant on the market (Li, Zhu et al. 2011, *Biotechnol. Adv.* 29 (6), 568-574), the demand for naturally produced carotenoids is increasing. The synthetic astaxanthin is a mixture of R- and S-enantiomers, which is significantly inferior to natural-based astaxanthin and thus might not be suitable as a nutraceutical supplement without further complex and cost-intensive purification steps before application. Consequently, the demand for an efficient and environmentally friendly production of natural astaxanthin, and carotenoids in general, by microbial hosts is increasing (Cutzu, Coi et al. 2013, World J Microbiol Biotechnol, 77 (3), 505-512). The green freshwater microalgae *Haematococcus pluvialis* and the red yeast *Pfaffia rhodozyma* are established hosts for a commercial production of astaxanthin (Rodriguez-Saiz, de la Fuente et al. 2010, Appl Microbiol Biotechnol, 88 (3), 645-658) but it can also be produced by other microalgae and marine bacteria. The highest production titer of 9.7 mg/g CDW was achieved by a metabolically engineered *P. rhodozyma* strain (Gassel, Schewe et al. 2013, Biotechnology Letters, 35 (4), 565-569), while the highest titer of 5.8 mg/g CDW was produced by a recombinant *E. coli* strain for which a combinatorial approach was used (Zelcbuch, Antonovsky et al. 2013, Nucleic Acids Res, 41 (9), e98).

Carotenoids, like all terpenoids, derive from the C5 precursor isopentenyl pyrophosphate (IPP) and its isomer dimethylallyl pyrophosphate (DMAPP). IPP is synthesized either by the mevalonic acid (MVA) pathway or the methylerythritol phosphate (MEP) pathway, also known as Sahm-Rohmer pathway or non-mevalonate pathway (Rodriguez-Concepcion and Boronat 2002, Plant Physiol. 130(3):1079-1089). The MVA-pathway is mainly present in eukaryotes, archaea and a small number of bacteria. In the MVA-pathway IPP is synthesized from the primary educt acetyl-CoA via the intermediate mevalonate. In the alternative MEP-pathway, found in most bacteria as well as in plant plastids, IPP is synthesized from pyruvate and glyceraldehyde 3-phosphate (GAP) via the intermediate methylerythritol 4-phosphate (Kirby and Keasling 2009, Annu Ref Plant Biol. 60: 335-355). The MEP-pathway consists of nine enzymatic steps depending on eight enzymes (Hunter, 2007, J Biol Chem, 282 (30), 21573-21577) (FIG. 1a). The initial condensation of pyruvate and glyceraldehyde 3-phosphate is catalyzed by thiamine pyrophosphate-dependent 1-deoxy-D-xylulose 5-phosphate synthase [EC2.2.1.7] encoded by dxs-nucleic acid sequence leading to 1-deoxy-d-xylulose-5-phospate (DXP). Subsequently DXP is converted to MEP by DXP-reductoisomerase [EC1.1.1.267] encoded by dxp-nucleic acid sequence. MEP is transformed to 2-C-methyl-d-erythritol-2,4-cyclodiphosphate (ME-cPP) through three enzymatic steps catalyzed by 2-C-methylerythritol 4-phosphate cytidylyltransferase (IspD) encoded by ispD-nucleic acid sequence, 2-C-methylerythritol 4-diphosphocytidyl kinase (IspE) encoded by ispE-nucleic acid sequence and 2-C-methylerythritol 2,4-cyclodiphosphate synthases (IspF) encoded by ispF-nucleic acid sequence using CTP and ATP as cofactors. 4-Hydroxy-3-methyl-2-(E)-butenyl-4-diphosphate synthase IspG encoded by ispG-nucleic acid sequence catalyzes the conversion of ME-cPP to 4-hydroxy-3-methyl-2-(E)-butenyl-4-diphosphate (HMBPP). Finally, HMBPP can be reduced to IPP or DMAPP by 4-Hydroxy-3-methyl-2-(E)-butenyl-4-diphosphate reductase IspH encoded by ispH-sequence. IPP and DMAPP can be isomerized by isopentenyl diphosphate isomerase Idi encoded by idi. The C5 compounds IPP and DMAPP can be condensed by several chain elongation reactions catalyzed by prenyltransferases. The first condensation reaction results in the C10 compound geranyl diphosphate (GPP), the precursor of monoterpenes. The C15 compound farnesyl diphosphate (FPP) represents the precursor of sesquiterpenes and C30 carotenoids. All C40 and C50 carotenoids are derived from the C20 compound geranylgeranyl disphosphate (GGPP) synthesized from one molecule of DMAPP and three molecules of IPP by GGPP synthase. Lycopene can be converted to β-carotene by a lycopene cyclase (CrtY) [EC5.5.1.19]. β-carotene can be further functionalized to astaxanthin by hydroxylation and oxygenation. The 4,4"-beta-ionone ring ketolase [EC1.14.11.B16], encoded by crtW-nucleic acid sequence, and the 3,3"-beta-ionone ring hydroxylase [EC1.14.13.129], encoded by crtZ-nucleic acid sequence, are the most common enzymes responsible for astaxanthin synthesis.

*Corynebacterium glutamicum* is a Gram-positive soil bacterium. It belongs to the Corynebacterineae within the order Actinomycetales and the class of Actinobacteria. *C. glutamicum* was used in biotechnological as a natural glutamate producer (Kinoshita, Udaka et al. 1957, J Gen Appl Microbiol, 3, 193-205). Furthermore, it is used for million ton scale production of different amino acids such as L-Lysin (see, e.g., WO 2007/141111). There are several methods for cultivation, characterization and genetic engineering, such as chromosomal deletions, integrations and expression vector design, which allow straightforward handling. The bacterium has the ability to grow aerobically on a variety of carbon sources like glucose, fructose, sucrose, mannitol, propionate and acetate. In addition it has been engineered to grow on alternative carbon sources such as glycerol, pentoses, amino sugars, β-glucans and starch.

In the past, several metabolic engineering strategies were applied to convert C. glutamicum into a carotenoid producer. To engineer C. glutamicum for C40 carotenoid production, the conversion of lycopene to decaprenoxanthin needs to be avoided through the inactivation of its lycopene elongase and ε-cyclase. The deletion of the respective genes crtYe/fEb resulted in the accumulation of the intermediate lycopene and a slight red color of the cells (Heider et al. ((2014), Frontiers in Bioengineering and Biotechnology, Vo. 2, Article 28). When overexpressing the endogenous genes crtE, crtB and crt in C. glutamicum ΔcrtEb the red phenotype intensified because of a better conversion of GGPP to the red chromophore lycopene. Heterologous expression of crtY from Pantoea ananatis ($crtY_{Pa}$) in the lycopene accumulating strain yielded the yellow pigment β-carotene. In the same study the production of small amounts of zeaxanthin was achieved by the additional expression of crtZ from P. ananatis ($crtZ_{Pa}$). The document also discloses a recombinant C. glutamicum strain in which a crtY-gene (from P. ananatis), a crtW-gene (from Brevundimonas aurantiaca) and a crtZ-gene (from P. ananatis) were overexpressed. However, this combination only resulted in astaxanthin titer of 0.14±0.01 mg/g DCW.

Amino acids are organic substances which contain amino and acid groups which are linked to an asymmetric carbon atom (Wu, 2009; Campbell and Reece, 2016). In nature, there are more than 300 amino acids existing but only 20 are used as building blocks for proteins. All the proteinogenic amino acids are α-enantiomers with $_L$-configuration, except for proline (Wu, 2009; Campbell and Reece, 2016). Humans and animals are not able to synthesize all amino acids, so that they have to obtain them through their diet. These amino acids are called essential amino acids (EAA). The eight essential amino acids are $_L$-valine, $_L$-leucine, $_L$-isoleucine, $_L$-methionine, $_L$-phenylalanine, $_L$-tryptophan, $_L$-threonine and $_L$-lysine (Leuchtenberger, Huthmacher and Drauz, 2005; Sahm et al., 2013). Amino acids are biotechnologically produced for the food, pharmaceutical and feed market (Mueller and Huebner, 2003). For the food market produced amino acids mainly are $_L$-aspartic acid, $_L$-phenylalanine and $_L$-glutamic acid. $_L$-Aspartic acid, $_L$-phenylalanine are used to produce the peptide sweetener $_L$-aspartyl $_L$-phenylalanyl methyl ester (Aspartame) (Mazur, 1984). This product is used to sweeten beverages (Leuchtenberger, Huthmacher and Drauz, 2005). $_L$-glutamic acid is being produced in the form of monosodium glutamate (MSG), which is used as a flavour enhancer (Kinoshita et al., 1957; Leuchtenberger, Huthmacher and Drauz, 2005). The amino acids $_{DL}$-methionine, $_L$-tryptophan, $_L$-threonine and $_L$-lysine have been produced over the last 30 years for the feed market and they hold a share of 56% of the total amino acid market (Leuchtenberger, Huthmacher and Drauz, 2005). The global market value for amino acids is expected to reach US$35.4 billion with a production of 10 million tons by 2022 (Grand View Research, 2015).

The amino acid glutamate has an important role in the central nervous system of vertebrates; it is an excitatory neurotransmitter (Meldrum, 2000; Campbell and Reece, 2009b). In 1908 Kikunae Ikeda discovered that the sodium salt of glutamic acid is the reason for the taste of kelp (konbu), which was later on called "umami" and is the fifth taste quality besides sweet, sour, bitter and salty (Kurihara, 2009). Glutamic acid tastes insipid and slightly sour (Fischer, 1906), while the salt elicits the typical umami taste (Kurihara, 2009). Free glutamate is present in many foodstuffs, e.g. tomato, potato, parmesan cheese, mushroom (Psalliota campestris), broccoli, and various fruits (e.g. strawberry, grape, peach) (Giacometti, 1979). Glutamate has been used as a flavour enhancer in Japan in the early $20^{th}$ century. It elicits a meat-like taste and is therefore often used to improve the vegetarian diet of the Japanese or Asian people in general. Since production of glutamate by hydrolysis of proteins (e.g. gluten, soy bean) (Han, 1929) was rather expensive and labourous, an alternative glutamate source was sought for. Microorganisms of many genera are able to accumulate $_L$-glutamate in their medium during fermentation, whereas C. glutamicum secreted the highest level of the amino acid (Asai, Aida and Ōishi, 1957). From this time on, C. glutamicum was used for the fermentative production of glutamate (Kinoshita et al., 1957). About 3.1 million tons of glutamate have been produced in 2015 (Ajinomoto Co., 2016a) and the market is expected to reach 4 million tons by 2023 with a value of US$15.5 billion and a CAGR of 7.5% up to the year 2023 (Global Market Insights, 2016).

C. glutamicum is able to synthesize a huge amount of glutamate under specific conditions, e.g. biotin limitation of the medium (Shiio, Otsuka and Takahashi, 1962) or the addition of antibiotics (e.g. ethambutol; EMB) (Radmacher et al., 2005) or detergents (e.g. tween 40) (Eggeling and Sahm, 1999). Glutamate is derived from 2-oxoglutarate, which is an intermediate of the TCA cycle. The glutamate dehydrogenase converts 2-oxoglutarate to glutamate under the consumption of NADPH (Börmann-El Kholy et al., 1993). The amino acid is transported out of the cell by the transporter YggB (Sahm et al., 2013).

The amino acid lysine is one of the essential amino acids which needs to be obtained through diet by humans and animals (Campbell and Reece, 2009a). It is important for the bone development, the cell division and the synthesis of nucleotides. In hospitals it is used in infusions (Spektrum-Lexikon der Chemie, 1998). Furthermore it is significant for a healthy development and growth in animals (e.g. fish) (Ovie and Eze, 2011).

The barrel principle explains that the growth factor, in this case amino acid, which is present in the least amount, limits the growth of the organism. Only when the need of the amino acid is met, the organism is able to grow until the next amino acid is limiting (Spektrum-Lexikon der Biologie, 1999c). The addition of L-lysine to the feed leads to a decreased amount of feed and a reduction of nitrogen release of 60% (Kircher and Pfefferle, 2001). Lysine is the first limiting amino acid in swine and the second in poultry (Ajinomoto Co., 2016b). Furthermore, $_L$-lysine is an important component for growth in animals. When $_L$-lysine was missing from the diet, the tested animals were not able to grow. But when $_L$-lysine was added, they were able to grow at a normal rate (Osbore and Mendel, 1914). The amount of $_L$-lysine in used feed (e.g. barley, wheat bran, corn germ meal) is generally low (Kircher and Pfefferle, 2001). 50 kg of soybean as feed can be replaced by 48.5 kg of corn plus 1.5 kg of lysine. Using this feed composition, the use of 1 ton of lysine would replace 33 tons of soybean (Ajinomoto Co., 2016b). Therefore a procedure to produce L-lysine needed to be invented. In 1958 a mutant strain of C. glutamicum with the ability to accumulate lysine was discovered (Kinoshita, Nakayama and Kitada, 1958). A homoserine-less mutant of C. glutamicum was able to accumulate 20 mg/ml $_L$-lysine by fermentation and further experiments showed the inhibition of $_L$-lysine production in the presence of homoserine and threonine (Nakayama, Kitada and Kinoshita, 1961). The large scale production of $_L$-lysine started in 1958 and has grown since then (Pfefferle et al., 2003). In 2015, 2.2 million tons of $_L$-lysine were produced for the global market and the demand is expected to reach 2.5 million tons by 2018 with a CAGR of 5.8% (from 2012-2018) (Byrne, 2014; Ajinomoto Co., 2016b). The global market value was US$3.5 billion in 2011 and the expectation for 2018 is an increase to US$5.9 billion with a CAGR of 9.1% (from 2012-2018) (Byre, 2014).

Oxaloacetate is the central intermediate from which lysine is produced. First a transaminase converts lysine to $_L$-aspartate. The reduction of $_L$-aspartate by aspartate kinase (Ask, LysC) and aspartate semialdehyde dehydrogenase (Asd) leads to aspartate semialdehyde. This is a branching point (Wink, 2011). The homoserine dehydrogenase (Hom) (Sahm et al., 2013) converts aspartate semialdehyde to homoserine, which can be metabolised to $_L$-methionine, $_L$-threonine and $_L$-isoleucine (Wink, 2011). At the other branch the enzyme dihydrodipicolinate synthase (DapA) converts the aspartate semialdehyde to dihydrodipicolinate which is converted to $_L$-piperideine-2,6-dicarboxylate (Wink, 2011; Sahm et al., 2013). This is another branching point, where the second amino group is added to $_L$-piperideine-2,6-dicarboxylate (Sahm et al., 2013).

Henke et al., 2016 disclose a method for production of lysine in *C. glutamicum*. However, no information or incentive is provided that the disclosed *C. glutamicum* strain is suitable for the simultaneous production of carotenoids and amino acids. US 2009/0221027 discloses that a heterologous metI overexpression in connection with the disruption of marR (denoted as crtR herein) may be used for production of methionine and carotenoids, but provides no further information, especially on the production of lysine and astaxanthine.

The markets for amino acids and carotenoids are growing and the demand for naturally produced carotenoids is increasing but hitherto only organisms which are able to produce either amino acids or carotenoids are known. There is a need for further and even better processes to produce carotenoids and amino acids from natural sources. The development of a *C. glutamicum* strain which can produce carotenoids and amino acids simultaneously is the main objective of this invention.

SUMMARY

One aspect of the present invention refers to a process for the preparation of astaxanthin and lysine in recombinant *C. glutamicum*, wherein in the genome of said recombinant *C. glutamicum* crtR, crtY from *C. glutamicum* and crtEb were deleted and crtEBI, crtY$_{Pa}$ and at least one recombinant sequence which comprises a nucleic acid sequence encoding for a crtZ-protein (crtZ-nucleic acid sequence), preferably from *F. pelagi* (crtZ$_{Fp}$-nucleic acid sequence) and at least one recombinant sequence which comprises a nucleic acid sequence encoding for a crtW-protein (crtW-nucleic acid sequence), preferably from *F. pelagi* (crtW$_{Fp}$-nucleic acid sequence), *B. aurantiaca* (crtW$_{Ba}$-nucleic acid sequence) or *Sphingomonas astaxanthinifaciens* (crtW$_{Sa}$-nucleic acid sequence) were introduced.

One preferred embodiment refers to a process according to the invention, wherein the crtZ$_{Fp}$-nucleic acid sequence is SEQ ID NO.: 1, or a nucleic acid sequence having at least 80% identity as set forth with SEQ ID NO.: 1, or a nucleic acid sequence that hybridizes with the complement of a nucleic acid sequence according to SEQ ID NO.: 1 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 2 and which amino acid sequence shows crtZ activity.

A further preferred embodiment refers to a process according to the invention, wherein the crtZ$_{Fp}$-nucleic acid sequence is SEQ ID NO.: 1.

A further preferred embodiment refers to a process according to the invention, wherein the crtW-nucleic acid sequence is SEQ ID NO.: 3 or SEQ ID NO.: 5 or is a nucleic acid sequence having at least 80% identity as set forth with SEQ ID NO.: 3 or 5, respectively, or a nucleic acid sequence that hybridizes with the complement of a nucleic acid sequence according to SEQ ID NO.: 3 or 5, respectively, under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or is a nucleic acid sequence encoding for an amino acid sequence having at least 80% identity with SEQ ID NO.: 4 or 6, respectively, and which amino acid sequence shows crtW activity; or is SEQ ID NO.: 7 or is a nucleic acid sequence having at least 80% identity as set forth with SEQ ID NO.: 7, or a nucleic acid sequence that hybridizes with the complement of a nucleic acid sequence according to SEQ ID NO.: 7 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 8 and which amino acid sequence shows crtW activity; or is SEQ ID NO.: 9, or is a nucleic acid sequence having at least 80% identity as set forth with SEQ ID NO.: 9, or a nucleic acid sequence that hybridizes with the complement of a nucleic acid sequence according to SEQ ID NO.: 9 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 10 and which amino acid sequence shows crtW activity.

A further preferred embodiment refers to a process according to the invention, wherein the crtW-protein is of SEQ ID NO.: 2, 4, 6 or 8.

A further preferred embodiment refers to a process according to the invention, wherein said recombinant *C. glutamicum* comprises a nucleic acid sequence encoding for a promotor 1 which is operatively linked to a crtZ$_{Fp}$-nucleic acid sequence according to claim 2 or claim 3.

A further preferred embodiment refers to a process according to the invention, wherein said recombinant *C. glutamicum* comprises a nucleic acid sequence encoding for a promotor 2 which is operatively linked to a crtW$_{Fp}$-, crtW$_{Ba}$-, or crtW$_{Sa}$-nucleic acid sequence according to claim 4 or 5.

A further preferred embodiment refers to a process according to the invention, wherein the promotor 1 and the promotor 2 are not induced by the same inducing compound.

A further preferred embodiment refers to a process according to the invention, wherein promotor 2 is a constitutively expressing promotor.

A further preferred embodiment refers to a process according to the invention, wherein induction of promotor activity of promotor 1 and induction of promotor activity of promotor 2 occur at different times.

A further preferred embodiment refers to a process according to the invention, wherein induction of promotor activity of promotor 1 occurs at the beginning of the cultivation, in the exponential growth phase within the first 6 hours.

A further preferred embodiment refers to a process according to the invention, wherein promotor 1 and promotor 2 are constitutively expressing promotors.

A further preferred embodiment refers to a process according to the invention, wherein said recombinant *C. glutamicum* produces L-lysine.

A further preferred embodiment refers to a process according to the invention, wherein said recombinant *C. glutamicum* is GRLys1ΔsugRΔldhA. In one embodiment, said recombinant *C. glutamicum* is LYS as described herein. In a further embodiment, said recombinant *C. glutamicum* includes the genetic modifications of GRLys1ΔsugRΔldhA.

A further preferred embodiment refers to a process according to the invention, wherein said recombinant *C. glutamicum* comprises the following modifications: deletion of sugR and deletion of LdhA, deletion of crtR insertion of crtEBI deletion of genes crtYe, crtYf and crtEb insertion of crt $Y_{Pa}$, preferably as Ptuf-crt$Y_{Pa}$, insertion of crt$Z_{Fp}$, preferably as pECXT99a_crt$Z_{Fp}$, insertion of crt$W_{Fp}$, preferably as pSH1-crt$W_{Fp}$. In one embodiment, said recombinant *C. glutamicum* is ASTA LYS as described herein.

Another aspect of the present invention refers to A recombinant *C. glutamicum*, wherein said recombinant *C. glutamicum* comprises a crtY-nucleic acid sequence, preferably a crt$Y_{Pa}$-nucleic acid sequence, further comprises a crtZ-nucleic acid sequence, which is not from *C. glutamicum*, preferably a crt$Z_{Fp}$-nucleic acid sequence, and further comprises a crtW-nucleic acid sequence, preferably a crt$W_{Fp}$-, crt$W_{Ba}$-, or crt$W_{Sa}$-nucleic acid sequence; more preferably, in the genome of said recombinant *C. glutamicum* crtR, crtY from *C. glutamicum* and crtEb were deleted and crtEBI, crt$Y_{Pa}$ and at least one recombinant sequence which comprises a nucleic acid sequence encoding for a crtZ-protein, preferably from *F. pelagi* (crt$Z_{Fp}$-nucleic acid sequence) and at least one recombinant sequence which comprises a nucleic acid sequence encoding for a crtW-protein, preferably from *F. pelagi* (crt$W_{Fp}$-nucleic acid sequence), *B. aurantiaca* (crt$W_{Ba}$-nucleic acid sequence) or *S. astaxanthinifaciens* (crt$W_{Sa}$-nucleic acid sequence) were introduced.

A preferred embodiment refers to a recombinant *C. glutamicum* according to the invention, wherein the nucleic acid sequence encoding for a crtZ-protein is a preferred crtZ-protein encoding nucleic acid sequence as described herein and the nucleic acid sequence encoding for a crtW-protein is a preferred crtW-protein encoding nucleic acid sequence as described herein.

A further preferred embodiment refers to a recombinant *C. glutamicum* comprising the following modifications: deletion of sugR and deletion of LdhA, deletion of crtR insertion of crtEBI deletion of genes crtYe, crtYf and crtEb insertion of crt $Y_{Pa}$, preferably as Ptuf-crt$Y_{Pa}$, insertion of crt$Z_{Fp}$, preferably as pECXT99a_crt$Z_{Fp}$, insertion of crt$W_{Fp}$, preferably as pSH1-crt$W_{Fp}$. In one embodiment, said recombinant *C. glutamicum* is ASTA LYS as described herein.

DEFINITIONS

BHT 2, 6-Di-tert-Butyl-4-methylphenol
bp base pair
CAGR Compound annual growth rate
CDW Cell dry weight
DMAPP Dimethylallyl pyrophosphate
DNA Desoxyribonucleic acid
DXP 1-deoxy-D-xylulose-5-phosphate
DXS 1-deoxy-D-xylulose 5-phosphate synthase
e.g. exempli gratia
EAA Essential amino acid
EDTA Ethylenediaminetetraacetate
EMB Ethambutol
FR Flanking region
GAP Glyceraldehyde 3-phosphate
GGPP Geranylgeranyl pyrophosphate
GRAS Generally recognized as safe
HPLC High performance liquid chromatography
IPP Isopentenyl pyrophosphate
IPTG Isopropyl-D-β-thiogalactopyranoside
kbp Kilo base pair
MCS Multiple cloning site
MEP Methylerythritol 4-phosphate
MOPS 3-(N-morpholino) propanesulfonic acid
MSG Monosodium glutamate
MVA Mevalonic acid
NADPH Nicotinamide adenine dinucleotide phosphate
OD Optical density
OTC Over-the-counter
PCR Polymerase chain reaction
PKS Protocatechuic acid
PTS Phosphotransferase system
rDNA Ribosomal DNA
RNA Ribonucleic acid
rpm Revolutions per minute
rRNA Ribosomal RNA
t Time
TCA Tricarboxylic acid cycle
UV Ultraviolet
Vis Visible
WT Wild type SugR refers to a nucleic acid sequence encoding for protein SugR which regulates the uptake of the carbon sources glucose, sucrose and fructose by repressing the glycolysis in *C. glutamicum* (see, e.g., SEQ ID NO: 61).

CrtR, also known as marR-type regulator or cg0725, refers to a nucleic acid sequence encoding a putative transcriptional regulator (Pfeiffer et al, 2016) (see, e.g., SEQ ID NO: 37)

CrtEBI refers to a nucleic acid sequence encoding an artificial operon. crtEBI was introduced into organisms according to the invention in form of, e.g., Ptuf-crtEBI (see, e.g., SEQ ID NO: 36), comprising the nucleic acid sequences Tuf, crtE, crtB and crtI (see, e.g., SEQ ID NOs: 29, 30, 32 and 34).

CrtY refers to a nucleic acid sequence encoding a lycopene cyclase [EC 5.5.1.19] from *C. glutamicum* (see, e.g., SEQ ID NOs: 23 and 25).

Crt$Y_{Pa}$ refers to a nucleic acid sequence encoding a lycopene cyclase from *Pantoea ananatis* (see, e.g., SEQ ID NO: 39).

CrtEb refers to a nucleic acid sequence encoding lycopene elongase [EC 2.5.1.-] (see, e.g., SEQ ID NO: 27).

LdhA refers to a nucleic acid sequence encoding a lactate dehydrogenase [EC 1.1.1.27](see, e.g., SEQ ID NO: 59).

CrtB refers to a nucleic acid sequence encoding a phytoene synthase [EC 2.5.1.32] (see, e.g., SEQ ID NO: 32).

CrtW a "crtW-nucleic acid sequence" or "crtW-gene" refers to a nucleic acid sequence encoding for an amino acid sequence having 4,4"-beta-ionone ring ketolase activity (see, e.g., SEQ ID NOs: 3, 5, 7, 9, 11).

"crtW-protein" refers to a protein having 4,4"-beta-ionone ring ketolase [EC1.14.11.B16] activity (see, e.g., SEQ ID NOs: 4, 6, 8, 10 and 12). "crtW activity" refers to the ability of an enzyme to catalyze the reaction of zeaxanthin to astaxanthin or/and beta-carotene to canthaxanthin.

CrtZ refers to a nucleic acid sequence encoding a β-carotene hydroxylase [EC 1.14.13.129](see, e.g., SEQ ID NO: 1, 13, 15, 17).

"crtZ-protein" refers to a protein having 3,3"-beta-ionone ring hydroxylase [EC1.14.13.129] activity (see, e.g., SEQ ID NO: 2, 14, 16, 18). "crtZ activity" refers to the ability of an enzyme to catalyze the reaction of β-carotene to zeaxanthin.

A "crtZ-nucleic acid sequence" or "crtZ-gene" refers to a nucleic acid sequence (see, e.g., SEQ ID NO: 1, 13, 15, 17) encoding for an amino acid sequence having 3,3"-beta-ionone ring hydroxylase activity.

The term "a" as used herein has the meaning of "one or more" or "at least one". The skilled person understands that in one preferred embodiment, this term refers to "one".

As defined herein, "overexpressing" an enzyme may be by any means known in the art, such as by introducing a gene (or put more generally, a nucleic acid molecule comprising a nucleic acid sequence) encoding gene such as crtW or crtZ, e.g. at least one copy of the gene, for example expressed from a stronger or unregulated promoter relative to the native gene, and/or by introducing multiple copies of said gene such as an crtW- or crtZ-encoding nucleic acid molecule/gene. As referred to herein, a strong promoter is one which expresses a gene at a high level, or at least at a higher level than effected by its native promoter. The term "strong promoter" is a term well known and widely used in the art and many strong promoters are known in the art, or can be identified by routine experimentation. The use of a non-native promoter may advantageously have the effect of relieving a gene such as the crtW- or crtZ-encoding gene of transcriptional repression, as at least some of any repressive elements will be located in the native promoter region. By replacing the native promoter with a non-native promoter devoid of repressive elements responsive to the effects of pathway products, the gene, such as crtW- or crtZ-encoding gene, will be at least partly relieved of transcriptional repression.

A sequence is "operatively linked" to a promoter sequence (promoter) (or vice versa) when the expression of said gene is triggered/controlled by said promoter.

The term "overproduction" refers to the production of a recombinant protein, which is based on the overexpression of the corresponding, said protein encoding recombinant nucleotide sequence.

Recombinant nucleotide sequence as used herein are nucleotide sequences formed by laboratory methods of genetic recombination (such as molecular cloning) to bring together genetic material from multiple sources, creating sequences that would not otherwise be found in the genome. The term "recombinant" in connection with proteins refers to proteins of which said protein encoding sequences are part of a recombinant nucleotide sequence.

A "recombinant gram-positive bacterium" as used herein refers to a gram-positive bacterium which comprises a recombinant nucleotide sequence comprising at least one crtZ-nucleic acid sequence and at least one crtW-nucleic acid sequence. Notably, said sequences in the recombinant sequence can originate from the genome of the recombinant host cell or can originate from the genome of a different bacterium.

It is understood that all embodiments of the present invention can be combined as long as such a combination does not contradict any law of nature. Of course, such combinations are excluded.

Sequences

SEQ ID NO.: 1—a crtZ-encoding nucleic acid sequence from F. pelagi (a crtZ$_{Fp}$-gene):
ATGACGATCTGGACTCTCTACTACGTCTGTCTCACCCTCGTCACGATCGG
TTTGATGGAGGTTTATGCATGGTGGGCGCACAAGTTCATCATGCATGGCA
AATTCGGTTGGGGCTGGCATAAGTCCCACCACGAGGAAACCGAAGGGTGG
TTCGAGAAGAACGATCTCTACGCTGTCGTTTTCGCCGGCTTCGCGATAGC
GCTGTTCATGGTCGGACATTTCCTTTCTCCGACCCTGCTCGCCATCGCCT
GGGGCATCACGCTTTACGGATTACTCTACTTCGTTGCCCATGATGGACTT
GTCCATCAGCGCTGGCCGTTCAACTACGTGCCGCATCGAGGTTATGCAAA
ACGCCTGGTTCAAGCTCATCGTCTGCACCATGCGGTGGAAGGCCGCGAGC
ACTGCGTCTCGTTCGGCTTTCTCTATGCGCCGCCGATTGAAAAGCTGAAG
CGCGATTTGCGTGAGTCCGGAATTCTCGAACGGGAGCGCATCGAGCGGTC
TCTGGACCAGCAAGGCTCCGCCCACGCGCCGGTTCGGTAA SEQ ID NO.: 2—a crtZ-protein from F. pelagi encoded by SEQ ID NO.: 1 (a crtZ$_{Fp}$-protein):
MTIWTLYYVCLTLVTIGLMEVYAWWAHKFIMHGKFGWGWHKSHHEETEGW
FEKNDLYAVVFAGFAIALFMVGHFLSPTLLAIAWGITLYGLLYFVAHDGL
VHQRWPFNYVPHRGYAKRLVQAHRLHHAVEGREHCVSFGFLYAPPIEKLK
RDLRESGILERERIERSLDQQGSAHAPVR*

SEQ ID NO.: 3—a crtW-encoding nucleic acid sequence from F. pelagi (a crtW1$_{Fp}$-gene):
ATGACCCTCAGCCCAACCTCACGCCTGATCCCGGCAAGTGCGTTACCGCG
ATCCACACCCGCCGACTCACCCAAAATCAGACCCTACCAAACGACGATTG
GCCTGACGCTCTGTGCCGTGCTGCTGGCATCGTGGTTCGCAATACACGTC
TCAGCGATATTCTTCCTCGACATCAATTTCAGCACGTTGCCTCTCGCACC
ATTGATCACGGTGTTCCAGTGCTGGTTGACGGTGGGGCTTTTCATCCTGG
CTCACGACGCCATGCATGGTTCGCTGGCGCCGGGTCGAACGCGTTTGAAT
GCCGTAATCGGCGGGTTCATCCTGTTCGTCTACGCGGGATTTGCGTGGAA
AAAGATCAGAGATGCTCACTTCGCACACCACGACGCACCCGGTACACCGG
CCGACCCGGATTTCTACGCAGATGATCCGGAGAATTTCTGGCCTTGGTTC
GGCACCTTCTTCTCACGTTATTTCGGATGGAGATCGGTCGCATTCGTCTC
GACCGTCGTGACGTTTTATCTCGTCATACTGGATGCATCTGTGACGAACG
TGGTTCTATTTTACGGCTTGCCGTCACTGCTTTCGTCATTGCAGCTCTTC
TACTTCGGAACCTACCGCCCGCATCGACACGAAGAATCGGGCACCTTTGC
CGACGCGCATAACACACGTTCGAGCGAATTCGGTTACGTGGCCTCGCTAT
TCTCCTGCTTCCATTTTGGCTACCACCATGAGCACCATTTGGCGCCATGG
ACGCCTTGGTGGGCTCTGCCGCATACTCGCCAGTCCTAA SEQ ID NO.: 4—a crtW-protein from F. pelagi encoded by SEQ ID NO.: 3 (a crtW1$_{Fp}$-protein):
MTLSPTSRLIPASALPRSTPADSPKIRPYQTTIGLTLCAVLLASWFAIHV
SAIFFLDINFSTLPLAPLITVFQCWLTVGLFILAHDAMHGSLAPGRTRLN
AVIGGFILFVYAGFAWKKIRDAHFAHHDAPGTPADPDFYADDPENFWPWF
GTFFSRYFGWRSVAFVSTVVTFYLVILDASVTNVVLFYGLPSLLSSLQLF
YFGTYRPHRHEESGTFADAHNTRSSEFGYVASLFSCFHFGYHHEHHLAPW
TPWWALPHTRQS*

SEQ ID NO.: 5—another crtW-encoding nucleic acid sequence from F. pelagi (a crtW2$_{Fp}$-gene):
ATGAGACCCTACCAAACGACGATTGGCCTGACGCTCTGTGCCGTGCTGCT
GGCATCGTGGTTCGCAATACACGTCTCAGCGATATTCTTCCTCGACATCA
ATTTCAGCACGTTGCCTCTCGCACCATTGATCACGGTGTTCCAGTGCTGG
TTGACGGTGGGGCTTTTCATCCTGGCTCACGACGCCATGCATGGTTCGCT
GGCGCCGGGTCGAACGCGTTTGAATGCCGTAATCGGCGGGTTCATCCTGT
TCGTCTACGCGGGATTTGCGTGGAAAAAGATCAGAGATGCTCACTTCGCA
CACCACGACGCACCCGGTACACCGGCCGACCCGGATTTCTACGCAGATGA
TCCGGAGAATTTCTGGCCTTGGTTCGGCACCTTCTTCTCACGTTATTTCG
GATGGAGATCGGTCGCATTCGTCTCGACCGTCGTGACGTTTTATCTCGTC
ATACTGGATGCATCTGTGACGAACGTGGTTCTATTTTACGGCTTGCCGTC
ACTGCTTTCGTCATTGCAGCTCTTCTACTTCGGAACCTACCGCCCGCATC
GACACGAAGAATCGGGCACCTTTGCCGACGCGCATAACACACGTTCGAGC
GAATTCGGTTACGTGGCCTCGCTATTCTCCTGCTTCCATTTTGGCTACCA
CCATGAGCACCATTTGGCGCCATGGACGCCTTGGTGGGCTCTGCCGCATA
CTCGCCAGTCCTAA SEQ ID NO.: 6—another crtW-protein from F. pelagi
encoded by SEQ ID NO.: 5 (a crtW2$_{Fp}$-protein):
MRPYQTTIGLTLCAVLLASWFAIHVSAIFFLDINFSTLPLAPLITVFQCW
LTVGLFILAHDAMHGSLAPGRTRLNAVIGGFILFVYAGFAWKKIRDAHFA
HHDAPGTPADPDFYADDPENFWPWFGTFFSRYFGWRSVAFVSTVVTFYLV
ILDASVTNVVLFYGLPSLLSSLQLFYFGTYRPHRHEESGTFADAHNTRSS
EFGYVASLFSCFHFGYHHEHHLAPWTPWWALPHTRQS*

SEQ ID NO.: 7—a crtW-encoding nucleic acid
sequence from B. aurantiaca (a crtW$_{Ba}$-gene):
ATGACCGCCGCCGTCGCCGAGCCACGCACCGTCCCGCGCCAGACCTGGAT
CGGTCTGACCCTGGCGGGAATGATCGTGGCGGGATGGGCGGTTCTGCATG
TCTACGGCGTCTATTTTCACCGATGGGGGCCGTTGACCCTGGTGATCGCC
CCGGCGATCGTGGCGGTCCAGACCTGGTTGTCGGTCGGCCTTTTCATCGT
CGCCCATGACGCCATGCACGGCTCCCTGGCGCCGGGACGGCCGCGGCTGA
ACGCCGCAGTCGGCCGGCTGACCCTGGGGCTCTATGCGGGCTTCCGCTTC
GATCGGCTGAAGACGGCGCACCACGCCCACCACGCCGCGCCCGGCACGGC
CGACGACCCGGATTTTCACGCCCCGGCGCCCCGCGCCTTCCTTCCCTGGT
TCCTGAACTTCTTTCGCACCTATTTCGGCTGGCGCGAGATGGCGGTCCTG
ACCGCCCTGGTCCTGATCGCCCTCTTCGGCCTGGGGGCGCGGCCGGCCAA
TCTCCTGACCTTCTGGGCCGCGCCGGCCCTGCTTTCAGCGCTTCAGCTCT
TCACCTTCGGCACCTGGCTGCCGCACCGCCACACCGACCAGCCGTTCGCC
GACGCGCACCACGCCCGCAGCAGCGGCTACGGCCCCGTGCTTTCCCTGCT
CACCTGTTTCCACTTCGGCCGCCACCACGAACACCATCTGAGCCCCTGGC
GGCCCTGGTGGCGTCTGTGGCGCGGCGAGTCTTGA SEQ ID NO.: 8—a crtW-protein from B. aurantiaca a
(crtW$_{Ba}$-protein):
MTAAVAEPRTVPRQTWIGLTLAGMIVAGWAVLHVYGVYFHRWGPLTLVIA
PAIVAVQTWLSVGLFIVAHDAMHGSLAPGRPRLNAAVGRLTLGLYAGFRF
DRLKTAHHAHHAAPGTADDPDFHAPAPRAFLPWFLNFFRTYFGWREMAVL
TALVLIALFGLGARPANLLTFWAAPALLSALQLFTFGTWLPHRHTDQPFA
DAHHARSSGYGPVLSLLTCFHFGRHHEHHLSPWRPWWRLWRGES*

SEQ ID NO.: 9—a crtW-encoding
nucleic acid sequence from
S. astaxanthinifaciens (a crtW$_{Sa}$-gene):
ATGGCCCCCATGCTCAGTGACGCGCAGCGCCGCCGCCAGGCGATGATCGG
GCTCGGCCTCGCCGCCGCGATCACCGCCGCCTTCGTCGCGCTGCATGTCT
GGTCGGTCTTCTTCCTGCCGCTCGAGGGCGCGGGCTGGTGGCTCGCGCTG
CCGATCGTCGCGGTGCAGACCTGGCTCAGCGTCGGCCTGTTCATCGTCGC
GCATGACGCGATGCACGGCAGCCTCGCGCCGGGCCGCCCGGCGACCAACC
TCTTCTGGGGCGGCTGACGCTGCTGCTCTACGCGGGCTTCCGGTTGGAC
CGCCTTTCGCCCAAGCATTTCGACCACCACCGCCATGTCGGGACCGAGCG
CGATCCCGATTTCTCGGTCGATCATCCGACCCGCTTCTGGCCCTGGTATT
ATGCCTTCATGCGGCGCTATTTCGGGCTTCGCGAATATCTGGTGCTGAAC
GCGCTGGTGCTGGCCTACGTGCTGGTGCTGAAGGCGCCGCTCGGCAATCT
GCTCCTGTTCTGGGCGCTGCCCTCGATCCTGTCCTCGATCCAGCTCTTCT
ATTTCGGCACCTACCTTCCGCACCGGCACGAGGACGCGCCCTTCGCCGAC
CAGCACAATGCCCGCAGCAACGACTTTCCGGTCTGGCTGTCGCTGCTGAC
CTGCTTCCACTTCGGCTATCACCGCGAGCATCACCTCAGCCCCGGCACCC
CCTGGTGGCAGCTGCCCCGGCGGCGGCGCGAGCTTGCGCTTCCCGCCTAA SEQ ID NO.: 10—a crtW-protein from
S. astaxanthinifaciens (a crtW$_{Sa}$-protein):
MAPMLSDAQRRRQAMIGLGLAAAITAAFVALHVWSVFFLPLEGAGWWLAL
PIVAVQTWLSVGLFIVAHDAMHGSLAPGRPATNLFWGRLTLLLYAGFWLD
RLSPKHFDHHRHVGTERDPDFSVDHPTRFWPWYYAFMRRYFGLREYLVLN
ALVLAYVLVLKAPLGNLLLFWALPSILSSIQLFYFGTYLPHRHEDAPFAD
QHNARSNDFPVWLSLLTCFHFGYHREHHLSPGTPWWQLPRRRELALPA*

SEQ ID NO.: 11—a crtW-encoding
nucleic acid sequence from
Brevundimonas bacteroides (a crtW$_{Bb}$-gene):
ATGACGCGGGAACGCCAGACCGTCGTCGGCCTGACGCTGGCCGCCGTCAT
CGTGGGCGGCTGGATGACGCTGCACGTCTGGGGCGTGTTCTTTCAGCCGC
TGTCGGGAACAGCGCTGTTCGTGGTCCCGCTGCTGATCCTGACCCAGAGC
TGGCTCGGTGCGGACATGTTCATCGTCGCCCATGACGCCATGCACGGTTC
ACTGGCCCCGGTCGCCCCCGCCTCAACGCCGTCGATCGGCAGATCTGCG
TCGGGGCCTATGCGGCCTTCTCGTATCGCAAGCTGAACGTCTGCCACCAC
CAGCACCACCGCGCGCCGGGCACGGCCGAGGACCCCGACTTCCATGCCGA
GCGGCCCGAGGCCTTCCTGCCGTGGTTCTATGGCTTCTTCACCCGATACT
TCGGCTGGCGCGAGTTCACGATCGTGACGGCGGTGCTGATCGCCTATCTG
CTGATCGGGGCGACGGTGGTGAACCTGATCCTGTTCTGGGCCGTGCCCGC
GGTCCTCAGTGCGCTCCAGCTGTTCGTGTTCGGGACCTGGCTGCCGCATC
GGCATACGGCGGGCGACGGGTTCGCGGATCATCACCATGCGCGGACGATC
CCGATGCCGTGGGTCGCGTCGCTTCTGGCCTGCTTCCACTTCGGAATGCA
TCACGAGCACCACCTGACGCCAGCCGCGCCTTGGTGGAGACTGCCTGAGG
TTCGAAAGGCTATGCTGGCGCGTAGCGAACGTCTCTAA SEQ ID NO.: 12—a crtW-protein from B. bacteroides
encoded by SEQ ID NO.: 11 (a crtW$_{Bb}$-protein):
MTREROTVVGLTLAAVIVGGWMTLHVWGVFFQPLSGTALFVVPLLILTQS
WLGAGMFIVAHDAMHGSLAPGRPRLNAVIGQICVGAYAAFSYRKLNVCHH
QHHRAPGTAEDPDFHAERPEAFLPWFYGFFTRYFGWREFTIVTAVLIAYL
LIGATVVNLILFWAVPAVLSALQLFVFGTWLPHRHTAGDGFADHHHARTI
PMPWVASLLACFHFGMHHEHHLTPAAPWWRLPEVRKAMLARSERL*

SEQ ID NO.: 13—a crtZ-encoding nucleic acid
sequence from B. bacteroides (a crtZ$_{Bb}$-gene):
ATGACGATCGTCTGGTTCACCCTGCTGACGCTGGCCGTCTTCTTCCTCAT
GGAAGGGGTCGCCTGGACAACGCACCGCTACATCATGCATGGGCCGCTCG
GCTGGGGCTGGCACCGCGATCACCATGAGCCGCACGACAAGACCTTCGAG
GTCAACGACCTCTATGGCGTGGTCGGGGCCGTGGTCGGGACCGGTCTGTT
CGTCGTCGCCTGGTTGACGGACCTTTGGTGGGTGCGGGCGACCGCACTGG
GCGTCACGCTGTACGGCGTGGTCTACGCCTTCGTGCACGACGGCCTGGTG
CACCAGCGATGGCCGTTCCACTGGATGCCGAAGAACGGTTATGCGCGGAG
GCTGGTTCAGGCGCACAAGCTGCATCACGCGGTTCAGACGCGCGATGGGG
CCGTGTCGTTCGGCTTCGTCTTCGCGCCAAACCCCCAGCGGCTCAGCGCC
ATCCTGAAGGCGCGCCGGGCAGAGCGCGCCGCGACGGACATCCCGGCCGA
GTAA SEQ ID NO.: 14—a crtZ-protein from B. bacteroides
encoded by SEQ ID NO.: 13 (a crtZ$_{Bb}$-protein):
MTIVWFTLLTLAVFFLMEGVAWTTHRYIMHGPLGWGWHRDHHEPHDKTFE
VNDLYGVVGAVVGTGLFVVAWLTDLWWVRATALGVTLYGVVYAFVHDGLV
HQRWPFHWMPKNGYARRLVQAHKLHHAVQTRDGAVSFGFVFAPNPQRLSA
ILKARRAERAATDIPAE*

SEQ ID NO.: 15—a crtZ-encoding
nucleic acid sequence from
S. astaxanthinifaciens (a crtZ$_{Sa}$-gene):
ATGTCCTGGCCTGCCGGTCTCGCCCTGTTCGTATCGACGGTCCTTCTGAT
GGAGGGCTTCGCCTATGTCCTCCACCGCTTCGTGATGCACTCGCGGCTCG
GCTGGAACTGGCACGAAAGCCATCATCGCGCGCGGACCGGCTGGTTCGAG
CGGAACGACCTCTATGCCGTGGTCTTCGCTTTGCCCTCGATCCTGCTGAT
CTGGGGCGGGCTCAATGGCGGCTGGGGCGACTGGGCGACGTGGATGGGGG
CCGGGGTGGCCTTCTACGGGGTGATCTATTTCGGCTTTCACGACGTCATC
GTCCACGGCCGGCTGCCGCACCGGATCGTGCCGCGTTCGACCTATTTCAA
GCGGATCGTCCAGGCGCACAAGCTGCACCATGCGGTCGAGAGCCGCGACG
GGGCGGTGAGCTTCGGCTTCCTTTACGCCCCGCCGGTCGAGCGCCTGAAG
CAGGCGCTCCAGGCCAGCCGCGAGGCGCAGCTCAGGCGTGCGCGGGGCGG
GTCCACAGCCCGTCACGAGGAGCGGGCCTAA SEQ ID NO.: 16—a crtZ-protein from
S. astaxanthinifaciens encoded by SEQ ID NO.:
15 (a crtZs$_a$-protein):
MSWPAGLALFVSTVLLMEGFAYVLHRFVMHSRLGWNWHESHHRARTGWFE
RNDLYAVVFALPSILLIWGGLNGGWGDWATWMGAGVAFYGVIYFGFHDVI
VHGRLPHRIVPRSTYFKRIVQAHKLHHAVESRDGAVSFGPLYAPPVERLK
QALQASREAQLRRARGGSTARHEERA*

SEQ ID NO.: 17—a crtZ-encoding nucleic acid
sequence from B. vesicularis (a crtZ$_{Bv}$-gene):
ATGTCCTGGCCGACGATGATCCTGCTGTTTCTCGCCACCTTCCTGGGGAT
GGAGGTCTTCGCCTGGGCGATGCATCGCTATGTCATGCACGGCCTGCTGT
GGACCTGGCACCGTAGCCACCATGAGCCGCACGACGACGTGCTGGAAAAG
AACGACCTGTTCGCCGTGGTGTTCGCCGCCCGGCCATCATCCTCGTCGC
CTTGGGCCTGCATCTGTGGCCTTGGGCGCTGCCGATCGGCCTGGGCGTCA
CGGCCTATGGACTGGTCTATTTCTTCTTCCACGACGGGCTGGTGCATCGC
CGGTTCCCGACGGGAATCGCGGGCCGCTCAGGGTTCTGGACGCGGCGCAT
TCAGGCCCACCGGCTGCATCACGCGGTCGGACGCGTGAGGGCTGCGTGT
CGTTCGGCTTCCTGTGGGTGCGTCGGCGCGCGCTGAAGGCCGAACTG
TCTCAGAAGCGCGGCGCTTCCAGCAACGGCGCCTAA SEQ ID NO.: 18—a crtZ-protein from B. vesicularis
encoded by SEQ ID NO.: 17 (a crtZ$_{Bv}$-protein):
MSWPTMILLLFLATFLGMEVFAWAMHRYVMHGLLWTWHRSHHEPHDDVLEK
NDLFAVVFAAPAIILVALGLHLWPWALPIGLGVTAYGLVYFFFHDGLVHR
RFPTGIAGRSGFWTRRIQAHRLHHAVRTREGCVSFGFLWVRSARALKAEL
SQKRGASSNGA*

SEQ ID NO.: 19—a crtW1-encoding nucleic acid
sequence from B. vesicularis (a crtW1$_{Bv}$-gene):
ATGGGGCAAGCGAACAGGATGCTTACGGGGCCGCGATGCGCTAAGTGTCG
CGCCATGTTCGCCGTCACGCCAATGTCACGGGTCGTCCCGAACCAGGCCC
TGATCGGCCTGACGCTGGCTGGCCTGATCGCCGCGGTCTGGCTGACCCTG
CACATCTACGGCGTCTATTTTCATCGCTGGACGATCTGGAGCATCCTGAC
CGTTCCGCTGATCGTCGCCGTCCAGACCTGGCTATCCGTCGGCCTGTTCA
TCGTCGCCCACGACGCCATGCACGGCTCGCTGGCCCCGGGACGCCCACGG
CTGAACACGGCGATCGGCAGCCTGGCGCTGGCCCTCTACGCCGGATTTCG
GTTCGCGCCTTTGAAGATCGCACACCACGCCCATCACGCTGCGCCTGGTA
CGGCGGACGATCCCGACTTTCACGCCGACGCCCCGCGCTTTCCTGCCC
TGGTTCTACGGCTTTTTCCGCACCTATTTCGGCTGGCGAGAACTGGCCGT
TCTGACGGTGCTCGTGGCCGTTGCGGTGCTGATCCTCGGCGCCCGCGTGC
CCAATCTTCTGGCCTTTTGGGCCGCGCCCGCCCTGCTATCGGCGCTACAG
CTTTTCACATTCGGAACCTGGCTGCCTCACAGGCATACCGACGACGCTTT
CCCCGACCACCACAACGCCCGCACCAGCCCCTTCGGCCCGGTCCTGTCGT
TGCTCACCTGCTTCCACTTCGGCCGCCACCACGAACACCTCCTGACCCCC
TGGAAGCCCTGGTGGAGTTTGTTCAGCTAG SEQ ID NO.: 20—a crtW1-protein from *B. vesicularis* encoded by SEQ ID NO.: 19 (a crtW1$_{Bv}$-protein):
MGQANRMLTGPRCAKCRAMFAVTPMSRVVPNQALIGLTLAGLIAAVWLTL
HIYGVYFHRWTIWSILTVPLIVAVQTWLSVGLFIVAHDAMHGSLAPGRPR
LNTAIGSLALALYAGFRFAPLKIAHHAHHAAPGTADDPDFHADAPRAFLP
WFYGFFRTYFGWRELAVLTVLVAVAVLILGARVPNLLAFWAAPALLSALQ
LFTFGTWLPHRHTDDAFPDHHNARTSPFGPVLSLLTCFHFGRHHEHLLTP
WKPWWSLFS*

SEQ ID NO.: 21—a crtW2-encoding nucleic acid sequence from *B. vesicularis* (a crtW2Bv-gene):
ATGCGGCAAGCGAACAGGATGCTTACGGGGCCGCGATGCGCTAAGTGTCG
CGCCATGTTCGCCGTCACGCCAATGTCACGGGTCGTCCCGAACCAGGCCC
TGATCGGCCTGACGCTGGCTGGCCTGATCGCCGCGGTCTGGCTGACCCTG
CACATCTACGGCGTCTATTTTCATCGCTGGACGATCTGGAGCATCCTGAC
CGTTCCGCTGATCGTCGCCGTCCAGACCTGGCTATCCGTCGGCCTGTTCA
TCGTCGCCCACGACGCCATGCACGGCTCGCTGGCCCCGGGACGCCCACGG
CTGAACACGGCGATCGGCAGCCTGGCGCTGGCCCTCTACGCCGGATTTCG
GTTCGCGCCTTTGAAGATCGCACACCACGCCCATCACGCTGCGCCTGGTA
CGGCGGACGATCCCGACTTTCACGCCGACGCCCCGCGCTTTCCTGCCC
TGGTTCTACGGCTTTTTCCGCACCTATTTCGGCTGGCGAGAACTGGCCGT
TCTGACGGTGCTCGTGGCCGTTGCGGTGCTGATCCTCGGCGCCCGCGTGC
CCAATCTTCTGGCCTTTTGGGCCGCGCCCGCCCTGCTATCGGCGCTACAG
CTTTTCACATTCGGAACCTGGCTGCCTCACAGGCATACCGACGACGCTTT
CCCCGACCACCACAACGCCCGCACCAGCCCCTTCGGCCCGGTCCTGTCGT
TGCTCACCTGCTTCCACTTCGGCCGCCACCACGAACACCTCCTGACCCCC
TGGAAGCCCTGGTGGAGTTTGTTCAGCTAG SEQ ID NO.: 22—a crtW1-protein from *B. vesicularis* encoded by SEQ ID NO.: 19 (a crtW1Bv-protein):
MRQANRMLTGPRCAKCRAMFAVTPMSRVVPNQALIGLTLAGLIAAVWLTL
HIYGVYFHRWTIWSILTVPLIVAVQTWLSVGLFIVAHDAMHGSLAPGRPR
LNTAIGSLALALYAGFRFAPLKIAHHAHHAAPGTADDPDFHADAPRAFLP
WFYGFFRTYFGWRELAVLTVLVAVAVLILGARVPNLLAFWAAPALLSALQ
LFTFGTWLPHRHTDDAFPDHHNARTSPFGPVLSLLTCFHFGRHHEHLLTP
WKPWWSLFS*

SEQ ID NO: 23—a crtYe encoding nucleic acid sequence from *C. glutamicum* (a crtYe-gene)
ttgatccctatcatcgatatttcacaaaatgagcaagatagcgatatttt
tatggcctttatttatctaggtactctcctagttctcattggtgcatgg
ctttgtgcgaccaccgttggaagctagcgttcttccgccatccgttacga
gcaattctttcggtaggtgctgcatatattggatttcttttatgggatat
atttggcattattactggcactttttatcgcggagactcagcgtttatgt
ccggtattaaccttgcaccccatatgcccattgaagaactttttttctta
ttcttcctctgctacatcaccctcaaccttacctcggcagcagcattatg
gcttaaagcaccactgcctaaaaaacccggtaaaaagtctcccctcacac
cacagcgcgatactttccaaccaactaccactcccgaggttgaaccatga SEQ ID NO: 24—a crtYe-protein from *C. glutamicum* (a crtYe-protein)
MIPIIDISQNEQDSDIFMAFIYLGTLLVLIGCMALCDHRWKLAFFRHPLR
AILSVGAAYIGFLLWDIFGIITGTFYRGDSAFMSGINLAPHMPIEELFFL
FFLCYITLNLTSAAALWLKAPLPKKPGKKSPLTPQRDTFQPTTTPEVEP SEQ ID NO: 25—a crtYf encoding nucleic acid sequence from *C. glutamicum* (a crtYf-gene)
Atgacttatatttttataagcattccttttttagcaatagccatggtcct
atttgtcttaaagctgcagtctggaacacctaaacttttaccaatcaccg
ctgtcagtgcccttaccctatgttccctaactatcatatttgataacctc
atggtttgggctgatctctttggatatggcgatacccagcaccttggcat
ttggctcggtttaatcccccctagaggatcttttctatccgctcttcgcag
tacttctgattcctgccctatggttgcctggaaatatgtttaaacgcagg
aaaaaacgtccacaccattccttacccaccatcgccaatggaagcatcac
tactagatccaccaccacgcaatctgagccagaaaagccgtag SEQ ID NO: 26—a crtYf-protein from *C. glutamicum* (a crtYf-protein)
MTYIFISIPFLAIAMVLFVLKLQSGTPKLLPITAVSALTLCSLTIIFDNL
MVWADLFGYGDTQHLGIWLGLIPLEDLFYPLF SEQ ID NO: 27—a crtEb encoding nucleic acid sequence from *C. glutamicum* (a crtEb-gene)
Atgatggaaaaaataagactaattctattgtcatctcgccccattagctg
gatcaataccgcctaccccctttggtctggcctacctattaaatgcaggag
agattgactggctgttttggctaggcatcgtattifttcttatcccgtat
aacatcgccatgtatggtatcaacgatgtttttgattacgaatctgatat
gcgtaatccccgcaaaggcggcgtcgagggggccgtgctaccgaaaagtt
cccacagcacactgttatgggcctcggctatctcaacaattcctttccta
gttattcttttcatatttggcacctggatgtcgtctttatggctgacact
ctcagtgctagcagtgattgcttattcagcaccgaaattgcgttttaaag
aacgcccctttatcgatgctctaacatcttctactcacttcacttcacct
gcattaatcggtgcaacgatcactggaacatctccttcagcagcgatgtg
gatagcactgggatccttifttcttgtggggcatggccagtcagatccttg
gagcagtacaggatgttaatgcagaccgggaagctaatctgagctcaatt
gccactgtaattggggcgcgtggagccattcggctttcagtagtacttta
tttactagctgctgtgttagtcactactttgcctaatccggcgtggatca
tcgggattgcgattctaacttacgtatttaatgccgcacgattttggaac
attacagatgccagttgtgaacaggctaatcgcagttggaaagttttcct
gtggctgaactactttgttggtgctgtgataacgatactgctaatagcaa
ttcatcagatataa SEQ ID NO: 28—a crtEb-protein from *C. glutamicum* (a crtEb-protein)
MMEKIRLILLSSRPISWINTAYPFGLAYLLNAGEIDWLFWLGIVFFLIPY
NIAMYGINDVFDYESDMRNPRKGGVEGAVLPKSSHSTLLWASAISTIPFL
VILFIFGTWMSSLWLTLSVLAVIAYSAPKLRFKERPFIDALTSSTHFTSP
ALIGATITGTSPSAAMWIALGSFFLWGMASQILGAVQDVNADREANLSSI
ATVIGARGAIRLSVVLYLLAAVLVTTLPNPAWIIGIAILTYVFNAARFWN
ITDASCEQANRSWKVFLWLNYFVGAVITILLIAIHQI SEQ ID NO: 29—a TUF promotor *C. glutamicum*
TGGCCGTTACCCTGCGAATGTCCACAGGGTAGCTGGTAGTTTGAAAATCA
ACGCCGTTGCCCTTAGGATTCAGTAACTGGCACATTTTGTAATGCGCTAG
ATCTGTGTGCTCAGTCTTCCAGGCTGCTTATCACAGTGAAAGCAAAACCA
ATTCGTGGCTGCGAAAGTCGTAGCCACCACGAAGTCCAGGAGGACATACA SEQ ID NO: 30—a crtE encoding nucleic acid sequence from *C. glutamicum* (a crtE-gene)
Atggacaatggcatgacaatcaccacagaacattcaactcatcctgatct
tgatttcaatgatgagatttatcgggaactaaaccgcatctgcgcttcgc
tatctcaacagtgcagcacatatcaaccagagttccgtacctgcctagat
gctgcttccaagctttgcgaggtggcaagttaatccgccctcgaatgct
actggggctatacaacacgcttgtagacgatgacattgaggtcaaactca
acaccgttttacaggtagcagtggctttagaactactgcatttttccctt
ttggttcatgacgatgttattgacggagacctctatcgccgaggcaaact
taattttattgggcagattctcatgcatcgcacacctgaaagttttgcac
aaatccagcgcgatccagagcatctagattgggcacaatctaatggactg
cttatgggaaatctttttcttgctgccacccatcaaatcttcgcgcgcct
tgaccttccacatcaccaacgggttcgacttttagatttactcaaccaca
cgataaatgacactattgtgggtgagtttcttgatgtgggattaagcagc
aaagccatcagccccaatatggacattgctctagaaatgagtcggctaaa
aacagccacatacacttttgaacttccaatgagagcagcggcaattctcg
cggaactacctcaggagattgaaacaaagataggtgagataggcacaaac
ttgggcatcgcttatcaattgcaggacgattacttatctacttttggtga
cgcagccgaacacggcaaagatgccttttctgaccttcgagaaggaaaag
aaactacaattatcgccttcgctcgagatactgctaaatggactgatatt
caagacaacttcggctccgcagatctgagcacctctcaggcagagcgaat
tcaacatcttctcatacagtgtggagcaaagaatcactccttgaatgcca
tctccgaccacttaaatatctgccgttcgatgatcaaaacactaagcccc
caggtagatcccaaggctcaaaatttattacttaaacaagttgagcaact
agccagccgcaaatcttag SEQ ID NO: 31—a crtE-protein from *C. glutamicum* (a crtE-protein)
MDNGMTITTEHSTHPDLDFNDEIYRELNRICASLSQQCSTYQPEFRTCLD
AAFQALRGGKLIRPRMLLGLYNTLVDDDIEVKLNTVLQVAVALELLHFSL
LVHDDVIDGDLYRRGKLNFIGQILMHRTPESFAQIQRDPEHLDWAQSNGL LMGNLFLAATHQIFARLDLPHHQRVRLLDLLNHTINDTIVGEFLDVGLSS
KAISPNMDIALEMSRLKTATYTFELPMRAAAILAELPQEIETKIGEIGTN
LGIAYQLQDDYLSTFGDAAEHGKDAFSDLREGKETTIIAFARDTAKWTDI
QDNFGSADLSTSQAERIQHLLIQCGAKNHSLNAISDHLNICRSMIKTLSP
QVDPKAQNLLLKQVEQLASRKS SEQ ID NO: 32—a crtB encoding nucleic acid
sequence from C. glutamicum (a crtB-gene)
atgacacaccaaaattcgcctctcttccttaaaagtgcactgagacttta
caatcgggcctcattcaaggcttcacataaagtgatcgaagaatattcga
cgagcttcagtctgtctacgtggttgctatcccacgcatacgaaatgac
atacgaaatctctatgcagtagttcgtatcgccgatgagattgtcgacgg
cactgcacatgccgctggttgctcaactgccaaaatcgaagagattctcg
atgcctatgaaattgcggtcgcattgcagcaccacaacaacgcttcaacaca
gatcttgttttacaagcttatggtgaaactgcccgacgctgtgatttcga
acaagagcatgtaatagccttcttgcatcaatgcgtaaggacctcaaag
ctaatacacacgacccagatagcttcacaacgtatgtctatggctccgcg
gaagttataggcctgcttttgtctcagcgttttcaaccaaggtagaacgat
tagcaaaaaacggctagagattatgcaaaacggagcccgctcattgggag
cggcattccagaaaattaactttctccgtgacttggcagaagatcagcaa
aatttgggccgattttatttccccaaaaccagccaaggaactcttactaa
agaacaaaaagaagatctcatcgctgatatccgtcaagacctagcaattg
cccacgatgcatttccagaaataccagtgcaggctcgcatcggagtgatc
tctgcttatttgctcttttcaaaaactcactgaccgaattgaggctactcc
taccgccgatttattgcgggagcgaatcagagttccacttcatatcaaac
tctctacactcgctagagccacgatgaaaggtctatctatgagcatctac
agaaagaattcgtga SEQ ID NO: 33—a crtB-protein from C. glutamicum
(a crtB-protein)
MTHQNSPLFLKSALRLYNRASFKASHKVIEEYSTSFSLSTWLLSPRIRND
IRNLYAVVRIADEIVDGTAHAAGCSTAKIEEILDAYEIAVLAAPQQRFNT
DLVLQAYGETARRCDFEQEHVIAFFASMRKDLKANTHDPDSFTTYVYGSA
EVIGLLCLSVFNQGRTISKKRLEIMQNGARSLGAAFQKINFLRDLAEDQQ
NLGRFYFPKTSQGTLTKEQKEDLIADIRQDLAIAHDAFPEIPVQARIGVI
SAYLLFQKLTDRIEATPTADLLRERIRVPLHIKLSTLARATMKGLSMSIY
RKNS SEQ ID NO: 34—a crtI encoding nucleic acid
sequence from C. glutamicum (a crtI-gene)
gtgatgaaggtctcgactaaaactccacgctcctcaggtaccgccgtagt
cataggcgcaggtgttgctggtttagccacttctgcacttttagcacgtg
atggctggcaagtaactgttttggaaaaaaatactgatgtcggtggacga
gctggatcgcttgaaatatcaggctttcctggcttctcgatgggataccgg
accttcttggtacctcatgcccgaggcctttgaccatttcttcgcactttt
tggtgcatgtacttctgattatctcgatttggtagaattaacgcctggt
tatcgagttttttctggcacacatgacgctgtcgatgtccccactgaggtg
tgaagaagcaattgcgctattcgaatccatcgaacccggcgcgggtgcaa
aactaggaaattatcttgatagcgcggcagacgcctatgacattgccatt
gatagattccttttataataatttctccacgttaggcccgctgcttcaccg
ggatgtactgacccgagctggccgactgttttctctactgacccgttctt
tacaaaagtacgtaaatagtcaattcagtagcccggtgttgcgccagatc
ctaacctatccagcagtcttcctgtcttcccgacccactactaccccatc
gatgtaccacttgatgagtcataccgatttggtgcagggagtgaaataacc
ctataggtggttttactgcagtggttaacgctgcatcagttagcgctg
gaaaacgggggttgagtttcaactcgattctgaggtcatttccatcaacac
tgcttcatcgaggggcaacacaagcgccacaggtgtgagcttgcttcaca
acagaaaagtgcaaaatctagatgcggatcttgtggtcagcaggcgacc
tacaccatacagaaaattcgcttccgggaacttcgaacctatccc
gaacgatattggtccaatcgcaatcctggaattggagcggtattaatcct
cctgggcgtaaaaggagagttaccccagctcgaccatcacaacctttct
tcagtgaagattggacagatgattttgctgtagttttcgacgggcctcaa
cttaccgccccccacaatgcatcaaattccatttatgtctccaagccttc
aacgtccgaagacggcgttgcacctgctgcaggatacgaaaaccttttgtt
taattccgaccaaggcctctagcagcatcggccacgtgatgcgtatatg
cagtcggcttcagcatccgtggaaacaatcgcgtcacatgcaatcaatca
aattgctacgcaagccggcatccctgacctcactgaccgaattgtggtca
aacgcaccattggccctgcggattttgagcaccgctaccattcatgggta
ggcagtgcgctgggtccagcacatacctcagacagtccgcttttcttaag
agggcgcaatagctccccgcaaggtcaataacctcttctattccggtgcca
ccaccgtcccgggtgtaggaataccatgtgtttaattctgccgagaat
attattaagcgtttacatgccgataccagtgcaggaccactgcccgaacc
attgccgcctaaaacgacaccatctcaaaagacctcatacgatcattaa SEQ ID NO: 35—a crtI-protein from C. glutamicum
(a crtI-protein)
MMKVSTKTPRSSGTAVVIGAGVAGLATSALLARDGWQVTVLEKNTDVGGR
AGSLEISGFPGFRWDTGPSWYLMPEAFDHFFALFGACTSDYLDLVELTPG
YRVFSGTHDAVDVPTGREEAIALFESIEPGAGAKLGNYLDSAADAYDIAI DRFLYNNFSTLGPLLHRDVLTRAGRLFSLLTRSLQKYVNSQFSSPVLRQI
LTYPAVFLSSRPTTTPSMYHLMSHTDLVQGVKYPIGGFTAVVNALHQLAL
ENGVEFQLDSEVISINTASSRGNTSATGVSLLHNRKVQNLDADLVVSAGD
LHHTENNLLPRELRTYPERYWSNRNPGIGAVLILLGVKGELPQLDHHNLF
FSEDWTDDFAVVFDGPQLTRPHNASNSIYVSKPSTSEDGVAPAGYENLFV
LIPTKASSSIGHGDAYMQSASASVETIASHAINQIATQAGIPDLTDRIVV
KRTIGPADFEHRYHSWVGSALGPAHTLRQSAFLRGRNSSRKVNNLFYSGA
TTVPGVGIPMCLISAENIIKRLHADTSAGPLPEPLPPKTTPSQKTSYDH SEQ ID NO: 36—an artificial operon Ptuf-crtEBI
TGGCCGTTACCCTGCGAATGTCCACAGGGTAGCTGGTAGTTTGAAAATCA
ACGCCGTTGCCCTTAGGATTCAGTAACTGGCACATTTTGTAATGCGCTAG
ATCTGTGTGCTCAGTCTTCCAGGCTGCTTATCACAGTGAAAGCAAAACCA
ATTCGTGGCTGCGAAAGTCGTAGCCACCACGAAGTCCAGGAGGACATACA
ATGGACAATGGCATGACAATCACCACAGAACATTCAACTCATCCTGATCT
TGATTTCAATGATGAGATTTATCGGGAACTAAACCGCATCTGCGCTTCGC
TATCTCAACAGTGCAGCACATATCAACCAGAGTTCCGTACCTGCCTAGAT
GCTGCTTTCCAAGCTTTGCGAGGTGGCAAGTTAATCCGCCCTCGAATGCT
ACTGGGCTATACAACACGCTTGTAGACGATGACATTGAGGTCAAACTCA
ACACCGTTTTACAGGTAGCAGTGGCTTTAGAACTACTGCATTTTTCCCTT
TTGGTTCATGACGATGTTATTGACGGAGACCTCTATCGCCGAGGCAAACT
TAATTTTATTGGGCAGATTTCTATGCATCGCACACCTGAAAGTTTTGCAC
AAATCCAGCGCGATCCAGAGCATCTAGATTGGGCACAATCTAATGGACTG
CTTATGGGAAATCTTTTTCTTGCTGCCACCCATCAAATCTTCGCGCGCCT
TGACCTTCCACATCACCAACGGGTTCGACTTTTAGATTTACTCAACCACA
CGATAAATGACCATTATTGTGGGTGGTTCTTGATGTGGGATTAAGCAGC
AAAGCCATCAGCCCCAATATGGACATTGCTCTAGAAATGAGTCGGCTAAA
AACAGCCACATACACTTTTGAACTTCCAATGAGAGCAGCGGCAATTCTCG
CGGAACTACCTCAGGAGATTGAAACAAAGATAGGTGAGATAGGCACAAAC
TTGGGCATCGCTTATCAATTGCAGGACGATTACTTATCTACTTTTGGTGA
CGCAGCCGAACACGGCAAAGATGCCTTTTCTGACCTTCGAGAAGGAAAAG
AAACTACAATTATCGCCTTCGCTCGAGATACTGCTAAATGGACTGATATT
CAAGACAACTTCGGCTCCGCAGATCTGAGCACCTCTCAGGCAGAGCGAAT
TCAACATCTTCTCATACAGTGTGGAGCAAAGAATCACTCCTTGAATGCCA
TCTCCGACCACTTAAATATCTGCCGTTCGATGATCAAAACATAAGCCCC
CAGGTAGATCCCAAGGCTCAAAATTTATTACTTAAACAAGTTGAGCAACT
AGCCAGCCGCAAATCTTAGCTGCAGGTCGACTCTAGAGGATCCGAAAGGA
GGCCCTTCAGATGACACACCAAAATTCGCCTCTCTTCCTTAAAAGTGCAC
TGAGACTTTACAATCGGGCCTCATTCAAGGCTTCACATAAAGTGATCGAA
GAATATTCGACGAGCTTCAGTCTGTCTACGTGGTTGCTATCCCCACGCAT
ACGAAATGACATACGAAATCTCTATGCAGTAGTTCGTATCGCCGATGAGA
TTGTCGACGGCACTGCACATGCCGCTGGTTGCTCAACTGCCAAAATCGAA
GAGATTCTCGATGCCTATGAAATTGCGGTTCTTGCAGCACCACAACAACG
CTTCAACACAGATCTTGTTTTACAAGCTTATGGTGAAACTGCCCGACGCT
GTGATTTCGAACAAGAGCATGTAATAGCCTTCTTTGCATCAATGCGTAAG
GACCTCAAAGCTAATACACACGACCCAGATAGCTTCACAACGTATGTCTA
TGGCTCCGCGGAAGTTATAGGCCTGCTTTGTCTCAGCGTTTTCAACCAAG
GTAGAACGATTAGCAAAAAACGGCTAGAGATTATGCAAAACGGAGCCCGC
TCATTGGGAGCGGCATTCCAGAAAATTAACTTTCTCCGTGACTTGGCAGA
AGATCAGCAAAATTTGGGCCGATTTTATTTCCCCAAAACCAGCCAAGGAA
CTCTTACTAAAGAACAAAAAGAAGATCTCATCGCTGATATCCGTCAAGAC
CTAGCAATTGCCCACGATGCATTTCCAGAAATACCAGTGCAGGCTCGCAT
CGGAGTGATCTCTGCTTATTTGCTCTTTCAAAAACTCACTGACCGAATTG
AGGCTACTCCTACCGCCGATTTATTGCGGGAGCGAATCAGAGTTCCACTT
CATATCAAACTCTACACTCGCTAGAGCCACGATGAAAGGTCTATCTATGT
AGCATCTACAGAAAGAATTCGTGATGAAGGTCTCGACTAAAACTCCACG
CTCCTCAGGTACCGCCGTAGTCATAGGCGCAGGTGTTGCTGGTTTAGCCA
CTTCTGCACTTTTAGCACGTGATGGCTGGCAAGTAACTGTTTTGGAAAAA
AATACTGATGTCGGTGGACGAGCTGGTTCGCTTGAAATATCAGGCTTTCC
TGGCTTTCGATGGGATACCGGACCTTCTTGGTACCTCATGCCCGAGGCCT
TTGACCATTTCTTCGCACTTTTTGGTGCATGTACTTCTGATTATCTCGAT
TTGGTAGAATTAACGCCTGGTTATCGAGTTTTTTCTGGCACACATGACGC
TGTCGATGTCCCCACTGGGCGTGAAGAAGCAATTGCGCTATTCGAATCCA
TCGAACCCGGCGCGGGTGCAAAATAGGAAATTATCTTGATAGCGCGGCA
GACGCCTATGACATTGCCATTGATAGATTCCTTTATAATAATTTCTCCAC
GTTAGGCCCGCTGCTTCACCGGGATGTACTGACCCGAGCTGGCCGACTGT
TTTCTCTACTGACCCGTTCTTTACAAAAGTACGTAAATAGTCAATTCAGT
AGCCCGGTGTTGCGCCAGATCCTAACCTATCCAGCAGTCTTCCTGTCTTC
CCGACCCACTACTACCCCATCTGATGAGTCATACGATT
GGTGCAGGGAGTGAAATACCCTATAGGTGGTTTTACTGCAGTGGTTAAC
GCTCTGCATCAGTTAGCGCTGGAAAACGGGGTTGAGTTTCAACTCGATTC
TGAGGTCATTTCCATCAACACTGCTTCATCGAGGGGCAACACAAGCGCCA
CAGGTGTGAGCTTGCTTCACAACAGAAAAGTGCAAAATCTAGATGCAGAT
CTTGTGGTTCAGCAGGCGACCTACACCATACAGAAAATAATCTGCTTCC
CCGGGAACTTCGAACCTATCCCGAACGATATTGGTCCAATCGCAATCCTG
GAATTGGAGCGGTATTAATCCTCCTGGGCGTAAAAGGAGAGTTACCCCAG
CTCGACCATCACAACCTTTTCTTCAGTGAAGATTGGACAGATGATTTTGC
TGTAGTTTTCGACGGGCCTCAACTTACCCGCCCCCACAATGCATCAAATT
CCATTTATGTCTCCAAGCCTTCAACGTCCGAAGACGGCGTTGCACCTGCT

```
GGATACGAAAACCTTTTTGTTTTAATTCCGACCAAGGCCTCTAGCAGCAT
CGGCCACGGTGATGCGTATATGCAGTCGGCTTCAGCATCCGTGGAAACAA
TCGCGTCACATGCAATCAATCAAATTGCTACGCAAGCCGGCATCCCTGAC
CTCACTGACCGAATTGTGGTCAAACGCACCATTGGCCCTGCGGATTTTGA
GCACCGCTACCATTCATGGGTAGGCAGTGCGCTGGGTCCAGCACATACCG
TCAGACAGTCCGCTTTCTTAAGAGGGCGCAATAGCTCCCGCAAGGTCAAT
AACCTCTTCTATTCCGGTGCCACCACCGTCCCGGGTGTAGGAATACCCAT
GTGTTTAATTTCTGCCGAGAATATTATTAAGCGTTTACATGCCGATACCA
GTGCAGGACCACTGCCCGAACCATTGCCGCCTAAAACGACACCATCTCAA
AAGACCTCATACGATCATTAA
```

SEQ ID NO: 37—a crtR encoding nucleic acid
sequence from *C. glutamicum* (a crtR-gene)
```
ATGCTGAATATGCAGGAACCAGATAAAATCCATCCGGCAGAACCTACACT
TCGTAATATTTATGACGTTAAAACTAGTGATCCCAAAAGTGAATTAGTTG
ATCGTTCTGGCATGTCGGAAGAAGACATTGCGCAAATTGGGCGGCTAATG
AAATCGTTGGCCAGTCTTCGCGATGTGGAACGTAGTATTGGTGAAGCCTC
GGCCACGTTATATGGAGCTAAGTACCTCGATATGCGAGCTTTGCACTATT
TGATTGTGGCGGGCAATGCGGGCGAAGTGGTGACTCCAGGAATGCTTGGA
GCTCACCTTAAGCTTTCCCCGGCATCTGTAACAAAGACGCTTAATAGGCT
AGAAAAAGGTGGGCATATTGTTCGTAATGTGCACCCCGTCGACCGCAGGG
CTTTCGCCCTCATGGTCACTGATGCCACTCGTGGAGAGGCGATGCGGACG
CTTGGTAAGCATCAGGCGCGTCGTTTTGATGCTGCTAAACGATTAACTCC
ACAAGAGCGTGAAGTGGTTATCCGATTCCTTCAGGATATGGCACAGGAGT
TATCCCTTAATAATGCACCATGGCTCAACACGGAGTAG
```

SEQ ID NO: 38—a crtR-protein from *C. glutamicum*
(a crtR-protein)
```
MLNMQEPDKIHPAEPTLRNIYDVKTSDPKSELVDRSGMSEEDIAQIGRLM
KSLASLRDVERSIGEASARYMELSAPDMRALHYLIVAGNAGEVVTPGMLG
AHLKLSPASVTKTLNRLEKGGHIVRNVHPVDRRAFALMVTDATRGEAMRT
LGKHQARRFDAAKRLTPQEREVVIRFLQDMAQELSLNNAPWLNTE
```

SEQ ID NO: 39—a crtY$_{Pa}$ encoding nucleic acid
sequence from *P. ananatis* (a crtY-gene)
```
ATGCAACCGCATTATGATCTGATTCTCGTGGGGGCTGGACTCGCGAATGG
CCTTATCGCCCTGCGTCTTCAGCAGCAGCAACCTGATATGCGTATTTTGC
TTATCGACGCCGCACCCCAGGCGGGCGGGAATCATACGTGGTCATTTCAC
CACGATGATTTGACTGAGAGCCAACATCGTTGGATAGCTTCGCTGGTGGT
TCATCACTGGCCCGACTATCAGGTACGCTTTCCCACACGCCGTCGTAAGC
TGAACAGCGGCTACTTCTGTATTACTTCTCAGCGTTTCGCTGAGGTTTTA
CAGCGACAGTTTGGCCCGCACTTGTGGATGGATACCGCGGTCGCAGAGGT
TAATGCGGAATCTGTTCGGTTGAAAAAGGGTCAGGTTATCGGTGCCCGCG
CGGTGATTGACGGGCGGGGTTATGCGGCAAACTCAGCACTGAGCGTGGGC
TTCCAGGCGTTTATTGGCCAGGAATGGCGATTGAGCCACCCGCATGGTTT
ATCGTCTCCCATTATCATGGATGCCACGGTCGATCAGCAAAATGGTTATC
GCTTCGTGTACAGCCTGCCGCTCTCGCCGACCAGATTGTTAATTGAAGAC
ACGCACTATATCGATAATGCGACATTAGATCCTGAACGCGCGCGGCAAAA
TATTTGCGACTATGCCGCGCAACAGGGTTGGCAGCTTCAGACATTGCTGC
GTGAAGAACAGGGCGCCTTACCCATCACCCTGTCGGGCAATGCCGAGGCA
TTCTGGCAGCAGCGCCCCCTGGCCTGTAGTGGATTACGTGCCGGTCTGTT
CCATCCTACCACCGGCTATTCACTGCCGCTGGCGGTTGCCGTGGCCGACC
GCCTGAGCGCACTTGATGTCTTTACGTCGGCCTCAATTCACCAGGCTATT
AGGCATTTTGCCCGCGAGCGCTGGCAGCAGCAGCGCTTTTTCCGCATGCT
GAATGCATGCTGTTTTTAGCCGGACCCGCCGATTCACGCTGGCGGGTTA
TGCAGCGTTTTTATGGTTTACCTGAAGATTTAATTGCCCGTTTTTATGCG
GGAAAACTCACGCTGACCGATCGGCTACGTATTCTGAGCGGCAAGCCGCT
GTTCCGGTATTAGCAGCATTGCAAGCCATTATGACGACTCATCGTTAA
```

SEQ ID NO: 40—Ptuf-crtY encoding nucleic acid
sequence (*Pantoea ananatis*)
```
TGGCCGTTACCCTGCGAATGTCCACAGGGTAGCTGGTAGTTTGAAAATCA
ACGCCGTTGCCCTTAGGATTCAGTAACTGGCACATTTTGTAATGCGCTAG
ATCTGTGTGCTCAGTCTTCCAGGCTGCTTATCACAGTGAAAGCAAAACCA
ATTCGTGGCTGCGAAAGTCGTAGCCACCACGAAGTCCAGGAGGACATACA
AAGCTTGCATGCCTGCAGGTCGACTCTAGAGGAAAGGAGGCCCTTCAGAT
GCAACCGCATTATGATCTGATTCTCGTGGGGGCTGGACTCGCGAATGGCC
TTATCGCCCTGCGTCTTCAGCAGCAGCAACCTGATATGCGTATTTTGCTT
ATCGACGCCGCACCCCAGGCGGGCGGGAATCATACGTGGTCATTTCACCA
CGATGATTTGACTGAGAGCCAACATCGTTGGATAGCTTCGCTGGTGGTTC
ATCACTGGCCCGACTATCAGGTACGCTTTCCCACACGCCGTCGTAAGCTG
AACAGCGGCTACTTCTGTATTACTTCTCAGCGTTTCGCTGAGGTTTTACA
GCGACAGTTTGGCCCGCACTTGTGGATGGATACCGCGGTCGCAGAGGTTA
ATGCGGAATCTGTTCGGTTGAAAAAGGGTCAGGTTATCGGTGCCCGCGCG
GTGATTGACGGGCGGGGTTATGCGGCAAACTCAGCACTGAGCGTGGGCTT
CCAGGCGTTTATTGGCCAGGAATGGCGATTGAGCCACCCGCATGGTTTAT
CGTCTCCCATTATCATGGATGCCACGGTCGATCAGCAAAATGGTTATCGC
TTCGTGTACAGCCTGCCGCTCTCGCCGACCAGATTGTTAATTGAAGACAC
GCACTATATCGATAATGCGACATTAGATCCTGAACGCGCGCGGCAAAATA
```

```
TTTGCGACTATGCCGCGCAACAGGGTTGGCAGCTTCAGACATTGCTGCGT
GAAGAACAGGGCGCCTTACCCATCACCCTGTCGGGCAATGCCGAGGCATT
CTGGCAGCAGCGCCCCCTGGCCTGTAGTGGATTACGTGCCGGTCTGTTCC
ATCCTACCACCGGCTATTCACTGCCGCTGGCGGTTGCCGTGGCCGACCGC
CTGAGCGCACTTGATGTCTTTACGTCGGCCTCAATTCACCAGGCTATTAG
GCATTTTGCCCGCGAGCGCTGGCAGCAGCAGCGCTTTTTCCGCATGCTGA
ATGCATGCTGTTTTTAGCCGGACCCGCCGATTCACGCTGGCGGGTTATG
CAGCGTTTTTATGGTTTACCTGAAGATTTAATTGCCCGTTTTTATGCGGG
AAAACTCACGCTGACCGATCGGCTACGTATTCTGAGCGGCAAGCCGCTG
TTCCGGTATTAGCAGCATTGCAAGCCATTATGACGACTCATCGTTAA
```

| | Name | Sequence 5' → 3' |
|---|---|---|
| SEQ ID NO.: 41 | cg0725_E | GCGCGAAGATTTGATGGG |
| SEQ ID NO.: 42 | cg0725_F | ACTTGTCACCACAGCACT AC |
| SEQ ID NO.: 43 | NW29 Op1-E | TCGCACCATCTACGACAA CC |
| SEQ ID NO.: 44 | NW30 Op1-F | CTACGAAGCTGACGCCGA AG |
| SEQ ID NO.: 45 | crtE-B | CCCATCCACTAAACTTAA ACAGATTGTCATGCCATT GTCCAT |
| SEQ ID NO.: 46 | crtE-PstI-fw | AAAAACTGCAGGAAAGGAG GCCCTTCAGATGGACAAT GGCATGACAATC |
| SEQ ID NO.: 47 | NW31 Op2-E | GTGGTGCTCGAGAACATA AG |
| SEQ ID NO.: 48 | NW32 Op2-F | CGGTCACCCGTAACAATC AG |
| SEQ ID NO.: 49 | crtY-E | TTGCACCTGCTGGATACG AA |
| SEQ ID NO.: 50 | crtEb-DelF | AAAACAATGCGCAGCGCA |
| SEQ ID NO.: 51 | PD5 (pSH1-fw) | ACCGGCTCCAGATTTATC AG |
| SEQ ID NO.: 52 | 582 (pSH1-rv, pEKEx3-rv) | ATCTTCTCTCATCCGCCA |
| SEQ ID NO.: 53 | pECXT-fw | AATACGCAAACCGCCTCT CC |
| SEQ ID NO.: 54 | pECXT-rv | TACTGCCGCCAGGCAAAT TC |
| SEQ ID NO.: 55 | cg0725_A* | GCAGGTCGACTCTAGAGG ATCCCCGCGCGAAGATTT |
| SEQ ID NO.: 56 | cg0725_D* | GATGGGCCAGTGAATTCG AGCTCGGTACCCCTTGTC ACCACAGCACTACT |
| SEQ ID NO.: 57 | Pa_crtY-fw** | CTGCAGGTCGACTCTAGA GGAAAGGAGGCCCTTCAG ATGCAACCGCATTATGAT CTG |
| SEQ ID NO.: 58 | Pa_crtY-rv1** | CGGTACCCGGGGATCTTA ACGATGAGTCGTCATAAT GG |

*Used for sequencing to confirm deletion of crtR
**Primers were used to amplify crtY$_{Pa}$ SEQ ID NO.: 59—an LdhA (cg3219) encoding nucleic
acid sequence from *C. glutamicum* (an LdhA gene)
```
atgaaagaaaccgtcggtaacaagattgtcctcattggcgcaggagatgt
tggagttgcatacgcatacgcactgatcaaccagggcatggcagatcacc
ttgcgatcatcgacatcgatgaaaagaaactcgaaggcaacgtcatggac
```

-continued

```
ttaaaccatggtgttgtgtgggccgattcccgcaccgcgtcaccaaggg
cacctacgctgactgcgaagacgcagccatggttgtcatttgtgccggcg
cagcccaaaagccaggcgagacccgcctccagctggtggacaaaaacgtc
aagattatgaaatccatcgtcggcgatgtcatggacagcggattcgacgg
catcttcctcgtggcgtccaacccagtggatatcctgacctacgcagtgt
ggaaattctccggcttggaatggaaccgcgtgatcggctccggaactgtc
ctggactccgctcgattccgctacatgctgggcgaactctacgaagtggc
accaagctccgtccacgcctacatcatcggcgaacacggcgacactgaac
ttccagtcctgtcctccgcgaccatcgcaggcgtatcgcttagccgaatg
ctggacaaagaccagagcttgagggccgtctagagaaaattttcgaaga
cacccgcgacgctgcctatcacattatcgacgccaagggctccacttcct
acggcatcggcatgggtcttgctcgcatcacccgcgcaatcctgcagaac
caagacgttgcagtcccagtctctgcactgctccacggtgaatacggtga
ggaagacatctacatcggcaccccagctgtggtgaaccgccgaggcatcc
gccgcgttgtcgaactagaaatcaccgaccacgagatggaacgcttcaag
cattccgcaaatacccctgcgcgaaattcagaagcagttcttctaa
```

SEQ ID NO.: 60—a LdhA-protein from C. glutamicum
MKETVGNKIVLIGAGDVGVAYAYALINQGMADHLAIIDIDEKKLEGNVMD
LNHGVVWADSRTRVTKGTYADCEDAAMVVICAGAAQKPGETRLQLVDKNV
KIMKSIVGDVMDSGFDGIFLVASNPVDILTYAVWKFSGLEWNRVIGSGTV
LDSARFRYMLGELYEVAPSSVHAYIIGEHGDTELPVLSSATIAGVSLSRM
LDKDPELEGRLEKIFEDTRDAAYHIIDAKGSTSYGIGMGLARITRAILQN
QDVAVPVSALLHGEYGEEDIYIGTPAVVNRRGIRRVVELEITDHEMERFK
HSANTLREIQKQFF SEQ ID NO.: 61—a SugR (cg2115) encoding nucleic
acid sequence from C. glutamicum
ATGTACGCAGAGGAGCGCCGTCGACAGATTGCCTCATTAACGGCAGTTGA
GGGACGTGTAAATGTCACAGAATTAGCGGGCCGATTCGATGTCACTGCAG
AGACGATTCGACGAGACCTTGCGGTGCTAGACCGCGAGGGAATTGTTCAC
CGCGTTCACGGTGGCGCAGTAGCCACCCAATCTTTCCAAACCACAGAGTT
GAGCTTGGATACTCGTTTCAGGTCTGCATCGTCAGCAAAGTACTCCATTG
CCAAGGCAGCGATGCAGTTCCTGCCCGCTGAGCATGGCGGACTGTTCCTC
GATGCGGGAACTACTGTTACTGCTTTGGCCGATCTCATTTCTGAGCATCC
TAGCTCCAAGCAGTGGTCGATCGTGACCAACTGCCTCCCCATCGCACTTA
ATCTGGCCAACGCCGGGCTTGATGATGTCCAGCTGCTTGGAGGAAGCGTT
CGCGCGATCACCCAGGCTGTTGTGGGTGACACTGCGCTTCGTACTCTCGC
GCTGATGCGTGCGGATGTAGTGTTCATCGGCACCAACGCGTTGACGTTGG
ATCACGGATTGTCTACGGCCGATTCCCAAGAGGCTGCCATGAAATCTGCG
ATGATCACCAACGCCCACAAGGTGGTGGTGTTGTGTGACTCCACCAAGAT
GGGCACCGACTACCTCGTGAGCTTTGGCGCAATCAGCGATATCGATGTGG
TGGTCACCGATGCGGGTGCACCAGCAAGTTTCGTTGAGCAGTTGCGAGAA
CGCGATGTAGAAGTTGTGATTGCAGAATGA SEQ ID NO.: 62—a SugR— amino acid sequence from
C. glutamicum
MYAEERRRQIASLTAVEGRVNVTELAGRFDVTAETIRRDLAVLDREGIVH
RVHGGAVATQSFQTTELSLDTRFRSASSAKYSIAKAAMQFLPAEHGGLFL
DAGTTVTALADLISEHPSSKQWSIVTNCLPIALNLANAGLDDVQLLGGSV
RAITQAVVGDTALRTLALMRADVVFIGTNALTLDHGLSTADSQEAAMKSA
MITNAHKVVVLCDSTKMGTDYLVSFGAISDIDVVVTDAGAPASFVEQLRE
RDVEVVIAE

FIGURES

FIG. 1: Strain construction. The strain GRLys1ΔsugRΔldhA is the initial strain. Deletions are marked with Δ, integrations are marked with Int. First, genomic changes were carried out by conjugation. Then plasmids were transformed into the cell.

Figure 2:
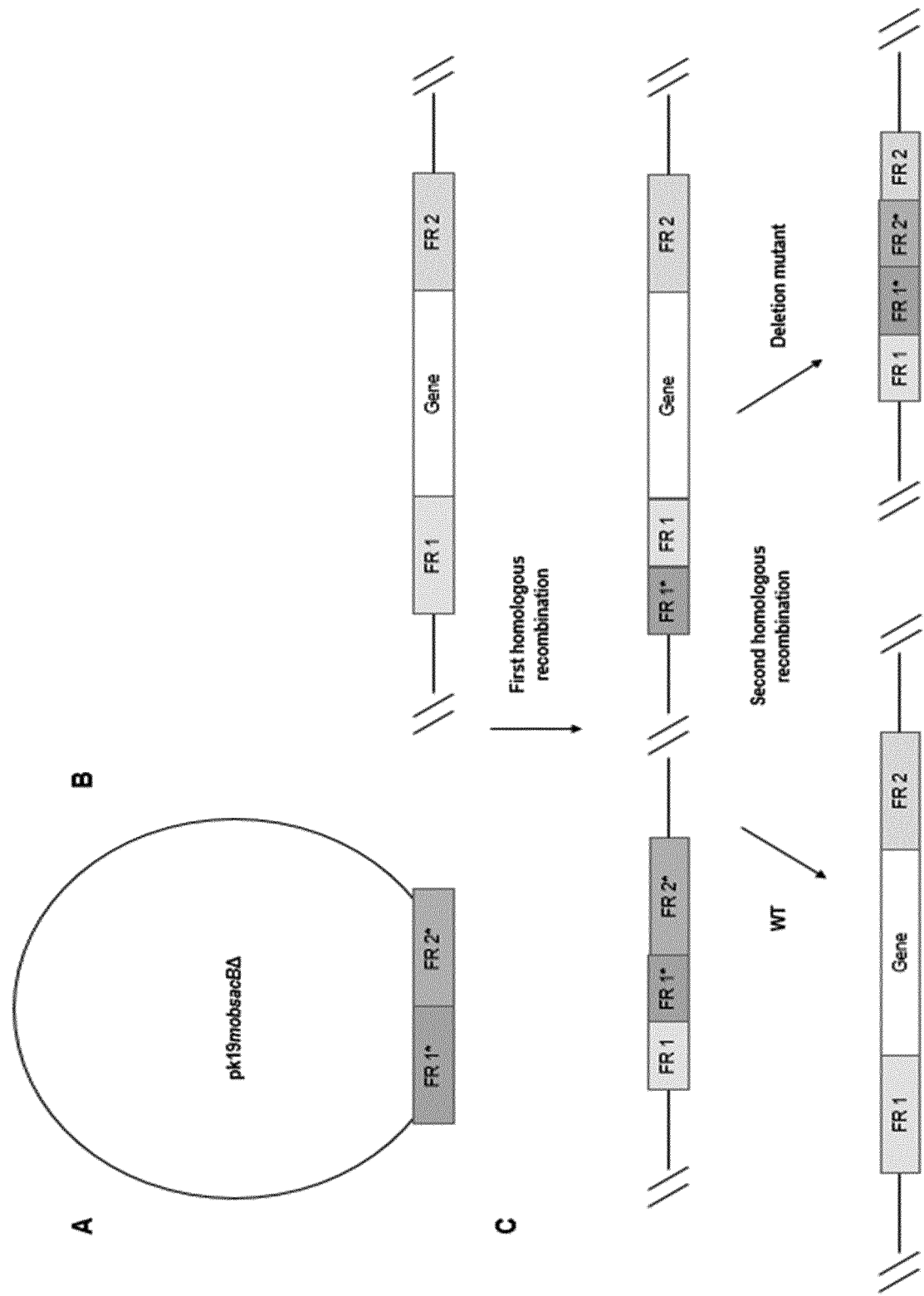

FIG. 2: Deletion of genomic DNA. A) Simplified figure of pk19mobsacB with a deletion construct consisting of FR1 and FR2. B) Genomic region with flanking regions 1 and 2 and the gene which is going to be deleted. C) Conjugation by two homologous recombinations, where the two possible results are shown, the WT (initial genome) and the deletion mutant.

Figure 3:
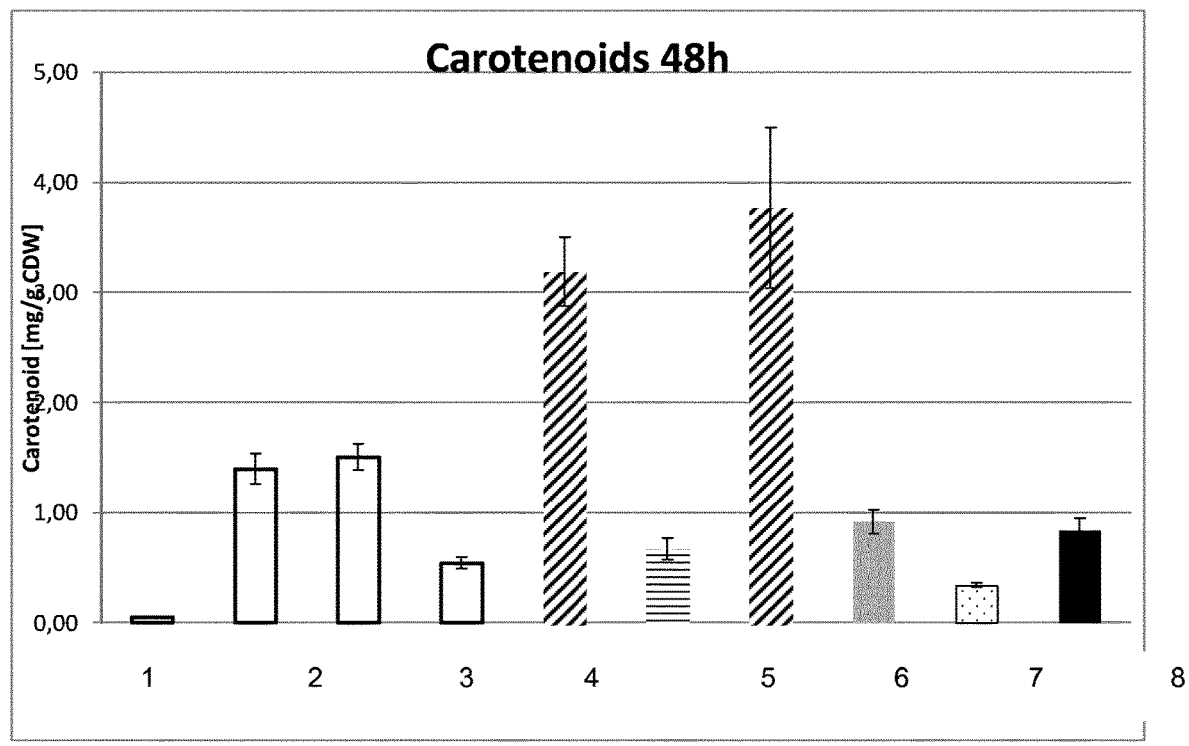

FIG. 3: Carotenoid titers in the various strains after 48 hours of growth. The titers with standard deviation of the produced carotenoids by the various strains were analyzed by HPLC. Significances are calculated with an unpaired two-sided student's t-test, using the carotenoid titer of GRLys1ΔsugRΔldhA as reference (*: $0.01 < p \leq 0.05$; : $0.001 < p \leq 0.01$; *: $p \leq 0.001$). 1=GRLYS1ΔsugRΔldh), 2=DECA LYS1, 3=DECA LYS2 and 4=DECA-BETA LYS produced decaprenoxanthin; 5=DECA-BETA LYS and 7=BETA LYS produced β-carotene; 6=LYC LYS produced lycopene; 8=CAN LYS produced canthaxanthin; 9=ZEA LYS produced zeaxanthin; 10=ASTA LYS produced astaxanthin.

Figure 4:
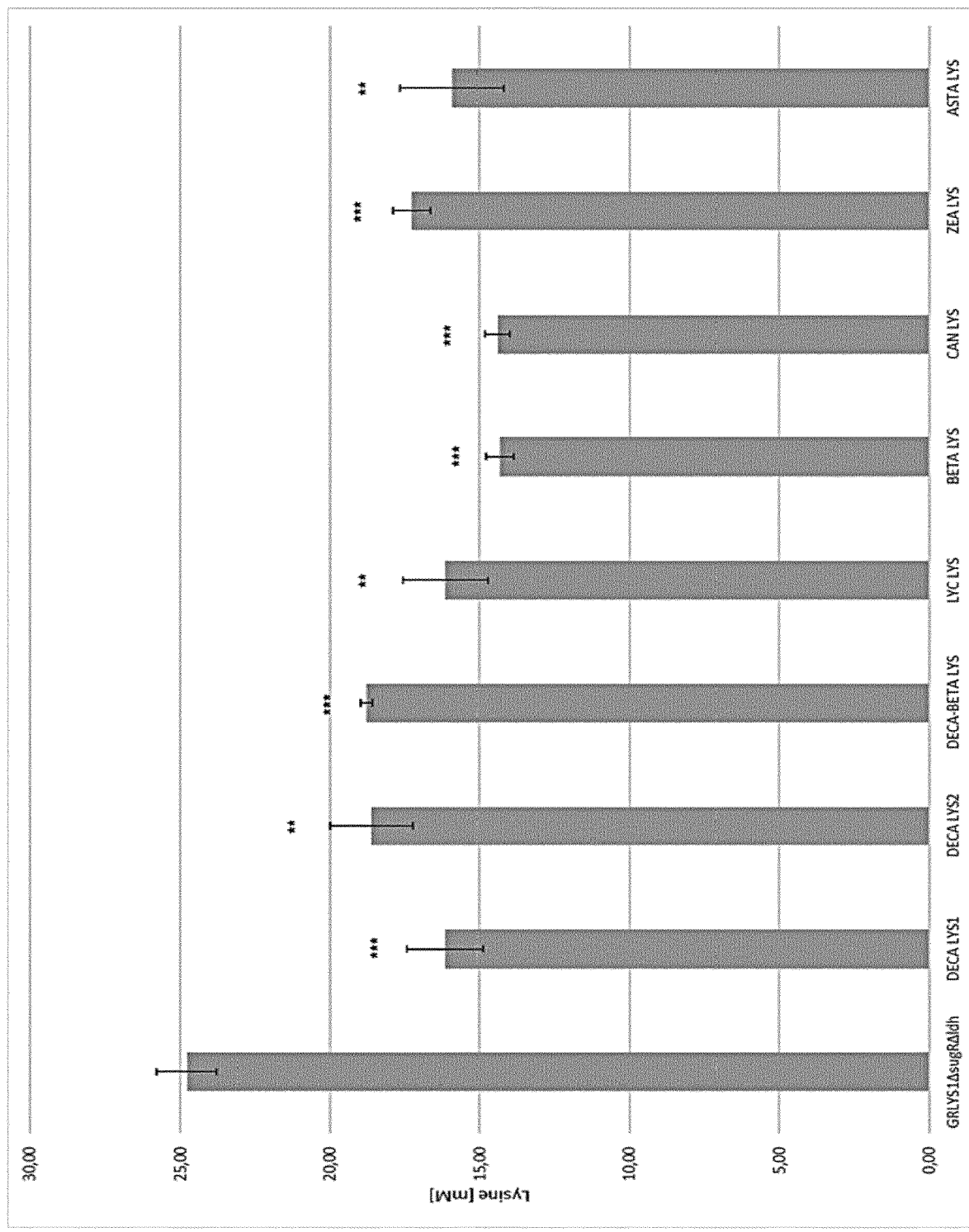

FIG. 4: Titers of lysine in the various strains after 48 hours cultivation. The titers with standard deviation of the produced lysine by the various strains were analyzed by HPLC. Significances are calculated with an unpaired two-sided student's t-test, using the GRLys1ΔsugRΔldhA as reference (*: $0.01 < p \leq 0.05$; : $0.001 < p \leq 0.01$; *: $p \leq 0.001$).

Figure 5:
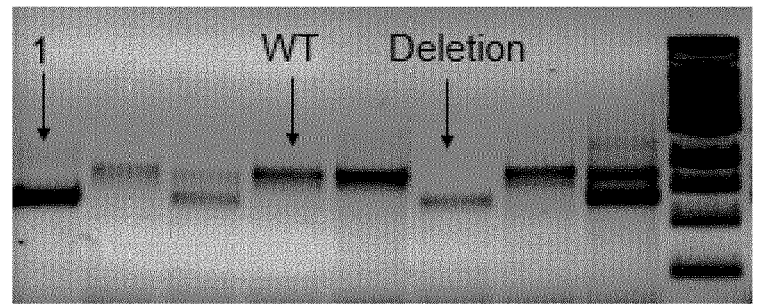
Figure 5:
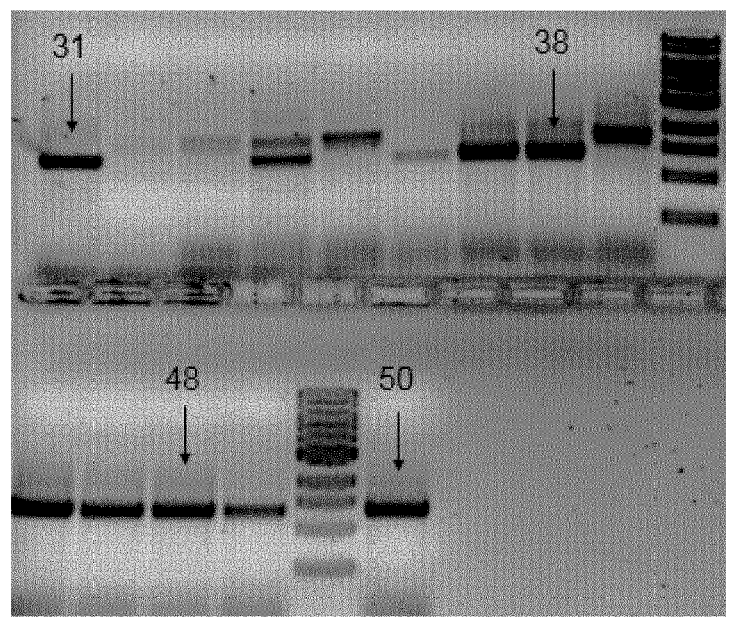
Figure 5:
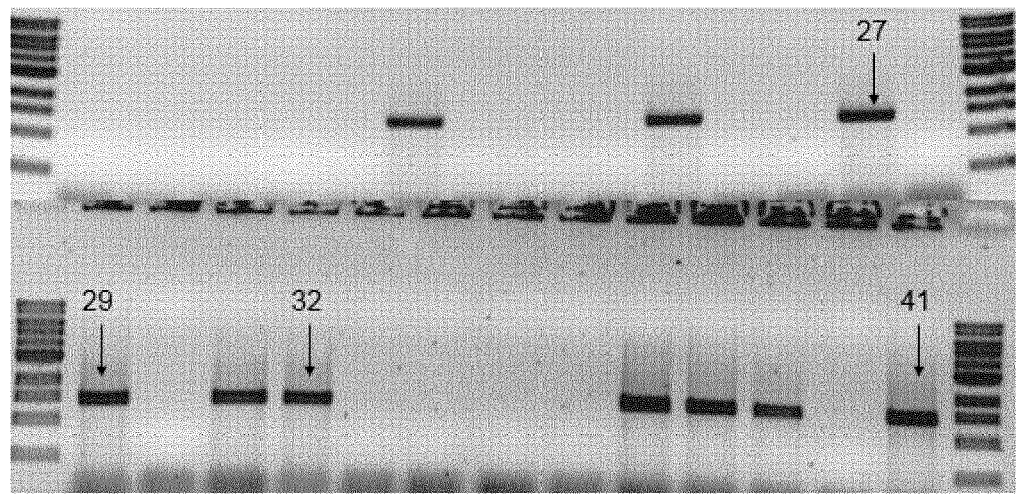
Figure 5:
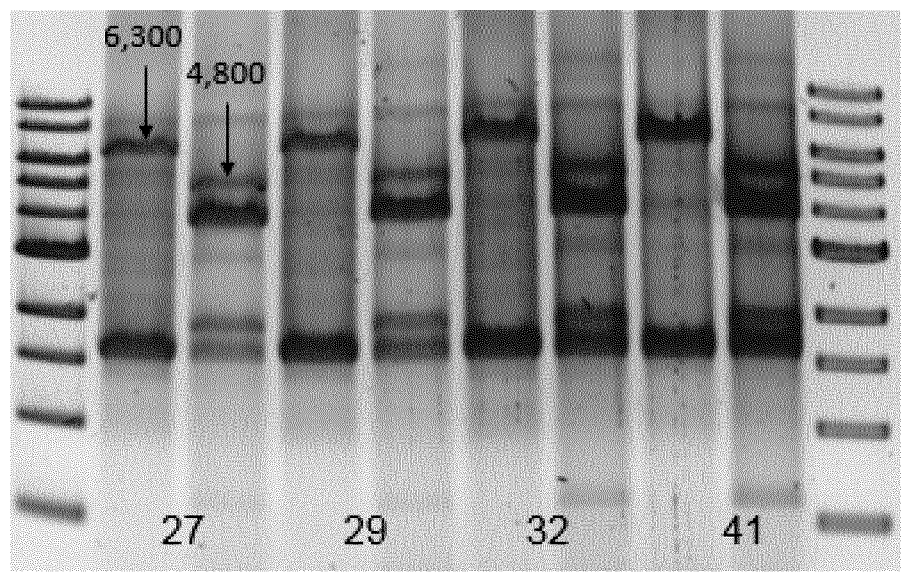
Figure 5:
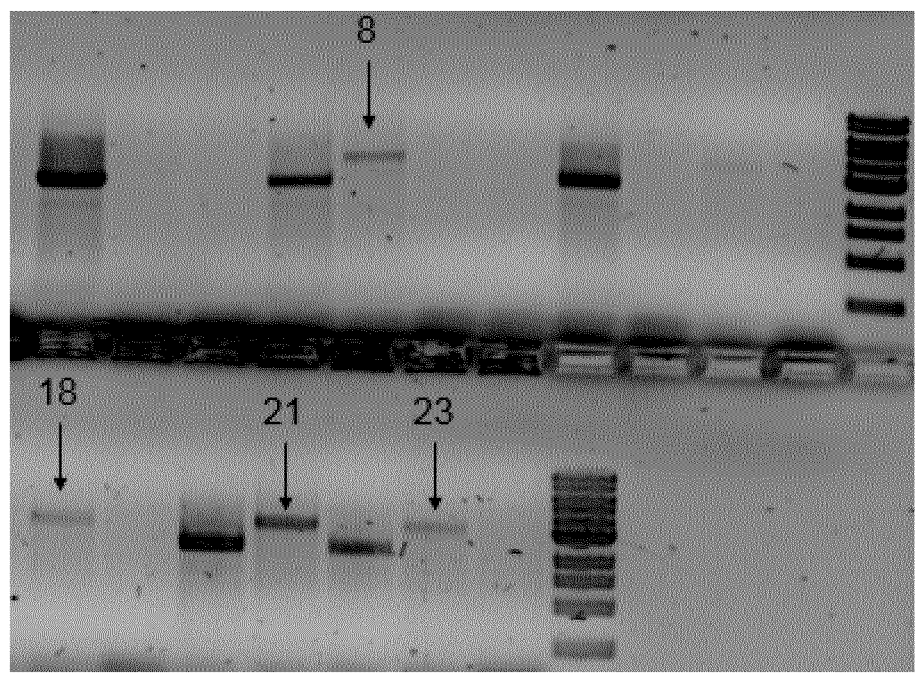
Figure 5:
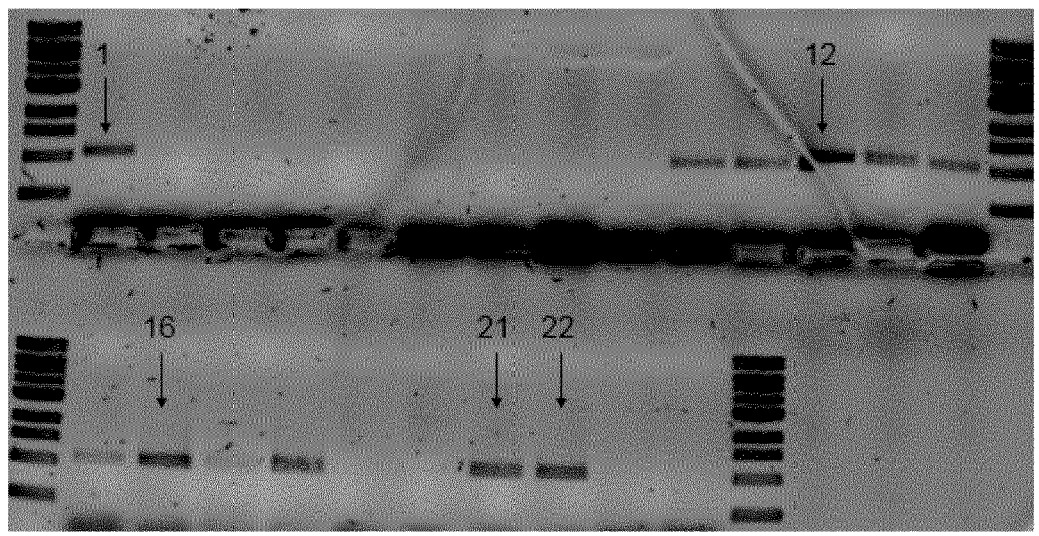
Figure 5:
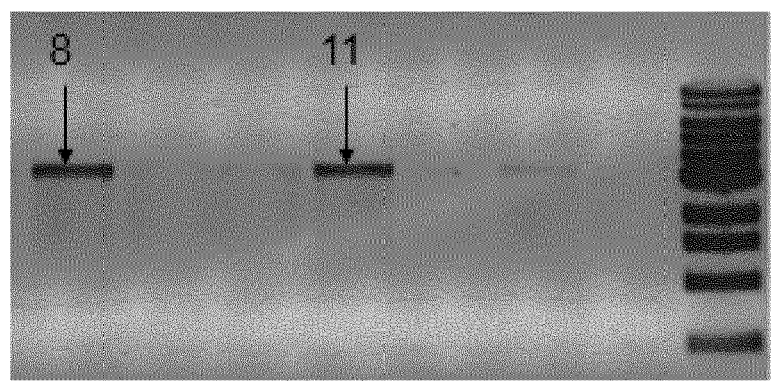
Figure 5:
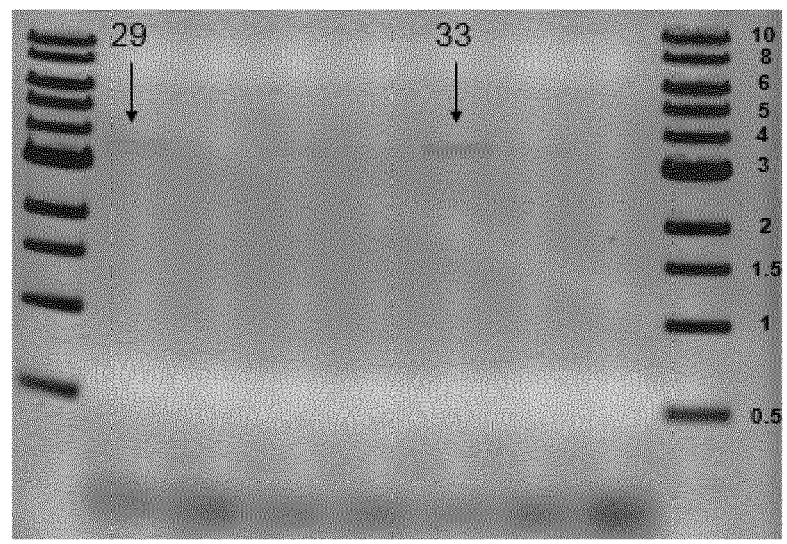
Figure 5:
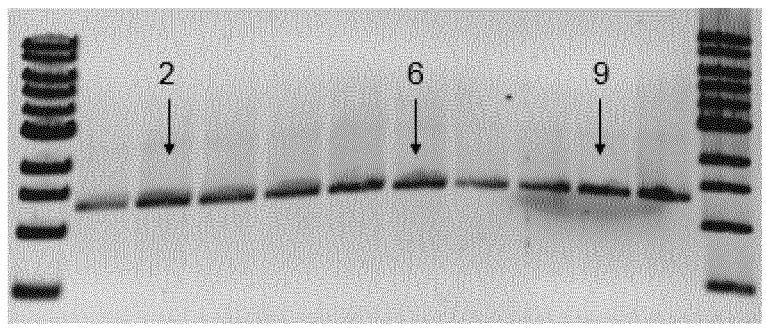
Figure 5:
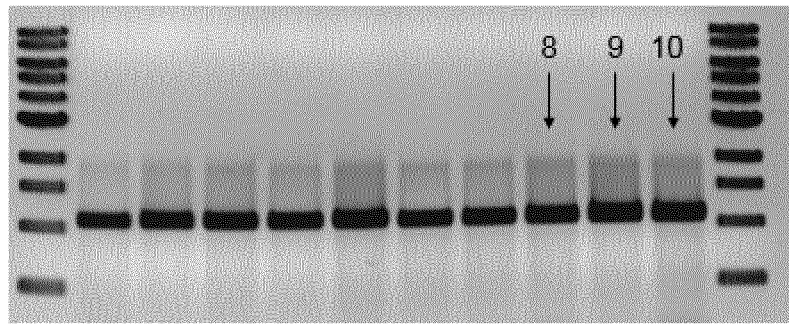
Figure 5:
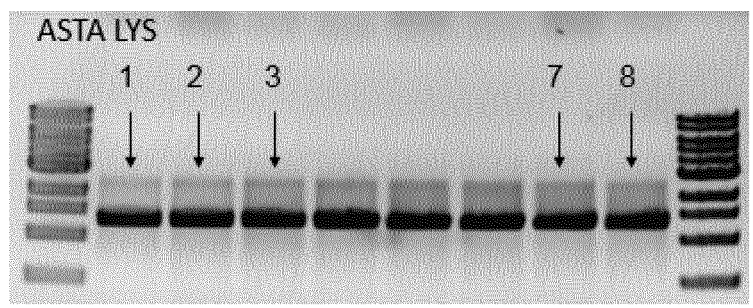

FIG. 5: Colony-PCR of
DECA LYS1 (5 a and b: deletion of crtR),
DECA LYS2 (5 c (primer NW29 OP1-E and crtE-B) and d (primer NW29 OP1-E and NW30 OP1-F): insertion of crtEBI),
DECA BETA LYS (5 e: insertion of crtY$_{Pa}$),
LYC LYS (5 f: deletion of genes crtYe, crtYf and crtEb since they are part of an operon),
BETA LYS (5 g and h: insertion of crt Y$_{Fp}$),
CAN LYS (5 i: insertion of pSH1_crtW1$_{Fp}$),
ZEA LYS (5 j: insertion of pECXT_crtZ$_{Fp}$),
ASTA LYS (5 k: BETALYS (pECXT99a_crtZFp) (pSH1-crtWFp).

Figure 6:
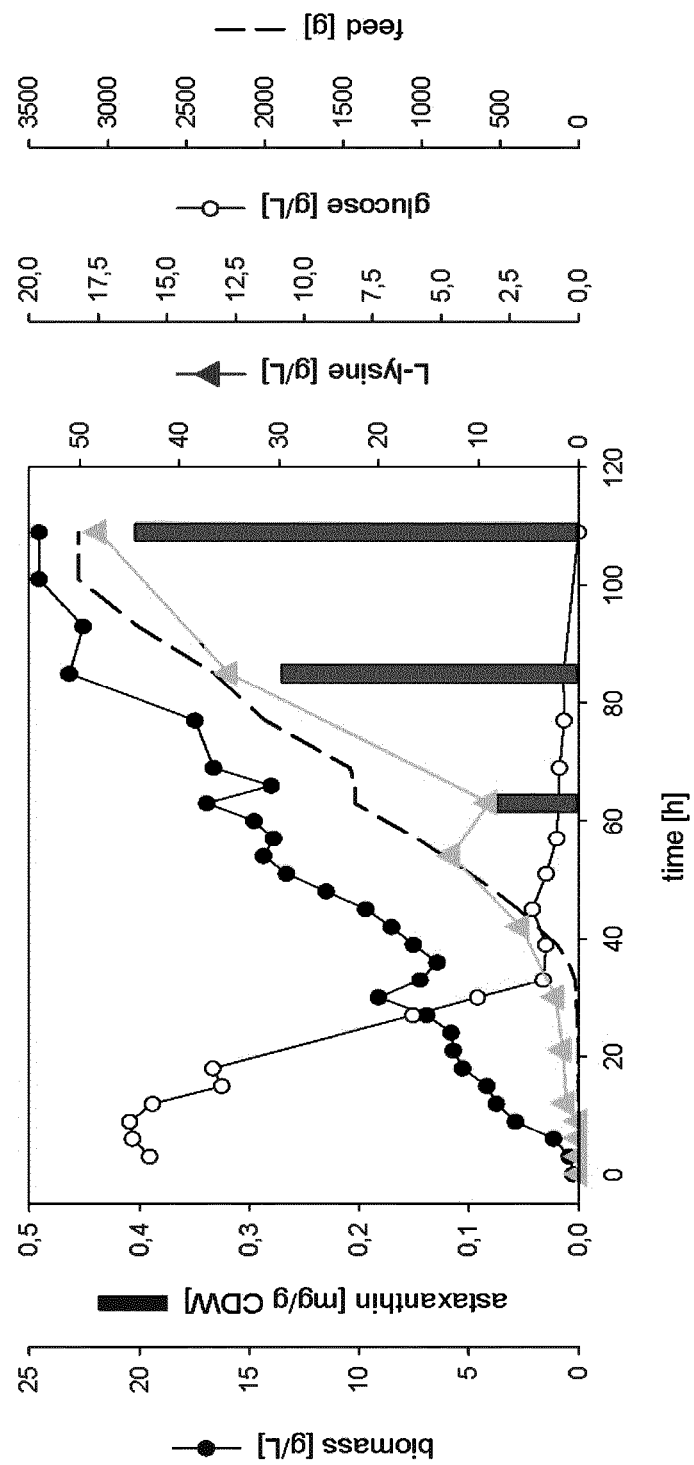

FIG. 6: Fed-batch fermentation of C. glutamicum ASTALYS with glucose as primary carbon source. ASTALYS was fermented in a 20 L fermenter with a starting volume of 12 L and 3 L feeding. Biomass concentrations are indicated with black circles, astaxanthin concentrations with bars, L-lysine concentrations with grey triangles and glucose concentrations with open circles.

Figure 7:
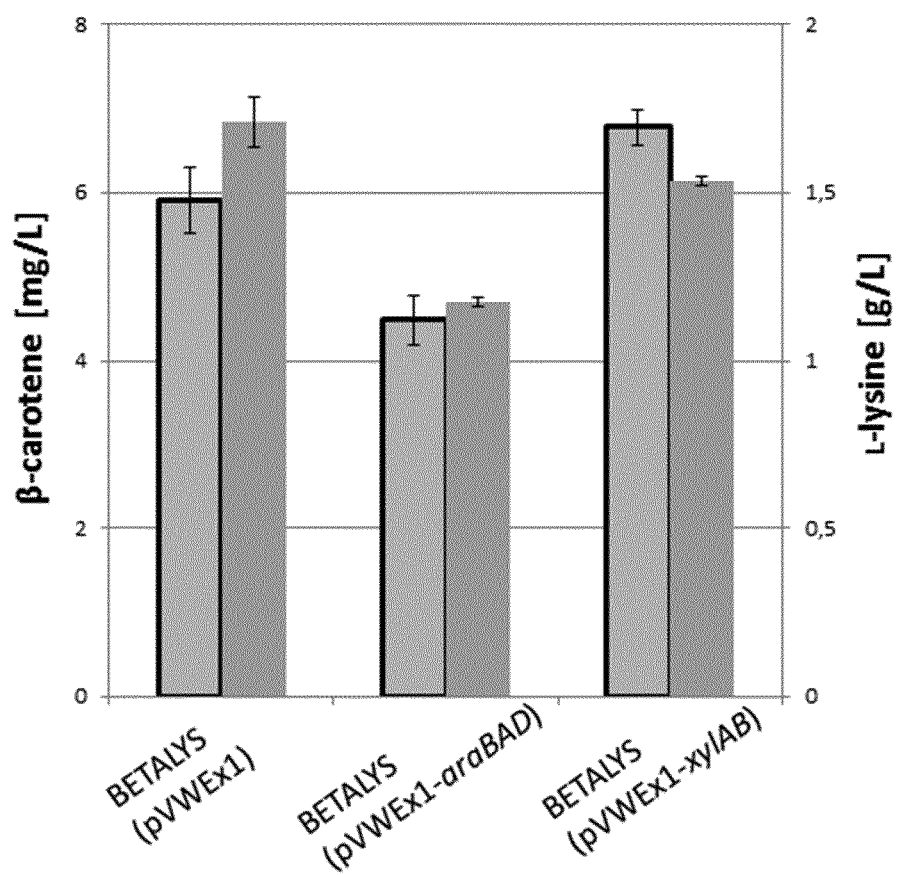

FIG. 7: Coproduction of β-carotene and L-lysine from alternative carbon sources. BETALYS derivatives were grown for 48 h in CGXII supplemented with 10 g/L of the following carbon sources: glucose (BETALYS (pVWEx1)), arabinose (BETALYS (pVWEx1-araBAD)) and xylose (BETALYS (pVWEx1-xylAB)). Titers are given as means of three biological triplicates (exception BETALYS (pVWEx1-xylAB) as duplicate) with standard deviations. Open bars: L-lysine, boxed bars: β-carotene.

DETAILED DESCRIPTION

It was surprisingly found that the use of recombinant C. glutamicum wherein in the genome of said recombinant C. glutamicum crtR, crtYe and crtYf and crtEb were deleted and crtEBI, crtYe, and at least one recombinant sequence which comprises a nucleic acid sequence encoding for a crtZ-protein (crtZ-nucleic acid sequence), preferably from F. pelagi (crtZ$_{Fp}$-nucleic acid sequence), at least one recombinant sequence which comprises a nucleic acid sequence encoding for a crtW-protein (crtW-nucleic acid sequence), preferably from F. pelagi (crtW$_{Fp}$-nucleic acid sequence), B. aurantiaca (crtW$_{Ba}$-nucleic acid sequence) or S. astaxanthinifaciens (crtW$_{Sa}$-nucleic acid sequence) were introduced in a process for the production of astaxanthin and lysine yields not only higher amounts of said substance compared to processes with recombinant C. glutamicum known in the art but also an increased production of lysine.

One aspect of the present invention refers to a recombinant gram-positive bacterium, preferably C. glutamicum, wherein the genome of said bacterium was modified in that it comprises deletions of crtR, crtYe and crtYf from said bacterium, preferably from C. glutamicum, and crtEb, respectively, and introduction of crtEBI, introduction of crtY$_{Pa}$ and introduction of at least one recombinant sequence which comprises a nucleic acid sequence encoding for a crtZ-protein (crtZ-nucleic acid sequence), preferably from *F. pelagi* (crtZ$_{Fp}$-nucleic acid sequence), at least one recombinant sequence which comprises a nucleic acid sequence encoding for a crtW-protein (crtW-nucleic acid sequence), preferably from *F. pelagi* (crtW$_{Fp}$-nucleic acid sequence), *B. aurantiaca* (crtW$_{Ba}$-nucleic acid sequence) or *S. astaxanthinifaciens* (crtW$_{Sa}$-nucleic acid sequence).

In one preferred embodiment, in said recombinant gram-positive bacterium according to the invention, preferably *C. glutamicum*, the genes crtYe, crtYf and crtEb are replaced by said crtZ-nucleic acid sequence, preferably a crtZ$_{Fp}$-nucleic acid sequence, and nucleic acid sequence encoding for a crtW-protein (crtW-nucleic acid sequence), preferably from *F. pelagi* (crtW$_{Fp}$-nucleic acid sequence), *B. aurantiaca* (crtW$_{Ba}$-nucleic acid sequence) or *S. astaxanthinifaciens* (crtW$_{Sa}$-nucleic acid sequence) in at least one recombinant sequence.

In one preferred embodiment, said recombinant bacterium according to the invention comprises only one recombinant sequence, which comprises a crtZ$_{Fp}$-nucleic acid sequence, and a crtW-nucleic acid sequence, preferably crtW$_{Fp}$-nucleic acid sequence, crtW$_{Ba}$-nucleic acid sequence or crtW$_{Sa}$-nucleic acid sequence.

Another aspect of the present invention refers to a method to produce astaxanthin and lysine in recombinant gram-positive bacterium according to the invention such as recombinant *C. glutamicum*, wherein said bacterium comprises a crtZ-nucleic acid sequence, preferably a crtZ$_{Fp}$-nucleic acid sequence, and comprises a crtW-nucleic acid sequence, preferably crtW$_{Fp}$-nucleic acid sequence, crtW$_{Ba}$-nucleic acid sequence or crtW$_{Sa}$-nucleic acid sequence, in at least one recombinant sequence.

Yet another aspect of the present invention refers to a method to produce astaxanthin and lysine in recombinant *C. glutamicum* according to the invention, wherein said recombinant *C. glutamicum* comprises a recombinant sequence, which comprises a crtZ-nucleic acid sequence, preferably a crtZ$_{Fp}$-nucleic acid sequence, and a crtW-nucleic acid sequence, preferably a crtW$_{Fp}$-nucleic acid sequence, crtW$_{Ba}$-nucleic acid sequence or crtW$_{Sa}$-nucleic acid sequence.

Especially preferred is a method according to the invention or a bacterium according to the invention, wherein a crtZ-nucleic acid sequence, preferably a crtZ$_{Fp}$-nucleic acid sequence, and a crtW-nucleic acid sequence, preferably crtW$_{Fp}$-nucleic acid sequence, crtW$_{Ba}$-nucleic acid sequence or crtW$_{Sa}$-nucleic acid sequence, are each expressed and corresponding crtZ-protein and crtW-protein are produced.

In one preferred embodiment, said crtZ-nucleic acid sequence and said crtW-nucleic acid sequence being each part of a recombinant sequence, preferably being part of one recombinant sequence, are each individually operatively linked to a promotor.

In a preferred embodiment, the method of the invention further comprises the step of obtaining astaxanthin and lysine.

In a particular embodiment, recombinant crtW- and/or crtZ-nucleic acid sequences may be expressed from a non-native or heterologous promoter (i.e. a promoter which is heterologous to a crtW- and/or crtZ-nucleic acid sequence, i.e. is not the native crtW- or crtZ-gene promoter of the host bacterium, e.g., *C. glutamicum*) and particularly a strong, non-native or heterologous promoter. Thus, in this embodiment the crtW- or crtZ-nucleic acid sequences are not used with their native promoter. A crtW- or crtZ-nucleic acid sequence may be introduced which is under the control of a non-native promoter.

The use of a non-native promoter may advantageously have the effect of relieving the crtW- or crtZ-nucleic acid sequences of transcriptional repression, as at least some of any repressive elements will be located in the native promoter region. By replacing the native promoter with a non-native promoter devoid of repressive elements responsive to the effects of pathway products, the crtW- or crtZ-nucleic acid sequence will be at least partly relieved of transcriptional repression.

The invention, in one preferred embodiment, may thus provide a method wherein a crtW- and/or a crtZ-nucleic acid sequence is expressed which is not subject to transcriptional repression, e.g. by a product of the astaxanthin pathway or by a repressor of the endogenous crtW- or crtZ-nucleic acid sequence.

In a preferred embodiment, the non-native promoter in view of a crtZ-nucleic acid sequence of *C. glutamicum* and a crtW-nucleic acid sequence of *C. glutamicum* is nevertheless native to *C. glutamicum*.

The introduced sequences may be modified to render them relieved of transcriptional repression, e.g. by mutating or deleting recognition elements for transcriptional repressors or by using expression control elements (e.g. promoters) which are not subject to transcriptional regulation by the transcriptional regulator(s) which normally control expression of the crtW-gene and/or crtZ-nucleic acid sequence, e.g. which control expression in their native situation, for example transcriptional repressors being products of the astaxanthin pathway. The endogenous crtW- and/or crtZ-nucleic acid sequence may alternatively or additionally be modified in this way, or by addition of a stronger promoter. Thus, mutagenesis (including both random and targeted) may for example be used to mutate the endogenous control or regulatory elements so as to increase expression of the endogenous crtW- and/or crtZ-nucleic acid sequence (e.g. increase transcription and/or translation). Alternatively, the organism may be engineered to introduce additional or alternative regulatory elements.

In yet another preferred embodiment, the *C. glutamicum* used for producing a recombinant *C. glutamicum* strain in regard of crtW and crtZ according to the present invention is GRLys1ΔsugRΔldhA, a modified strain of MB001 (ATCC13032) known from Pérez-García, Peters-Wendisch and Wendisch, 2016.

Especially preferably, the expression, preferably overexpression, of a recombinant crtZ$_{Fp}$-nucleic acid sequence and a recombinant crtW-nucleic acid sequence, preferably a crtW$_{Fp}$-nucleic acid sequence, crtW$_{Ba}$-nucleic acid sequence or crtW$_{Sa}$-nucleic acid sequence, results in the production, preferably overproduction, of a crtZ$_{Fp}$-protein encoded by said crtZ$_{Fp}$-nucleic acid sequence and the production, preferably overproduction, of a crtW-protein, preferably a crtW$_{Fp}$-protein, crtW$_{Ba}$-protein or crtW$_{Sa}$-protein, encoded by said crtW-nucleic acid sequence, preferably a crtW$_{Fp}$-nucleic acid sequence, crtW$_{Ba}$-nucleic acid sequence or crtW$_{Sa}$-nucleic acid sequence, respectively.

In yet another preferred embodiment, the crtZ$_{Fp}$-nucleic acid sequence is SEQ ID NO.: 1 or is
a nucleic acid sequence having at least 80% identity as set forth with SEQ ID NO.: 1, or
a nucleic acid sequence that hybridizes with the complement of a nucleic acid sequence according to SEQ ID NO.: 1 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 2 and which amino acid sequence shows crtZ activity.

In yet another preferred embodiment, the source for a nucleic acid sequence encoding for crtW$_{Fp}$ is SEQ ID NO.: 3 or SEQ ID NO.: 5 or is a nucleic acid sequence having at least 80% identity as set forth with SEQ ID NO.: 3 or 5, respectively, or a nucleic acid sequence that hybridizes with the complement of a nucleic acid sequence according to SEQ ID NO.: 3 or 5, respectively, under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 4 or 6, respectively, and which amino acid sequence shows crtW activity.

In yet another preferred embodiment, the source for a nucleic acid sequence encoding for crtW$_{Ba}$ is SEQ ID NO.: 7 or is a nucleic acid sequence having at least 80% identity as set forth with SEQ ID NO.: 7, or a nucleic acid sequence that hybridizes with the complement of a nucleic acid sequence according to SEQ ID NO.: 7 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 8 and which amino acid sequence shows crtW activity.

In yet another preferred embodiment, the source for a nucleic acid sequence encoding for crtW$_{Sa}$ is SEQ ID NO.: 9, or is a nucleic acid sequence having at least 80% identity as set forth with SEQ ID NO.: 9, or a nucleic acid sequence that hybridizes with the complement of a nucleic acid sequence according to SEQ ID NO.: 9 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 10 and which amino acid sequence shows crtW activity.

Yet another aspect of the present invention refers to a method to produce astaxanthin and lysine comprising the step of cultivating recombinant gram-positive bacterium, preferably C. glutamicum according to the invention, under conditions that a recombinant crtZ$_{Fp}$-protein resulting from a recombinant crtZ$_{Fp}$-nucleic acid sequence described herein is overproduced and a recombinant crtW-protein, preferably a crtW$_{Fp}$-, crtW$_{Sa}$-, crtW$_{Ba}$- protein resulting from a crtW-nucleic acid sequence described herein, is overproduced simultaneously, at different times or at overlapping times in said bacterium.

As non-limiting examples for "simultaneously overproduced" recombinant proteins are, e.g., proteins which encoding nucleotide sequences are both individually operatively linked to a constitutively expressing promotor. A non-limiting example for "overproduced at different times" recombinant proteins are, e.g., proteins of which one encoding nucleotide sequences is operatively linked to a substance 1 (e.g. methanol) induced promotor and another encoding nucleotide sequence is operatively linked to a substance 2 (e.g. glucose) induced promotor and the inducing substances are provided to the bacterium at different times. A non-limiting example for overproduced "at overlapping times" recombinant proteins are, e.g., a protein which encoding nucleotide sequence is operatively linked to a substance 1 (e.g. methanol) induced promotor and a protein which encoding nucleotide sequence is operatively linked to a constitutively expressing promotor and the inducing substance is provided to the bacterium only for a specific time period.

Yet another aspect of the present invention refers to a method to produce astaxanthin and lysine comprising the steps of introducing into a gram-positive bacterium according to the invention, preferably a C. glutamicum, a crtZ$_{Fp}$- nucleic acid sequence according to the invention and a crtW-nucleic acid sequence, preferably a crtW$_{Fp}$-, crtW$_{Sa}$-, crtW$_{Ba}$-nucleic acid sequence; and cultivating the gram-positive bacterium, preferably C. glutamicum, under conditions that crtZ$_{Fp}$-protein is overproduced and crtW-protein, preferably a crtW$_{Fp}$-, crtW$_{Sa}$-, crtW$_{Ba}$-protein, is overproduced.

Preferably, both nucleic acid sequences encoding for a crtZ-protein and encoding for a crtW-protein, respectively, are introduced into the gram-positive bacterium, preferably C. glutamicum, simultaneously, e.g. both sequences being comprised in a plasmid which is introduced into C. glutamicum.

The skilled person is aware how to transform plasmid into cells, e.g. by electroporation or heat-shock methods, by methods known in the art (see, e.g., Heider et al, supra).

Methods for introducing nucleic acids and vectors into microorganisms are well known and widely described in the literature. The choice of method may depend on the microorganism used. As described in Heider et al., 2014 (supra), methods for introducing genes into C. glutamicum and suitable plasmids etc. for use in such methods are known and available in the art.

Preferably, each recombinant nucleic acid sequence encoding for a crtZ$_{Fp}$-protein and encoding for a crtW-protein, respectively, is individually operatively linked to a promotor. More preferably, at least one promotor, even more preferably, each promotor individually operatively linked to a recombinant crtZ$_{Fp}$-nucleic acid sequence (promotor 1) and a crtW-nucleic acid sequence, preferably a crtW$_{Fp}$-, crtW$_{Sa}$-, or crtW$_{Ba}$-nucleic acid sequence, respectively, (promotor 2), is a constitutively expressing promotor, preferably a constitutively expressing strong promotor.

The use of promotors leads, when activated or constitutively expressing, to an overexpression of the operatively linked nucleic acid sequence and results in the overproduction of the encoded recombinant protein.

One preferred embodiment refers a process according to the invention or a recombinant bacterium according to the invention comprises a recombinant crtZ-nucleic acid sequence, wherein the crtZ-protein encoding nucleic acid sequence is a nucleic acid sequence according to SEQ ID NO.: 1, or is a nucleic acid sequence having at least 80% identity as set forth with SEQ ID NO.: 1, or a nucleic acid sequence that hybridizes with the complement of a nucleic acid sequence according to SEQ ID NO.: 1 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 2 and which amino acid sequence shows crtZ activity.

In yet another preferred embodiment, the source for a nucleic acid sequence encoding for crtW is SEQ ID NO.: 3 or SEQ ID NO.: 5 or is a nucleic acid sequence having at least 80% identity as set forth with SEQ ID NO.: 3 or 5, respectively, or a nucleic acid sequence that hybridizes with the complement of a nucleic acid sequence according to SEQ ID NO.: 3 or 5, respectively, under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 4 or 6, respectively, and which amino acid sequence shows crtW activity.

In yet another preferred embodiment, the source for a nucleic acid sequence encoding for crtW is SEQ ID NO.: 7 or is a nucleic acid sequence having at least 80% identity as set forth with SEQ ID NO.: 7, or a nucleic acid sequence that hybridizes with the complement of a nucleic acid sequence according to SEQ ID NO.: 7 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 8 and which amino acid sequence shows crtW activity.

In yet another preferred embodiment, the source for a nucleic acid sequence encoding for crtW is SEQ ID NO.: 9, or is a nucleic acid sequence having at least 80% identity as set forth with SEQ ID NO.: 9, or a nucleic acid sequence that hybridizes with the complement of a nucleic acid sequence according to SEQ ID NO.: 9 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or a nucleic acid sequence encoding for an amino acid sequence having at least 80% identity with SEQ ID NO.: 10 and which amino acid sequence shows crtW activity.

(Sequence) "identity" may be assessed by any convenient method. However, for determining the degree of sequence identity between sequences, computer programs that make multiple alignments of sequences are useful, for instance Clustal W (Thompson et al, (1994) Nucleic Acids Res., 22: 4673-4680). Furthermore, the Dali server at the European Bioinformatics institute offers structure-based alignments of protein sequences (Holm (1993) J. Mol. Biol., 233: 123-38; Holm (1995) Trends Biochem. Sci., 20: 478-480; Holm (1998) Nucleic Acid Res., 26: 316-9).

Yet another preferred embodiment refers to a method or a recombinant *C. glutamicum* wherein in the genome of the recombinant *C. glutamicum* crtR, crtY from *C. glutamicum* and crtEb were deleted and the genome comprises crtEBI, crtY$_{Pa}$, and pSH1_crtW$_{Fp}$+ pEC-XT-crtZ$_{Fp}$, crtR, crtY from *C. glutamicum* and crtEb were deleted and the genome comprises crtEBI, crtY$_{Pa}$, and pSH1_crtW2$_{Fp}$+ pEC-XT-crtZ$_{Fp}$, crtR, crtY from *C. glutamicum* and crtEb were deleted and the genome comprises crtEBI, crtY$_{Pa}$, and pSH1_crtW$_{Sa}$+ pEC-XT-crtZ$_{Fp}$, or crtR, crtY from *C. glutamicum* and crtEb were deleted and the genome comprises crtEBI, crtY$_{Pa}$, and pSH1_crtW$_{Sa}$+ pEC-XT-crtZ$_{Fp}$, more preferably the recombinant *C. glutamicum* is recombinant *C. glutamicum* GRLys1ΔsugRΔldhA with the following modifications crtR, crtY from *C. glutamicum* and crtEb were deleted and the genome comprises crtEBI, crtY$_{Pa}$, and pSH1_crtW1$_{Fp}$+ pEC-XT-crtZ$_{Fp}$, crtR, crtY from *C. glutamicum* and crtEb were deleted and the genome comprises crtEBI, crtY$_{Pa}$, and pSH1_crtW2$_{Fp}$+ pEC-XT-crtZ$_{Fp}$, crtR, crtY from *C. glutamicum* and crtEb were deleted and the genome comprises crtEBI, crtY$_{Pa}$, and pSH1_crtW$_{Sa}$+ pEC-XT-crtZ$_{Fp}$, or crtR, crtY from *C. glutamicum* and crtEb were deleted and the genome comprises crtEBI, crtY$_{Pa}$, and pSH1_crtW$_{Ba}$+ pEC-XT-crtZ$_{Fp}$.

Even more preferred, the recombinant *C. glutamicum* is recombinant *C. glutamicum* ASTA LYS as described herein (i.e. BETALYS (pECXT99A-crtZFp)(XpSH1-crtWFp).

Another preferred embodiment refers to a process according to the invention or a recombinant bacterium according to the invention, wherein the recombinant crtW-nucleic acid sequence is a crtW$_{Fp}$-, crtW$_{Sa}$-, or crtW$_{Ba}$-nucleic acid sequence, more preferably a crtW$_{Ba}$-nucleic acid sequence.

Another preferred embodiment refers to a process according to the invention or a recombinant bacterium according to the invention, wherein said recombinant bacterium, preferably *C. glutamicum*, comprises a recombinant nucleic acid sequence encoding for a promotor 1 which is operatively linked to a crtZ$_{Fp}$-nucleic acid sequence.

Another preferred embodiment refers to a process according to the invention or a recombinant bacterium according to the invention, wherein said recombinant bacterium, preferably *C. glutamicum*, comprises a recombinant nucleic acid sequence encoding for a promotor 2 which is operatively linked to a crtW-nucleic acid sequence, preferably a crtW$_{Fp}$-, crtW$_{Sa}$-, or crtW$_{Ba}$-nucleic acid sequence.

Another preferred embodiment refers to a process according to the invention or a recombinant bacterium according to the invention, wherein the promotor 1 which is operatively linked to a crtZ$_{Fp}$-nucleic acid sequence and the promotor 2 which is operatively linked to a crtW-nucleic acid sequence, preferably a crtW$_{Fp}$-, crtW$_{Sa}$-, or crtW$_{Ba}$-nucleic acid sequence, are activated by different sources, e.g. one of both is constitutively expressing while the other is activated/induced, e.g. by IPTG or a saccharide such as xylitol or mannitol. The skilled person is well aware of further compound inducible promotors.

Another preferred embodiment refers to a process according to the invention or a recombinant bacterium according to the invention, wherein promotor 2 is a constitutively expressing promotor.

Another preferred embodiment refers to a process according to the invention or a recombinant bacterium according to the invention, wherein induction of promotor activity of promotor 1 and induction of promotor activity of promotor 2 occur at different times.

Another preferred embodiment refers to a process according to the invention, wherein induction of promotor activity of promotor 1 occurs within the first 6 hours of the cultivation, in the exponential growth phase.

Another preferred embodiment refers to a process according to the invention or a recombinant bacterium according to the invention, wherein promotor 1 and promotor 2 are constitutively expressing promotors.

Another preferred embodiment refers to a process according to the invention, wherein the amount of astaxanthin is at least 0.5 mg/gCDW (cell dry weight), more preferably at least 0.75 mg/gCDW, even more preferably at least 0.8 mg/gCDW after 48 h of incubation at 30° C., e.g., in a 50 ml culture.

Another preferred embodiment refers to a process according to the invention, wherein the concentration of astaxanthin after 48 h incubation at 30° C., e.g., in a 50 ml culture, is at least 1.6 mg/l, more preferably 2.45 mg/l, even more preferably at least 2.6 mg/l and the concentration of lysine is at least 9.2 mM, more preferably 13.8 mM, even more preferably at least 14.7 mM.

Notably, all strains produced herein except of ASTA LYS (BETALYS (pECXT99A-crtZFp)(pSH1-crtWFp)) were not able to produce increased amounts of astaxanthin and lysine.

Xylose and arabinose can be obtained from lignocelluloses by hydrolysis and these pentose sugars do not have competing uses in the food and feed industries. *C. glutamicum* wild type can neither utilize xylose nor arabinose, may be engineered for growth on these pentose sugars as sole and combined carbon sources (Meiswinkel et al., 2013; Schneider et al., 2011; Wendisch et al., 2016a). Example 4 shows that the use of different carbon sources for the production of β-carotene and lysine is possible.

Accordingly, another aspect of the invention relates to a process for preparation of carotenoids, preferably astaxanthin and/or β-carotene, in recombinant *C. glutamicum* of the invention, preferably BETALYS, wherein arabinose is used as carbon source and wherein in the genome of said recombinant *C. glutamicum* araA, preferably as depicted in SEQ ID NO: 87, araB, preferably as depicted in SEQ ID NO: 88 and araD, preferably as depicted in SEQ ID NO: 89, is introduced. Another aspect of the invention relates to a process for preparation of carotenoids, preferably astaxanthin and/or β-carotene, in recombinant *C. glutamicum* of the invention, preferably BETALYS, wherein in the genome of said recombinant *C. glutamicum* xylA, preferably as depicted in SEQ ID NO: 90, and xylB, preferably as depicted in SEQ ID NO: 91, is introduced. A further aspect of the invention relates to a process for preparation of carotenoids, preferably astaxanthin and/or β-carotene, in recombinant *C. glutamicum* of the invention, preferably BETALYS, wherein arabinose and xylulose are used as carbon source and wherein in the genome of said recombinant *C. glutamicum* araA, preferably as depicted in SEQ ID NO: 87, araB, preferably as depicted in SEQ ID NO: 88, araD, preferably as depicted in SEQ ID NO: 89, xylA, preferably as depicted in SEQ ID NO: 90, and xylB, preferably as depicted in SEQ ID NO: 91, are introduced. Preferably, the introduced genes are operatively linked to a promoter.

Another aspect of the present invention refers to a method and a strain for the production of lycopene and lysine, preferably a process for the preparation of lycopene in recombinant *C. glutamicum*, wherein in the genome of said recombinant *C. glutamicum* strain sugR and ldh and crtR from *C. glutamicum*, crtYe, crtYf, crtEb were deleted, Ptuf-crtEcrtBcrtI was introduced. Preferably, the strain is LYC LYS as described herein.

Yet another aspect of the present invention refers to a method and a strain for the production of decaprenoxanthin and lysine, preferably a process for the preparation of decaprenoxanthin in recombinant *C. glutamicum*, wherein in the genome of said recombinant *C. glutamicum* strain sugR and ldh are deleted, or sugR and ldh and crtR are deleted, sugR and ldh and crtR are deleted and Ptuf-crtEcrtBcrtI is introduced, or sugR and ldh and crtR are deleted and Ptuf-crtEcrtBcrtI and Ptuf-crtY$_{Pa}$ is introduced. Preferably, the strain is selected from the group consisting of GRLYS1ΔsugRΔldh), 2=DECA LYS1, 3=DECA LYS2 and 4=DECA-BETA LYS as described herein.

Yet another aspect of the present invention refers to a method and a strain for the production of canthaxanthin and lysine, preferably a process for the preparation of canthaxanthin in recombinant *C. glutamicum*, wherein in the genome of said recombinant *C. glutamicum* strain sugR and ldh and crtR from *C. glutamicum*, crtYe, crtYf, crtEb were deleted, Ptuf-crtEcrtBcrtI was introduced and crtW, preferably crtW$_{Fp}$, are introduced. Preferably, the strain is CAN LYS.

Yet another aspect of the present invention refers to a method and a strain for the production ozeaxanthin and lysine, preferably a process for the preparation of ozeaxanthin and lysine in recombinant *C. glutamicum*, wherein in the genome of said recombinant *C. glutamicum* strain sugR and ldh and crtR from *C. glutamicum*, crtYe, crtYf, crtEb were deleted, Ptuf-crtEcrtBcrtI was introduced and crtZ, preferably crtZ$_{Fp}$, are introduced. Preferably, the strain is ZEA LYS Yet another aspect of the present invention refers to a method and a strain for the production of β-carotene and lysine, preferably a process for the preparation of β-carotene and lysine in recombinant *C. glutamicum*, wherein in the genome of said recombinant *C. glutamicum* strain sugR and ldh and crtR are deleted and Ptuf-crtEcrtBcrtI and Ptuf-crtY$_{Pa}$ is introduced or sugR and ldh and crtR and crtYe and crtYf and crtEb are deleted and Ptuf-crtEcrtBcrtI and Ptuf-crtY$_{Pa}$ is introduced. Preferably, the strain is DECA-BETA LYS or BETA LYS.

Yet another aspect of the present invention refers to a method and a strain for the production of β-carotene, decaprenoxanthin and lysine preferably a process for the preparation of β-carotene, decaprenoxanthin and lysine in recombinant *C. glutamicum*, wherein in the genome of said recombinant *C. glutamicum* strain sugR and ldh and crtR are deleted and Ptuf-crtEcrtBcrtI and Ptuf-crtY$_{Pa}$ is introduced. Preferably, the strain is DECA-BETA LYS.

The invention is also characterized by the following items:

1. A process for the preparation of astaxanthin and lysine in recombinant *C. glutamicum*, wherein in the genome of said recombinant *C. glutamicum* crtR, crtY from *C. glutamicum* and crtEb were deleted and crtEBI, crtYPa and at least one recombinant sequence which comprises a nucleic acid sequence encoding for a crtZ-protein (crtZ-nucleic acid sequence), preferably from *F. pelagi* (crtZFp-nucleic acid sequence) and at least one recombinant sequence which comprises a nucleic acid sequence encoding for a crtW-protein (crtW-nucleic acid sequence), preferably from *F. pelagi* (crtWFp-nucleic acid sequence), *B. aurantiaca* (crtWBa-nucleic acid sequence) or *S. astaxanthinifaciens* (crtWSa-nucleic acid sequence) were introduced.

2. The process according to item 1, wherein the crtZFp-nucleic acid sequence is SEQ ID NO.: 1, or
a nucleic acid sequence having at least 80% identity as set forth with SEQ ID NO.: 1, or
a nucleic acid sequence that hybridizes with the complement of a nucleic acid sequence according to SEQ ID NO.: 1 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or
a nucleic acid sequence encoding for an amino acid sequence having at least 80% identity with SEQ ID NO.: 2 and which amino acid sequence shows crtZ activity.
3. The process according to item 2, wherein the crtZFp-nucleic acid sequence is SEQ ID NO.: 1.
4. The process according to item 1 or item 2, wherein the crtW-nucleic acid sequence is SEQ ID NO.: 3 or SEQ ID NO.: 5 or is
a nucleic acid sequence having at least 80% identity as set forth with SEQ ID NO.: 3 or 5, respectively, or
a nucleic acid sequence that hybridizes with the complement of a nucleic acid sequence according to SEQ ID NO.: 3 or 5, respectively, under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or
is a nucleic acid sequence encoding for an amino acid sequence having at least 80% identity with SEQ ID NO.: 4 or 6, respectively, and which amino acid sequence shows crtW activity; or
is SEQ ID NO.: 7 or is
a nucleic acid sequence having at least 80% identity as set forth with SEQ ID NO.: 7, or a nucleic acid sequence that hybridizes with the complement of a nucleic acid sequence according to SEQ ID NO.: 7 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or
a nucleic acid sequence encoding for an amino acid sequence having at least 80% identity with SEQ ID NO.: 8 and which amino acid sequence shows crtW activity; or is SEQ ID NO.: 9, or
is a nucleic acid sequence having at least 80% identity as set forth with SEQ ID NO.: 9, or a nucleic acid sequence that hybridizes with the complement of a nucleic acid sequence according to SEQ ID NO.: 9 under the following hybridization conditions: 0.1×SSC, 0.1% SDS, 65° C. and wash conditions 2×SSC, 0.1% SDS, 65° C., followed by 0.1×SSC, 0.1% SDS, 65° C. (high stringency conditions), or
a nucleic acid sequence encoding for an amino acid sequence having at least 80% identity with SEQ ID NO.: 10 and which amino acid sequence shows crtW activity.
5. The process according to any one of the items 1 to 3, wherein the crtW-protein is of SEQ ID NO.: 4, 6, 8 or 10.
6. The process according to any of the preceding items, wherein said recombinant *C. glutamicum* comprises a nucleic acid sequence encoding for a promotor 1 which is operatively linked to a crtZFp-nucleic acid sequence according to item 2 or item 3.
7. The process according to any of the preceding items, wherein said recombinant *C. glutamicum* comprises a nucleic acid sequence encoding for a promotor 2 which is operatively linked to a crtWFp-, crtWBa-, or crtWSa-nucleic acid sequence according to item 4 or 5.
8. The process according to any one of the preceding items, wherein the promotor 1 and the promotor 2 are not induced by the same inducing compound.
9. The process according to any one of the preceding items, wherein promotor 2 is a constitutively expressing promotor.
10. The process according to any one of the preceding items, wherein induction of promotor activity of promotor 1 and induction of promotor activity of promotor 2 occur at different times.
11. The process according to any one of the preceding items, wherein induction of promotor activity of promotor 1 occurs at the beginning of the cultivation, in the exponential growth phase within the first 6 hours.
12. The process according to any one of items 1 to 7 and 8 to 10, wherein promotor 1 and promotor 2 are constitutively expressing promotors.
13. The process according to any one of the preceding items, wherein said recombinant *C. glutamicum* comprises the following modifications: deletion of sugR and deletion of LdhA, deletion of crtR insertion of crtEBI deletion of genes crtYe, crtYf and crtEb insertion of crt YPa, preferably as Ptuf-crtYPa, insertion of crtZFp, preferably as pECXT99a_crtZFp, insertion of crtWFp, preferably as pSH1-crtWFp.
14. A recombinant *C. glutamicum*, wherein said recombinant *C. glutamicum* comprises a crtY-nucleic acid sequence, preferably a crtYPa-nucleic acid sequence, further comprises a crtZ-nucleic acid sequence, which is not from *C. glutamicum*, preferably a crtZFp-nucleic acid sequence, and further comprises a crtW-nucleic acid sequence, preferably a crtWFp-, crtWBa-, or crtWSa-nucleic acid sequence;
more preferably, in the genome of said recombinant *C. glutamicum* crtR, crtY from *C. glutamicum* and crtEb were deleted and crtEBI, crtYPa and at least one recombinant sequence which comprises a nucleic acid sequence encoding for a crtZ-protein, preferably from *F. pelagi* (crtZFp-nucleic acid sequence) and at least one recombinant sequence which comprises a nucleic acid sequence encoding for a crtW-protein, preferably from *F. pelagi* (crtWFp-nucleic acid sequence), *B. aurantiaca* (crtWBa-nucleic acid sequence) or *S. astaxanthinifaciens* (crtWSa-nucleic acid sequence) were introduced.
15. The recombinant *C. glutamicum*, according to item 15, wherein the nucleic acid sequence encoding for a crtZ-protein is a nucleic acid sequence according to item 2 or 3 and the nucleic acid sequence encoding for a crtW-protein is a nucleic acid sequence according to item 4 or 5.

EXAMPLES

Example 1: Co-Production of Astaxanthine and Lysine

Agilent 1200 series HPLC system (Agilent Technologies)
Autoclave DE-23 (Systec)
Autoclave S. p. A. (Fedegari)
Axio Lab.A1 (Zeiss)
BioCapt MW
Safe 2020 Biological Safety Cabinet (Thermo Scientific)
Centrifuge 5417 R (Eppendorf)
Centrifuge 5424 (Eppendorf)
Centrifuge 5810 R (Eppendorf)
DC Power Supply 5004
Ecotron (Infors HT)
Gene Pulser Xcell™ (Biorad)
Incubator (Memmert)
Spectrophotometer ND-1000 (Nanodrop)
Spectrophotometer V-1200 (VWR)
Thermocycler FlexCycler (Biometra)
Thermocycler T3000 (Biometra)

Thermomixer comfort (Eppendorf)
UV Transilluminator (UVP)
Vortex Genie 2 (Scientific Industries)
Waterbath 3042 (Köttermann)

The chemicals used to prepare the buffers and solutions were obtained by AppliChem GmbH (Darmstadt), Carl Roth GmbH & Co. KG (Karlsruhe), Merck KGaA (Darmstadt), Sigma-Aldrich GmbH (Taufkirchen) and VWR International GmbH (Darmstadt). The components and preparations for the buffers and solutions are listed in Table 1.

TABLE 1

Buffers and solutions. Components, amounts and preparation of the used buffers and solutions

| Component | End concentration |
|---|---|
| RF1 | |
| RbCl | 100 mM |
| $MnCl_2 \times 4\ H_2O$ | 50 mM |
| Potassium acetate | 30 mM |
| $CaCl_2 \times 2\ H_2O$ | 10 mM |
| Glycerol | 15% (w/v) |
| adjust pH to 5.8 with 0.2 % acetic acid autoclave | |
| RF2 | |
| MOPS | 10 mM |
| RbCl | 10 mM |
| $CaCl_2 \times 2\ H_2O$ | 75 mM |
| Glycerol | 15% (w/v) |
| adjust pH to 6.8 with NaOH autoclave | |
| EPB1 | |
| HEPES | 20 mM |
| Glycerol | 5% (w/v) |
| adjust pH to 7.2 with 2N NaOH autoclave | |
| EPB2 | |
| HEPES | 5 mM |
| Glycerol | 15% (w/v) |
| adjust pH to 7.2 with 2N NaOH autoclave | |

| 40% glucose | Amount |
|---|---|
| Glucose | 400 g/l |
| autoclave | |

| TAE | End concentration |
|---|---|
| Tris | 40 mM |
| Acetic acid | 20 mM |
| $Na_2EDTA$ | 1 mM |

TABLE 1-continued

Buffers and solutions. Components, amounts and preparation of the used buffers and solutions

| 1% Agarose | Amount |
|---|---|
| Agarose | 10 g/l |
| cook with 1 × TAE until solution is clear, store at 60° C. | |

| | End concentration |
|---|---|
| Gel Loading Buffer | |
| $Na_2EDTA$ | 100 mM |
| Glycerol | 50% (w/v) |
| Bromphenol blue | 0.10% |
| Xylene cyanol | 0.20% |
| Orange G | 0.15% |

| Component | |
|---|---|
| Borat Buffer | |
| Boronic acid | 100 mM |
| adjust pH to 7 with 30% NaOH | |
| Ethambutol dihydrochloride | |
| Ethambutol dihydrochloride | 36 mM |

Bioinformatic Tools: Clone Manager Version 9.0 (Sci-Ed)

The components and preparations of the various media are listed in Table 2. To solve the components, deionized $H_2O$ was used. For the preparation of medium for plates, 16 g/l agar was added before autoclaving. To prepare media for organisms with antibiotic resistance, the antibiotics were added to the liquid media immediately before preparing the cultures. For producing plates with selective media, antibiotics were added before pouring the plates.

In Table 3 the components of the solution for trace elements are listed. Table 4 contains the antibiotics and their used concentrations.

TABLE 2

Media. Components, amounts and preparation of media

| Component | Amount |
|---|---|
| LB Medium | |
| Bacto tryptone | 10 g/l |
| Yeast extract | 5 g/l |
| NaCl | 10 g/l |
| autoclave | |
| BHIS Medium | |
| Brain Heart Infusion Medium | 37 g/l |
| autoclave | |
| Sorbitol | 90 g/l |
| autoclave | |
| BHIS 10% sucrose Medium | |
| Brain Heart Infusion Medium | 37 g/l |

TABLE 2-continued

Media. Components, amounts and preparation of media

| Component | Amount |
|---|---|
| | autoclave |
| Sorbitol | 90 g/l |
| Sucrose | 100 g/l |
| | autoclave |
| CGXII | |
| $(NH_4)_2SO_4$ | 20 g/l |
| Urea | 5 g/l |
| $KH_2PO_4$ | 1 g/l |
| $K_2HPO_4$ | 1 g/l |
| $CaCl_2$ | 10 mg/l |
| $MgSO_4 \times 7\ H_2O$ | 250 mg/l |
| MOPS | 42 g/l |
| | adjust pH to 7 with KOH |
| | autoclave |
| Biotin (sterile) | 0.2 mg/l |
| PKS (sterile) | 30 mg/l |
| Carbon source (sterile) | x g/l |
| Trace elements (sterile) | 1 ml/l |

TABLE 3

Trace elements. Components and amount to prepare trace elements used for CGXII medium

| Component | Amount |
|---|---|
| $FeSO_4 \times 7\ H_2O$ | 10 g/l |
| $MnSO_4 \times 7\ H_2O$ | 10 g/l |
| $ZnSO_4 \times 7\ H_2O$ | 1 g/l |
| $CuSO_4$ | 0.2 g/l |
| $NiCl_2 \times 6\ H_2O$ | 20 g/l | sterile filtrating

TABLE 4

Antibiotics. Concentration of stock solution and end concentration of antibiotics used to prepare selective media

| Antibiotic | Stock solution conc. [mg/ml] | End conc. [µg/ml] |
|---|---|---|
| Kanamycin | 50 | 15/25 |
| Nalidixic acid | 50 | 50 |
| Tetracycline | 5 | 5 |

Oligonucleotides:

The primers used for PCR were ordered from Metabion GmbH (Planegg/Steinkirchen) (Table 5).

TABLE 5

Oligonucleotides.

| Name | Sequence 5' → 3' |
|---|---|
| crtY-A | AAAAGGATCCAGTCGGCTTCAGCATCC (SEQ ID NO: 63) |
| crtEb-DelD | AAAACCCGGGATGTGTGGGAGGCTTCGC (SEQ ID NO: 64) |
| IntY2 | GAAGTCCAGGAGGACATACAATGCAACCGCATTAT GATCTG (SEQ ID NO: 65) |

TABLE 5-continued

Oligonucleotides.

| Name | Sequence 5' → 3' |
|---|---|
| IntY3 | TCTTACTACTTGCGCTAGGTACAGTTAACGATGAG TCGTCATAATGG (SEQ ID NO: 66) |
| NW23 $P_{tuf}$-fw | TGGCCGTTACCCTGCGAATG (SEQ ID NO: 67) |
| crtI-sacI-rv | *TTTTGAGCTC*TTAAGTCCGATCCACACTGT (SEQ ID NO: 68) |
| cg0725_E | GCGCGAAGATTTGATGGG (SEQ ID NO: 69) |
| cg0725_F | ACTTGTCACCACAGCACTAC (SEQ ID NO: 70) |
| NW29 Op1-E | TCGCACCATCTACGACAACC (SEQ ID NO: 71) |
| NW30 Op1-F | CTACGAAGCTGACGCCGAAG (SEQ ID NO: 72) |
| crtE-B | CCCATCCACTAAACTTAAACAGATTGTCATGCCAT TGTCCAT (SEQ ID NO: 73) |
| crtE-PstI-fw | *AAAACTGCAG*GAAAGGAGGCCCTTCAGATGGACAA TGGCATGACAATC (SEQ ID NO: 74) |
| NW31 Op2-E | GTGGTGCTCGAGAACATAAG (SEQ ID NO: 75) |
| NW32 Op2-F | CGGTCACCCGTAACAATCAG (SEQ ID NO: 76) |
| crtY-E | TTGCACCTGCTGGATACGAA (SEQ ID NO: 77) |
| crtEb-DelF | AAAACAATGCGCAGCGCA (SEQ ID NO: 78) |
| PD5 (pSH1-fw) | ACCGGCTCCAGATTTATCAG (SEQ ID NO: 79) |
| 582 (pSH1-rv, pEKEx3-rv) | ATCTTCTCTCATCCGCCA (SEQ ID NO: 80) |
| pECXT-fw | AATACGCAAACCGCCTCTCC (SEQ ID NO: 81) |
| pECXT-rv | TACTGCCGCCAGGCAAATTC (SEQ ID NO: 82) |
| cg0725_A | GCAGGTCGACTCTAGAGGATCCCCGCGCGAAGATT TGATGGG (SEQ ID NO: 83) |
| cg0725_D | CCAGTGAATTCGAGCTCGGTACCCCTTGTCACCAC AGCACTACT (SEQ ID NO: 84) |
| Pa_crtY-fw | CTGCAGGTCGACTCTAGAGGAAAGGAGGCCCTTCA GATGCAACCGCATTATGATCTG (SEQ ID NO: 85) |
| Pa_crtY-rv1 | CGGTACCCGGGGATCTTAACGATGAGTCGTCATAA TGG (SEQ ID NO: 86) |

Sequences used to amplify genes.
Sequence in italics = linker sequence for hybridization Biological Material:

The strains and plasmids used for growth experiments or constructing new strains are listed in Table 6 and 7. *C.* glutamicum GRLys1ΔsugRΔldhA was used to construct further strains by deleting or inserting genes.

TABLE 6

Strains used for this invention

| Strain | Relevant characteristics | Source or reference |
|---|---|---|
| E. coli S17-1 | hsdR Pro, Rec⁻, genome integrated RP4-2Tc::Mu Km::Tn7 | Simon, Priefer and Puhler, 1983 |
| C. glutamicum strains | | |
| MB001 | prophage cured, genome reduced ATCC 13032 | Baumgart et al., 2013 |
| GRLys1ΔsugRΔldhA | ATCC 13032 with following modifications: Δpck, pyc$^{P458S}$, hom$^{V59A}$, 2 copies of lysC$^{T311I}$, 2 copies of asd, 2 copies of dapA, 2 copies of dapB, 2 copies of ddh, 2 copies of lysA, 2 copies of lysE, in-frame deletion of prophages CGP1 (cg1507-cg1524), CGP2 (cg1746-cg1752), CGP3 (cg1890-cg2071), in-frame deletion of sugR (cg2115) and ldhA (cg3219) | Pérez-Garcia, Peters-Wendisch and Wendisch, 2016 |
| DECA LYS1 | crtR deletion mutant of GRLys1ΔsugRΔldhA | this work |
| DECA LYS2 | DECA LYS1 derivative with genome integration of the artificial operon crtE, crtB, crtI under control of the P$_{tuf}$ promoter | this work |
| DECA-BETA LYS | DECA LYS2 derivative with genome integration of crtY$_{Pa}$ under control of the P$_{tuf}$ promoter | this work |
| LYC LYS | crtY$_e$Y$_f$Eb deletion mutant of DECA LYS2 | this work |
| BETA LYS | LYC LYS derivative with genome integration of crtY$_{Pa}$ under control of P$_{tuf}$-Promoter | this work |
| CAN LYS | BETA LYS with plasmid pSH1_crtW1$_{Fp}$ | this work |
| ZEA LYS | BETA LYS with plasmid pECXT_crtZ$_{Fp}$ | this work |
| ASTA LYS | BETA4 (pECXT99A_crtZFp)(pSH1-crtWFp) | this work |

TABLE 7

Plasmids invention

| Plasmid/Vector | Relevant characteristics | Source or reference |
|---|---|---|
| pk19mobsacB-ΔcrtR | Km$^R$, shuttle vector for E. coli and C. glutamicum to construct deletions and insertions in C. glutamicum; contains a construct to delete crtR | (Henke et al., 2016) |
| pk19mobsacB-Int-crtEBI | Km$^R$, shuttle vector for E. coli and C. glutamicum to construct deletions and insertions in C. glutamicum; contains a construct to insert the artificial operon crtEBI under control of P$_{tuf}$ promoter, additional ribosome binding site in front of crtB for the integration into the CGP2 cured region of C. glutamicum | (Henke et al., 2016) |
| pk19mobsacB-ΔcrtYEb | Km$^R$, shuttle vector for E. coli and C. glutamicum to construct deletions and insertions in C. glutamicum; contains a construct to delete crtY$_e$Y$_f$Eb | (S. A. E. Heider et al., 2014) |
| pk19mobsacB-Int-crtY$_{Pa}$ | Km$^R$, shuttle vector for E. coli and C. glutamicum to construct deletions and insertions in C. glutamicum; contains a construct to insert crtY of Pantoea ananatis under control of P$_{tuf}$ promoter into the cgp1 cured region of C. glutamicum | (Henke et al., 2016) |
| pSH1_crtW1$_{Fp}$ | Km$^R$, P$_{tuf}$, pHM519 oriV$_{Cg}$, C. glutamicum/E. coli expression shuttle vector, constitutive expression of crtW from Fulvimarina pelagi with artificial ribosome binding site | (Henke et al., 2016) |
| PEC-XT99A_crtZ$_{Fp}$ (pECXT_crtZ$_{Fp}$) | Tet$^R$, P$_{trc}$lacI$^q$, pGA1 oriV$_{Cg}$, C. glutamicum/E. coli expression shuttle vector, IPTG-inducible expression of crtZ from Fulvimarina pelagi with artificial ribosome binding site | (Henke et al., 2016) |

Cultivation:

If not mentioned otherwise, *Escherichia coli* was cultivated in LB at 37° C. with an agitation of 180 rpm and *Corynebacterium glutamicum* was cultivated in BHIS at 30° C. and 120 rpm.

Plasmid Isolation:

To isolate plasmids from *E. coli* bacteria cells, 20 ml of an overnight culture were processed according to the GeneJET Plasmid Miniprep kit from Thermo Scientific. To elute the plasmids, the elution buffer was substituted with 50 µl MilliQ. Subsequently the concentration was determined by Spectrophotometer ND-1000 (Nanodrop).

Competent *E. coli* Cells:

A colony of *E. coli* S17-1 was cultivated in 5 ml LB and incubated overnight at 37° C. Two 500 ml flasks with 50 ml LB were inoculated with 1 ml of the overnight culture. The flasks were incubated for 2-3 hours until they reached an OD600 of 0.2-0.4. Afterwards the cultures were transferred to 50 ml Falcon tubes and incubated on ice for 10 minutes. Thereafter the cells were centrifuged for 20 minutes at 4000 rpm and 4° C. in a Centrifuge 5810 R (Eppendorf). The cells were washed in 30 ml ice-cooled RF1-Buffer and centrifuged for 7 minutes at 4000 rpm and 4° C. Afterwards the pellets were resuspended in 8 ml ice-cooled RF2-Buffer and incubated on ice for 10-15 minutes. 100 µl aliquots were frozen in liquid nitrogen and stored at −80° C.

Transformation in *E. coli* Via Heat-Shock:

Competent *E. coli* cells were thawed on ice. 50 ng plasmid DNA was added to the cells and incubated on ice for 15 minutes. Thereafter the heat-shock at 42° C. for 1.5 minutes occurred. Afterwards the cells were incubated on ice for 1 minute. 700 µl of LB medium was added. Cells were regenerated for 45-60 minutes at 37° C. and 450 rpm in a Thermomixer comfort (Eppendorf). The cells were plated on LB plates with the required antibiotics and incubated at 37° C.

Colony-PCR:

Colony-PCR was performed to verify if the transformation of a plasmid into a bacteria cell or a genomic integration/deletion was successful. For this process Taq-polymerase from NEB was used. For each PCR a forward and a reverse primer were added to the reaction mix, the list which primers were used for which plasmid or strain is listed in Table 5. The components of a single reaction mix and the parameters of the program for the PCR cycler can be seen in Table 8 and 9. To perform the PCR the Thermocycler FlexCycler or Thermocycler T3000 (Biometra) was used. After each PCR the samples were analysed by gel electrophoresis.

TABLE 8

A single reaction mix for colony PCR. Components and used amounts
Taq DNA polymerase reaction mix

| Components | Volume [µl] |
|---|---|
| MilliQ | 15.5 |
| 10 × Thermo polymerase buffer | 2 |
| dNTPs (10 mM) | 0.4 |
| Forward primer (10 mM) | 1 |
| Reverse Primer (10 mM) | 1 |
| Taq-polymerase | 0.04 |
| Total volume | 20 |

TABLE 9

PCR program used for colony PCR with the rmocycler
Colony-PCR program

| | | |
|---|---|---|
| Initial denaturation | 95° C. | 5 min |
| Denaturation | 95° C. | 20 s |
| Annealing | 58-65° C. | 25 s |
| Elongation | 72° C. | 60 s/kb |
| | | 35 cycles |
| Final Elongation | 72° C. | 5 min |
| Storage | 4° C. | ∞ |

Gel Electrophoresis:

To separate the DNA fragments on the basis of their size, gel electrophoresis was performed with 1% agarose gel (peqGOLD Universal Agarose, peqlab). Each sample was mixed with 5 µl 6× triple dye loading buffer and 9 µl of the sample were loaded on the gel. As a standard to compare the sizes of the fragments, 5 µl 1 kb ladder (NEB) were used. The gel was run at 100 V for 20-30 minutes and stained in an ethidium bromide bath (400 µl 1% ethidium bromide solution in 700 ml H2O) for 5-9 minutes. To analyse the gels, a UV transilluminator (UVP) was used.

PCR Clean-Up:

The kit DNA, RNA, and protein purification (Macherey-Nagel, Düren, Germany) was used to purify the amplified DNA fragments. The steps were performed according to the instructions, but instead of using the elution buffer of the kit, the fragments were eluted with 15 µl MilliQ. The concentration was measured by Spectrophotometer ND-1000 (Nanodrop) and the fragments were sequenced.

Conjugation:

Genomic integrations/deletions in the chromosome of *C. glutamicum* were carried out via homologous recombination events. With this method, genomic regions can be deleted or foreign DNA can be integrated by introducing the suicide vector pk19mobsacB (FIG. 5) (Schäfer et al., 1994). Since this vector is based on the replicon pMB1, it can only be replicated in *E. coli* (Sutcliffe, 1979). The plasmid contains a multiple cloning site (MCS), $Km^R$ gene, RP4mob DNA region and a genetically modified sacB gene (Schäfer et al., 1994). The MCS with unique restriction sites is convenient for cloning. The $Km^R$ can be used as a selection marker for cells which contain the plasmid (Schäfer et al., 1994). When expressed, the levansucrase of the sacB gene is lethal for *C. glutamicum* in presence of sucrose (Jager et al., 1992), which is why cells that contain the plasmid can't grow on sucrose. This can be used as another selection marker. The plasmid pk19mobsacB was transferred (Schäfer et al., 1994) into the *E. coli* strain S17-1, which contains a genome integrated RP4 plasmid. This RP4 derivative enables the pk19mobsacB to be transferred into other strains (Simon, Priefer and Puhler, 1983), in this case: *C. glutamicum*. Since the vector only has an oriV for *E. coli*, the plasmid needs to be integrated via homologous recombination into the genome of the recipient to be replicated (Schäfer et al., 1994) (FIG. 5C). Via a second recombination, the vector was removed from the genome and there are two possible results: The complete plasmid is removed and the initial genome is restored (WT) or by homologous recombination the flanking regions (FR) are partially exchanged and the genomic region between the flanking regions is removed from the genome (deletion mutant). To insert DNA regions into a genome, the suicide vector contains the DNA region, which is to be inserted, between the flanking regions. The procedure is the same as for deleting genomic regions.

Two pre-cultures were inoculated, one with cells of the donor (*E. coli* S17-1 pk19mobsacB) in 50 ml LB with $Km^{25}$ and one with cells of the recipient (*C. glutamicum*) in 50 ml BHIS. The flasks were incubated overnight. Two flasks with fresh media and appropriate antibiotics were inoculated, both to an $OD_{600}$ of 0.1 and incubated until they reached an $OD_{600}$ of 1-1.5. 50 ml of the recipient were transferred to a 50 ml Falcon tube and centrifuged for 10 minutes at 4000 rpm (Centrifuge 5810 R, Eppendorf). The cells were resuspended with 5 ml BHIS and aliquots of 800 µl were incubated at 50° C. for 9 minutes (Thermomixer comfort, Eppendorf).

Two 15 ml Falcon tubes, each with 10 ml of the donor culture, were harvested and centrifuged for 10 minutes at 4000 rpm. The pellets were resuspended in 1 ml LB.

200 µl of the donor were added to each aliquot of the recipient and inverted gently. The tubes were centrifuged for 3 minutes at 3000 rpm (Centrifuge 5424, Eppendorf) and the pellets were resuspended by stirring carefully with a 1 ml pipette tip.

Sterile cellulose acetate or cellulose nitrate filters were placed onto BHIS plates and the cell suspensions were pipetted onto the filters. The plates were incubated for 20 minutes under the sterile bench (Safe 2020 Biological Safety Cabinet, Thermo Scientific, Massachusetts, USA), in which the lids were left open for 12 minutes. Afterwards the plates were incubated at 30° C. for at least 20 hours. Then the filters were transferred to 15 ml Falcon tubes to remove the cells from the filters with 500 µl BHIS. The cell suspensions were centrifuged for 4 minutes at 4000 rpm and the supernatants were discarded. The pellets were resuspended and plated onto BHIS $Km^{15}$ $NaI^{50}$ plates and incubated for two days at 30° C. Colonies which grew on the plates were picked onto a fresh BHIS $Km^{25}$ $NaI^{50}$ plate to dispose of *E. coli* cells and were incubated overnight at 30° C. The new colonies were picked parallel, first onto a BHIS $Km^{25}$ and then onto a BHIS $Km^{25}$+10% sucrose plate and incubated overnight. Six Colonies which grew on BHIS $Km^{25}$ but not on $Km^{25}$+10% sucrose were streaked on BHIS 10% sucrose plates with a glass pipette and incubated for 2 days for the second recombination to occur. Colonies from these plates were parallel picked onto BHIS $Km^{25}$ and BHIS 10% sucrose and incubated overnight. Cells which grew on BHIS 10% sucrose but not on BHIS $Km^{25}$ were used to perform a colony-PCR to verify that the deletion or insertion was successful.

Competent *C. glutamicum* Cells:

A pre-culture of 5 ml BHIS with appropriate antibiotics and cell material of *C. glutamicum* was incubated overnight at 30° C. and an agitation of 120 rpm. Two flasks with 50 ml fresh BHIS with required antibiotics were inoculated with 1 ml of the pre-culture and incubated until they reached an OD600 of 0.6. To each flask, Ampicillin [1.5 µg/ml] was added and they were incubated for 1-1.5 hours. Afterwards the suspensions were transferred to 50 ml Falcon tubes and centrifuged for 7 min at 4000 rpm and 4° C. in a Centrifuge 5810 R (Eppendorf). The pellets were washed three times with 30 ml ice-cooled EPB1-Buffer and centrifuged as performed before. Thereafter the pellets were resuspended in 750 µl ice-cooled EPB2-Buffer and incubated for 10-15 minutes on ice. Aliquots of 150 µl were stored at −80° C.

Transformation in *C. glutamicum* Via Electroporation:

Competent *C. glutamicum* cells were thawed on ice. 500 ng of purified plasmid DNA was added to the cells and incubated for 15 minutes on ice. The cells were transferred into a pre-cooled sterile electroporation cuvette. The electroporation was performed with 2.5 kV, 200Ω and 25 µF with Gene Pulser Xcell™ (Biorad). Immediately after the electroporation the cells were transferred to a tube with 750 µl BHIS which was preheated to 46° C. The heat shock was performed at 46° C. for 6 minutes. Afterwards the regeneration occurred at 30° C. for 60-90 minutes with an agitation of 450 rpm in a Thermomixer comfort (Eppendorf). The cells were plated onto a BHIS plate with the required antibiotics and incubated for two days at 30° C.

Growth Experiment with *C. glutamicum*:

A pre-culture with 20 ml BHIS, 50 mM glucose, appropriate antibiotics and cell material was incubated overnight at 30° C. and 120 rpm. Cells for an OD600 of 1.1 in 50 ml were harvested and centrifuged for 7 min at 4000 rpm in a Centrifuge 5810 R (Eppendorf). Afterwards they were washed with 20 ml basic CGXII. To prepare the CGXII medium, 100 mM glucose, 1 mM IPTG and appropriate antibiotics were added. The pellet was resuspended with 50 ml of the CGXII medium and transferred to a 500 ml flask. The flask was incubated for 24-48 hours with an agitation of 120 rpm. The OD600 of the culture was measured at different time points. After 24, 32 or 36 hours the glucose content in the flask was measured with a glucose test strip DIABUR Test 5000 (Roche Diabetes Care Deutschland GmbH, Mannheim, Germany). At the end of the growth experiment, 2×1 ml from the flask were transferred to 2 ml Eppendorf tubes and centrifuged for 10 minutes at max rpm in a Centrifuge 5242 (Eppendorf). The supernatant was transferred to a 1.5 ml tube. The pellet and the supernatant were stored at −20° C. until further use.

Carotenoid Extraction:

The pellet was thawed at room temperature for 5 minutes and resuspended in 800 µl of methanol:acetone (7:3) with 0.05% BHT (2, 6-Di-tert-Butyl-4-methylphenol). The tube was incubated for 15 minutes in a 60° C. waterbath 3042 (Köttermann), while it was shaken every 5 minutes. After the incubation, the tube was centrifuged for 10 minutes at max rpm (Centrifuge 5424, Eppendorf). The supernatant was transferred to a fresh 2 ml tube. If the pellet was not colourless, another extraction round was performed. The supernatant was centrifuged for 15 minutes at max rpm and transferred to a fresh 2 ml tube. 500 µl were analysed by HPLC.

Preparation of samples for amino acid analysis: The frozen supernatants were thawed at room temperature. Then they were centrifuged for 15 minutes at max rpm in a Centrifuge 5424 (Eppendorf) to spin down possible remaining cells and residues.

49 ml Borat Buffer were mixed with 0.5 ml 10 mM asparagine, 495 µl of this solution were transferred to a vial and 5 µl of the sample were added. Standards were prepared as prescribed in Table 10. The prepared sample and the standards were analysed by HPLC.

TABLE 10

Preparation of standards of one amino acid. In each set of standards, there are $H_2O$, asparagine as internal standard and one amino acid. In this case it is either glutamate or lysine. The total volume of each vial is 495 µl.

| Amino acid (10 mM) | Volume [µl] | | | | | | | |
|---|---|---|---|---|---|---|---|---|
| | 50 µM | 100 µM | 150 µM | 200 µM | 250 µM | 300 µM | 350 µM | 400 µM |
| Asparagine | 5 | 5 | 5 | 5 | 5 | 5 | 5 | 5 |
| Glutamate | 2.5 | 5 | 7.5 | 10 | 12.5 | 15 | 17.5 | 20 |
| Lysine | 2.5 | 5 | 7.5 | 10 | 12.5 | 15 | 17.5 | 20 |
| $H_2O$ | 492.5 | 490 | 487.5 | 485 | 482.5 | 480 | 477.5 | 475 |
| Total | | | | | 495 | | | |

High performance liquid chromatography: The carotenoid extracts and supernatants with amino acids were analysed by high performance liquid chromatography (HPLC) using the Agilent 1200 series HPLC system (Agilent Technologies).

Automatic precolumn derivatization with ortho-phthaldialdehyde (Georgi, Rittmann and Wendisch, 2005) was used to determine the amino acids. The column system consisted of a precolumn (LiChrospher 100 RP18 EC-5µ (40×4 mm), CS Chromatographie Service GmbH, Langerwehe, Germany) and a reversed-phase main column (LiChrospher 100 RP18 EC-5µ (125×4 mm), CS Chromatographie Service GmbH) which were used to separate the amino acids. A fluorescence detector (FLD G1321A, 1200 series, Agilent Technologies) was used to detect the amino acids (Pérez-Garcia, Peters-Wendisch and Wendisch, 2016) with excitation at 230 nm and emission at 450 nm (Peters-Wendisch et al., 2014). $_L$-Asparagine was used as internal standard to quantify the amount of amino acid (Pérez-Garcia, Peters-Wendisch and Wendisch, 2016). The buffers used for this process were sodium acetate 0.1 M, pH 7.1, and methanol in a mixture of 4:1 (unpublished method from Pérez-Garcia 2016).

To determine the carotenoids a diode array detector (DAD) was used to detect the UV/visible (Vis) spectrum. To quantify the carotenoids, every maximum of the extracted wavelength chromatogram at $\lambda_{max}$ 470 nm was integrated and the respective profiles of UV/Vis were analysed. For the standard calibration curve samples with different carotenoids and various concentrations were measured. The carotenoids were lycopene (Sigma-Aldrich), β-carotene (Sigma-Aldrich), canthaxanthin (Sigma-Aldrich), zeaxanthin (Sigma-Aldrich) and astaxanthin (Sigma-Aldrich). The stock solution [1 mg/ml] was dissolved in dichloromethane and different amounts of the solution were diluted in methanol:acetone (7:3) with 0.05% BHT to prepare the standards (Henke et al., 2016).

50 µl of the samples were run through a precolumn (LiChrospher 100 RP18 EC-5µ, (40×4 mm), CS-Chromatographie) and a reversed-phase main column (LiChrospher 100 RP18 EC-5, (125×4 mm), CS-Chromatographie). Buffers used were methanol (A) and methanol:water (9:1) (B). The gradient started with 0% of B at 0 minutes, increasing to 100% of B at 10 minutes and 100% of B at 32.5 minutes with a flow rate of 1.5 ml/min (Henke, unpublished method from Henke 2016).

Strain Construction by Conjugation and Transformation:

To construct new strains by conjugation, the various pk19mobsacB plasmids were transferred into S17-1 cells. The strain GRLys1ΔsugRΔIdhA was used as the initial strain. The first step was to delete the gene crtR (cg0725) which encodes a putative transcriptional regulator (Pfeifer et al., 2016) with the plasmid pk19mobsacB-ΔcrtR to construct the strain DECA LYS1 (GRLys1ΔsugRΔIdhAΔcrtR) (FIG. 1). To verify the genomic modification, the primers cg0725_E and cg0725_F were used for colony-PCR. Then the artificial operon crtEBI was integrated using the plasmid pk19mobsacB-Int-crtEBI which created the strain DECA LYS2 (GRLys1ΔsugRΔIdhAΔcrtR-IntcrtEBI). To verify the genomic modification, the primer combinations NW29 Op1-E+NW300 µl-F, NW29 Op1-E+crtE-B and crtE-PstI-fw+NW300 µl-f were used for colony-PCR.

The gene crtY$_{Pa}$ was integrated into DECA LYS2 using the plasmid pk19mobsacB-Int-crtY$_{Pa}$ constructing DECA-BETA LYS (GRLys1ΔsugRΔIdhAΔcrtR-IntcrtEBI-IntcrtY$_{Pa}$). To verify the genomic modification, the primers NW31 OP2-E and NW32 OP2-F were used for colony-PCR.

Starting from DECA LYS2, the genes crtY$_e$Y$_f$Eb (=crtY$_e$ crtY$_f$ and crtEb) were deleted creating the strain LYC LYS (GRLys1ΔsugRΔIdhAΔcrtR-IntcrtEBIΔcrtY$_e$Y$_f$Eb). To verify the deletion, the primers crtY-E and crtEb-DelF were used.

The integration of crtY$_{Pa}$ in LYC LYS led to the strain BETA LYS (GRLys1ΔsugRΔIdhAΔcrtR-IntcrtEBIΔcrtY$_e$Y$_f$Eb-IntcrtY$_{Pa}$). For this colony-PCR the primers NW31 OP2-E and NW32 OP2-F were used. The strain BETA LYS was used as the initial strain for transformation. The plasmids pSH1_crtW1$_{Fp}$ and pECXT_crtZ$_{Fp}$ were isolated from the strains E. coli DH5α pSH1_crtW$_{Fp}$ and E. coli DH5α pECXT_crtZ$_{Fp}$.

The vector pSH1_crtW1$_{Fp}$ was transferred into the competent BETA LYS cells by electroporation with Gene Pulser Xcell™ (Biorad) constructing the strain CAN LYS. For colony-PCR the standard vector primers for pSH1, PD5 (pSH1-fw) and 582 (pSH1-rv, pEKEx3-rv), were used.

The plasmid pECXT_crtZ$_{Fp}$ was transferred into BETA LYS to create the strain ZEA LYS. To verify via colony-PCR the standard vector primers pECXT-fw and pECXT-rv, were used.

After confirmation that the transformations were successful, the vector pECXT_crtZ$_{Fp}$ was transferred into CAN LYS resulting in ASTA LYS1.

The plasmid pSH1_crtW1$_{Fp}$ was transferred into ZEA LYS to construct ASTA LYS2. The verification was made with the standard primers for each new added plasmid.

Cultures for Production of Carotenoids and Glutamate:

To produce glutamate in C. glutamicum there need to be specific conditions, e.g. biotin limitation or addition of ethambutol dihydrochloride (following called ethambutol or EMB). The strains tested were MB001, MB001ΔcrtR and ASTA1. Each strain was grown in different conditions (i) CGXII medium without further addition, serves as control, (ii) CGXII medium with EMB [50 µg/ml], (iii) biotin limitation. The pre-cultures were prepared with 50 ml BHIS, 50 mM glucose, appropriate antibiotics and cell material. They were incubated overnight.

(i) Control: Cell suspension to inoculate a flask with 50 ml to an OD$_{600}$ of 1.1 were centrifuged for 7 minutes at 4000 rpm and 4° C. (Centrifuge 5810 R, Eppendorf). The cells were resuspended in basic CGXII and centrifuged. The pellet was resuspended in CGXII medium with 100 mM glucose, appropriate antibiotics and 50 mM IPTG if required.

(ii) EMB: The main culture was prepared as described in (i) but 50 µg/ml EMB were added to the flask before incubation.

(iii) Biotin limitation: A second pre-culture was prepared with CGXII, 100 mM glucose, appropriate antibiotics and 50 mM IPTG if required. But instead of adding biotin with a concentration of 0.2 mg/ml, the concentration was 0.01 mg/ml. The flask was incubated overnight. The main culture was prepared as described in (i) with a concentration of biotin of 1 µg/ml.

The flasks were incubated for 48 hours at 30° C. with an agitation of 120 rpm.

Cultures for Production of Carotenoids and Lysine:

Pre-cultures of the strains GRLys1ΔsugRΔIdhA, DECA LYS1, DECA LYS2, DECA-BETA LYS, LYC LYS, BETA LYS, CAN LYS, ZEA LYS and ASTA LYS were inoculated with 20 ml BHIS, 50 mM glucose (pre-cultivation) and appropriate antibiotics. The flasks were incubated overnight at 30° C. at 120 rpm. Cell suspension to inoculate a flask with 50 ml of the same medium (main cultivation) to an OD$_{600}$ of 1.1 were centrifuged for 7 minutes at 4000 rpm and 4° C. (Centrifuge 5810 R, Eppendorf). The cells were washed with basic CGXII. The pellet was resuspended in CGXII medium with 100 mM glucose, appropriate antibiotics and 50 mM IPTG if required. The flasks were incubated for 48 hours at 30° C. and an agitation of 120 rpm.

Establishment of a platform strain for the coproduction of carotenoids and lysine on the basis of a metabolically optimized lysine producer GRLys1ΔsugRΔIdhA: The strain GRLys1ΔsugRΔIdhA (Unthan et al., 2015) was used as a platform strain to construct the following strains which are able to produce carotenoids and lysine simultaneously.

The almost white colour of GRLys1ΔsugRΔIdhA was changed to a pale yellow, when crtR, the gene encoding for the putative transcriptional regulator of carotenogenesis in C. glutamicum, was deleted, leading to the construction of the strain DECA LYS1 (FIG. 1). The deletion was verified by colony-PCR (FIG. 5). The colonies 1, 31, 38, 48 and 50 were sequenced and showed no mutations but the correct deletion of crtR. DECA LYS1 was used for the construction of the next strain. 1 kb ladder from NEB was used for every gel electrophoresis and the sizes are shown in the FIG. 5.

Insertion of the artificial operon crtEBI lead to a stronger yellow pigmentation and to the construction of the strain DECA LYS2. The verification of the insertion was done by three colony-PCRs with the primer combinations NW29 Op1-E+crtE-B, NW29 Op1-E+NW30 OP1-F and crtE-PstI-fw+NW30 OP1-F. This was necessary, as C. glutamicum naturally possesses an operon with the genes crtB and crtI.

The combination NW29 and crtE-B lead to a 1,500 bp fragment. The fragment produced with the primers NW29 and NW30 had a size of 6,300 bp, while the combination crtE-fw and NW30 lead to a size of 4,800 bp. The colony-PCR verified the insertion of the artificial operon in the colonies 27, 29, 32 and 41 (FIG. 5).

When the lycopene cyclase crtY$_{Pa}$ (S. A. E. Heider et al., 2014) was integrated into the genome, the colour changed from yellow to orange in the strain DECA-BETA LYS. The fragments without the integrated gene are 2,100 bp while the fragments which contain the integration are about 3,800 bp (FIG. 5).

The strain LYC LYS contains the deletion of the genes crtYEb, encoding for the lycopene elongase and the C50 ε-cyclase (Krubasik, Kobayashi and Sandmann, 2001), leading to the accumulation of lycopene in the strain LYC LYS. The colonies 1, 12, 16, 21 and 22 among others had the size of 1,050 bp (FIG. 5) and showed the expected pink colour.

BETA LYS had an orange pigmentation due to the production of the carotenoid β-carotene by the insertion of the gene crtY$_{Pa}$. The DNA fragment had a size of 3,800 bp and the colonies 8, 11, 29 and 33 were used to make glycerol stocks (FIG. 5).

The transformation of the plasmids pSH1_crtW1$_{Fp}$ and pECXT_crtZ$_{Fp}$ lead to the synthesis of canthaxanthin in CAN LYS (FIG. 5) with a slightly pink colour, zeaxanthin in ZEA LYS (FIG. 5), a strong orange pigmentation, or to the red carotenoid astaxanthin in ASTA LYS (FIG. 5). The plasmids were already sequenced and known to be correct. The colony-PCR showed that the vectors were successfully transformed, with fragment sizes of 1,200 bp for the gene crtW1$_{Fp}$ and 1,000 bp for the gene crtZ$_{Fp}$ including the flanking regions of the plasmids (FIG. 5).

The strains produced carotenoids and the values were analysed by HPLC (FIG. 3). GRLys1ΔsugRΔIdhA, DECA LYS1, DECA LYS2 and DECA-BETA LYS produced decaprenoxanthin. The strains DECA-BETA LYS and BETA LYS synthesized β-carotene. Lycopene was detected in LYC LYS and canthaxanthin in CAN LYS. ZEA LYS produced zeaxanthin and astaxanthin was synthesized in ASTA LYS. The decaprenoxanthin concentration significantly increased from GRLys1ΔsugRΔIdhA (0.05±0 mg/g CDW) to the other decaprenoxanthin producing strains, with DECA-BETA LYS containing the lowest concentration (0.54±0.05 mg/g CDW) and DECA LYS2 the highest (1.51±0.12 mg/g CDW). The amount of β-carotene was high in both producing strains, 3.19±0.31 mg/g CDW in DECA-BETA LYS and 3.77±0.73 mg/g CDW in BETA LYS, which is the highest concentration of all produced carotenoids. Zeaxanthin was accumulated to 0.34±0.02 mg/g CDW in ZEA LYS and the red canthaxanthin was produced up to 0.92±0.11 mg/g CDW in CAN LYS. In ASTA LYS an amount of 0.84±0.11 mg/g CDW astaxanthin was detected. The data are listed in Table 11.

The strain GRLys1ΔsugRΔIdhA produced the highest amount of lysine, 24.79±1 mM (FIG. 4). The other strains produced less lysine, varying from 14.33±0.46 to 18.79±0.19 mM. The highest amount, apart from GRLys1ΔsugRΔIdhA, was produced by DECA-BETA LYS with a concentration of 18±0.19 mM lysine. The data are listed in Table 12.

All in all, the simultaneous production of C40/C50 carotenoids and the amino acid lysine in one cultivation is possible with the strains used and constructed in this work.

TABLE 11

Carotenoid production in growth experiment for carotenoids and lysine after 48 hours. The various strains with their corresponding carotenoids are listed, as well as the final OD$_{600}$ after 48 hours and the production of the carotenoids in different units.

| Strain | Carotenoid | Final OD | Carotenoid mg/g CDW | mg/l | mg/l*h |
|---|---|---|---|---|---|
| GRLYS1ΔsugRΔIdh | Decaprenoxanthin | 10.90 ± 0.26 | 0.05 ± 0 | 0.14 ± 0.00 | >0.01 ± 0.00 |
| DECA LYS1 | Decaprenoxanthin | 10.00 ± 0.49 | 1.41 ± 0.14 | 3.52 ± 0.27 | 0.07 ± 0.01 |
| DECA LYS2 | Decaprenoxanthin | 13.00 ± 1.04 | 1.51 ± 0.12 | 4.94 ± 0.80 | 0.10 ± 0.02 |
| DECA-BETA LYS | Decaprenoxanthin | 14.17 ± 0.47 | 0.54 ± 0.05 | 1.93 ± 0.20 | 0.04 ± 0.00 |
| DECA-BETA LYS | β-carotene | 14.17 ± 0.47 | 3.19 ± 0.31 | 11.26 ± 0.85 | 0.23 ± 0.02 |
| LYC LYS | Lycopene | 14.60 ± 0.85 | 0.67 ± 0.1 | 2.44 ± 0.22 | 0.05 ± 0.00 |
| BETA LYS | β-carotene | 12.61 ± 0.65 | 3.77 ± 0.73 | 11.89 ± 2.30 | 0.25 ± 0.05 |
| CAN LYS | Canthaxanthin | 11.45 ± 0.79 | 0.92 ± 0.11 | 2.62 ± 0.28 | 0.05 ± 0.01 |
| ZEA LYS | Zeaxanthin | 11.76 ± 0.30 | 0.34 ± 0.02 | 0.99 ± 0.06 | 0.02 ± 0.00 |
| ASTA LYS | Astaxanthin | 13.27 ± 1.01 | 0.84 ± 0.11 | 2.76 ± 0.21 | 0.06 ± 0.00 |

TABLE 12

Production of lysine in the growth experiment for carotenoids and lysine. The strains, final OD$_{600}$ and the lysine production in different units after 48 hours are listed.

| Strain | Final OD | Lysine [mM] | Lysine [mg/l] |
|---|---|---|---|
| GRLYS1ΔsugRΔIdh | 10.90 ± 0.26 | 24.79 ± 1.00 | 3624.31 ± 146.38 |
| DECA LYS1 | 10.00 ± 0.49 | 16.16 ± 1.28 | 2362.94 ± 187.53 |
| DECA LYS2 | 13.00 ± 1.04 | 18.61 ± 1.37 | 2720.20 ± 200.56 |
| DECA-BETA LYS | 14.17 ± 0.47 | 18.79 ± 0.19 | 2746.98 ± 28.43 |
| LYC LYS | 14.60 ± 0.85 | 16.14 ± 1.43 | 2359.92 ± 209.19 |
| BETA LYS | 16.57 ± 0.87 | 14.33 ± 0.46 | 2094.85 ± 67.44 |
| CAN LYS | 11.45 ± 0.79 | 14.40 ± 0.41 | 2104.47 ± 59.89 |
| ZEA LYS | 11.76 ± 0.30 | 17.29 ± 0.62 | 2527.49 ± 91.16 |
| ASTA LYS | 13.27 ± 1.01 | 15.93 ± 1.74 | 2328.24 ± 253.88 |

Example 2: Repetition of Experiments Leads to Similar Results

The experiments were performed as described in Example 1 unless stated otherwise using the strains described in Example 1.

First, the production of carotenoids was measured in different *C. glutamicum* strains. Table 13 shows the results. The highest amount of carotenoids was produced in the BETALYS strain with 11.6±0.94 mg/l carotenoids (β-carotene). ASTALYS showed a production of 3.15±0.58 mg/l astaxanthin, a value even higher than the one shown in Table 11 of Example 1.

TABLE 13

Carotenoid production in lysine-coproducing *C. glutamicum* strains. Titer, yield and productivity of carotenoids from cultivation in CGXII (100 mM glucose) and 32 h. Decaprenoxanthin is given as β-carotene equivalents (GRLys1ΔsugRΔldhA and DECALYS2), lycopene (LYCLYS), β-carotene (BETALYS), zeaxanthin (ZEALYS, canthaxanthin (CAN LYS) and astaxanthin (ASTALYS). Means of three biological triplicates and standard deviations are given.

| Strain | CDW [g/L] | [mg/g CDW] | [mg/L] | Vol. prod. [mg/L/h] | Yield [mg/g] |
|---|---|---|---|---|---|
| GRLYS1ΔsugRΔldhA | 3.48 ± 0.12 | 0.06 ± 0.03 | 0.20 ± 0.09 | 0.01 ± 0.00 | 0.01 ± 0.00 |
| DECALYS1 | 3.58 ± 0.18 | 1.70 ± 0.11 | 6.10 ± 0.38 | 0.19 ± 0.01 | 0.34 ± 0.02 |
| LYCLYS | 4.02 ± 0.11 | 0.68 ± 0.11 | 2.74 ± 0.49 | 0.09 ± 0.02 | 0.15 ± 0.03 |
| BETALYS | 2.93 ± 0.13 | 3.96 ± 0.17 | 11.60 ± 0.94 | 0.36 ± 0.03 | 0.64 ± 0.05 |
| ZEALYS | 2.65 ± 0.10 | 0.49 ± 0.02 | 1.29 ± 0.02 | 0.04 ± 0.00 | 0.07 ± 0.00 |
| CANLYS | 2.69 ± 0.14 | 0.84 ± 0.05 | 2.26 ± 0.04 | 0.07 ± 0.00 | 0.13 ± 0.00 |
| ASTALYS | 3.16 ± 0.09 | 1.00 ± 0.18 | 3.15 ± 0.58 | 0.10 ± 0.02 | 0.17 ± 0.03 |

The strain GRLys1ΔsugRΔIdhA produced the highest amount of lysine, 23.61±0.43 mM. The other strains produced less lysine, varying from 12.37±0.65 to 19.08±1.17 mM. The highest amount, apart from GRLys1ΔsugRΔIdhA, was produced by DECALYS1 with a concentration of 19.08±1.17 mM lysine. The data are listed in Table 14. ASTALYS produced lysine to a concentration of 16.2±1.31 mM, a value that is comparable to the one presented in Table 12 of Example 1.

TABLE 14

Lysine production in carotenoid-coproducing *C. glutamicum* strains. Biomass, titers, volumetric productivity and yield are shown as mean values.

| Strain | CDW [g/L] | Lysine [mM] | Lysine [g/L] | Vol. prod. [g/L/h] | Yield [g/g] |
|---|---|---|---|---|---|
| GRLYS1ΔsugRΔldhA | 3.48 ± 0.12 | 23.61 ± 0.43 | 3.45 ± 0.06 | 0.11 ± 0.00 | 0.19 ± 0.00 |
| DECALYS1 | 3.58 ± 0.18 | 19.08 ± 1.17 | 2.79 ± 0.17 | 0.09 ± 0.01 | 0.15 ± 0.01 |
| LYCLYS | 4.02 ± 0.11 | 15.57 ± 0.46 | 2.27 ± 0.07 | 0.07 ± 0.00 | 0.13 ± 0.00 |
| BETALYS | 2.93 ± 0.13 | 12.37 ± 0.65 | 1.81 ± 0.10 | 0.06 ± 0.00 | 0.10 ± 0.01 |
| ZEALYS | 2.65 ± 0.10 | 16.92 ± 0.34 | 2.47 ± 0.07 | 0.08 ± 0.00 | 0.14 ± 0.00 |
| CANLYS | 2.69 ± 0.14 | 14.46 ± 0.94 | 2.11 ± 0.14 | 0.07 ± 0.00 | 0.12 ± 0.01 |
| ASTALYS | 3.16 ± 0.09 | 16.20 ± 1.31 | 2.37 ± 0.19 | 0.07 ± 0.00 | 0.13 ± 0.01 |

These results further demonstrate that the simultaneous production of C40/C50 carotenoids and the amino acid lysine in one cultivation is possible with the strains used and constructed in this work.

Example 3: Fed-Batch Fermentation of *C. glutamicum* ASTALYS

A bioreactor with a total volume of 20 L and a working volume of 15 L was used (MBR Bioreactor AG, Switzerland). It was equipped with three six-bladed Rushton turbines and four baffles. Operating pH and oxygen saturation in the medium ($pO_2$) were followed by electrodes (Ingold, Germany). By automated addition of KOH (4 M) and phosphoric acid (10%) pH was kept at 7.0. Samples for quantification were taken by an autosampler and cooled down to 4° C. until use. Initial volume of the fermentation was 12 L with additional feeding volume of 3 L. Fermentation was carried out with 0.4 bar overpressure and aeration rate was set to 12 NL $min^{-1}$. Stirrer speed was regulated in a cascade to maintain the oxygen saturation at 60% (Pérez-García et al., 2016). Antifoam was added manually to avoid foaming by the use of Struktol (1:10). The feeding profile was activated when the $pO_2$ signal reached above 60% for the first time and stopped when it fell below 60%. Feed was pumped with 0.1 g $min^{-1}$ resulting in low sugar concentrations during the whole feeding-phase and an oscillating $pO_2$ signal around 60%. Moreover a cascade was included in the fermentation allowing a stirrer speeding up when $pO_2$ fell below 30% until $pO_2$ of 60% was reached again. The maximum stirring speed was set to 500 $min^{-1}$ (Pérez-García et al., 2016). The process was inoculated with the cell pellet of 600 ml of an overnight culture grown at 30° C. and 120 rpm on a rotary shaker in complex medium containing 13.5 g $L^{-1}$ soypeptone, 7 g $L^{-1}$ yeast extract, 2.5 g $L^{-1}$ NaCl, 2.3 g $L^{-1}$ $K_2HPO_4$, 1.5 g $L^{-1}$ $KH_2PO_4$, 0.25 g $L^{-1}$ $MgSO_4$ $7H_2O$ and 15 g $L^{-1}$ D-glucose. The fermentation was performed in the same medium as for the pre-cultivation, however 20 g $L^{-1}$ D-glucose were used. Feed-medium consisted of 400 g $L^{-1}$ D-glucose as well as 232 g $L^{-1}$ $(NH_4)_2SO_4$ (autoclaved separately) (Pérez-García et al., 2016).

Coproduction of L-lysine and astaxanthin by metabolically engineered *C. glutamicum* strain ASTALYS was tested in a 20 L fermenter with a working volume of 15 L (FIG. 6). The feeding phase started after 24 h of cultivation and feeding stopped after 101 h when glucose was consumed. Astaxanthin and L-lysine were both produced in the bioreactor with maximal titers of 10 mg/L and 48.2 g/L, respectively. Considering consumption of the substrate glucose, the product yields were 0.07 mg/g for astaxanthin and 0.35 g/g for L-lysine. The volumetric productivities were 0.01 mg of astaxanthin and 0.44 g of L-lysine per liter and hour (FIG. 6). L-Lysine was successfully co-produced with astaxanthin and other carotenoids.

Example 4: Alternative Carbon Sources for Coproduction of β-Carotene and L-Lysine In order to test the possibility to coproduce carotenoids, such as β-carotene, with L-lysine from alternative carbon sources, *C. glutamicum* strain BETALYS was transformed with plasmids allowing for growth with xylose and arabinose, respectively: For the use of arabinose as carbon source, the strain was additionally transformed with the araBAD operon from *E. coli* (b0061-b0063) encoding for arabinose isomerase (AraA, SEQ ID NO: 87), ribulokinase (AraB, SEQ ID NO: 88) and ribulose-5-phosphate-4-epimerase (AraD, SEQ ID NO: 89). For xylulose as carbon source, the strain was transformed with xylose isomerase xylA from *Xanthomonas campestris* (XCC1758, SEQ ID NO: 90) and xylulokinase xylB from *C. glutamicum* (cg0147, SEQ ID NO: 91). Cells were grown in CGXII minimal medium with 10 g/L of either glucose, arabinose or xylose as sole carbon and energy source. The empty vector control strain BETALYS(pVWEx1) produced around 6 mg/L β-carotene and 1.7 g/L of L-lysine from glucose corresponding to yields of 0.6 mg/g and 0.17 g/g, respectively (FIG. 7).

Coproduction was achieved from both alternative carbon sources (Table 15). Production of β-carotene and L-lysine was decreased when arabinose (BETALYS (pVWEx1-araBAD)) was used as substrate. However, still 4.5 mg/L β-carotene and 1.2 g/L L-lysine were produced with yields of 0.45 mg/g and 0.12 g/g. With xylose as sole carbon source (BETALYS (pVWEx1-xalAb)), titers for the secreted and the cell-bound product were similar to cultivations with glucose as sole carbon source. With xylose, β-carotene titers of around 7 mg/L (corresponding to a yield of 0.7 mg/g xylose) and L-lysine titers of around 1.5 g/L (yield of 0.15 g/g) were obtained.

TABLE 15

Coproduction of β-carotene and lysine overproducing *C. glutamicum* strains from non-food competitive substrates. Titers are shown as mean values.

| Strain | β-carotene [mg/L] | Lysine [g/L] |
| --- | --- | --- |
| BETALYS (pVWEx1) | 6.0 ± 0.4 | 1.7 ± 0.1 |
| BETALYS (pVWEx1-araBAD) | 4.5 ± 0.3 | 1.2 ± 0.01 |
| BETALYS (pVWEx1-xylAB) | 7.0 ± 0.2 | 1.5 ± 0.01 |

7 REFERENCES

Abbes, M., Baati, H., Guermazi, S., Messina, C., Santulli, A., Gharsallah, N. and Ammar, E. (2013) 'Biological properties of carotenoids extracted from *Halobacterium halobium* isolated from a Tunisian solar saltern.', *BMC complementary and alternative medicine*, 13, p. 255. doi: 10.1186/1472-6882-13-255.

Agranoff (1959) 'Isopentenol pyrophsophate isomerase', *Journal of the American Chemical Society*, 81(5), pp. 1254-1255.

Ajinomoto Co. (2015) *Analysts' Meeting for FY2015 Consolidated Results*. Available at: www.ajinomoto.com/en/ir/ir_library/meeting_qa_2015.html (Accessed: 8 Nov. 2016).

Ajinomoto Co. (2016a) *Food Products Business*. Available at: www.ajinomoto.com/enfir/pdf/Food-Oct2016.pdf.

Ajinomoto Co. (2016b) *Life Support Business*. Available at: www.ajinomoto.com/en/ir/pdf/Life_Support-Oct2016.pdf.

Armstrong, G. A. (1994) 'Eubacteria show their true colors: Genetics of carotenoid pigment biosynthesis from microbes to plants', *Journal of Bacteriology*, 176(16), pp. 4795-4802.

Asai, T., Aida, K. and Ōishi, K. (1957) 'On L-Glutamic Acid Fermentation', *Bulletin of the Agricultural Chemical Society of Japan*, 21(2), pp. 134-135. doi: 10.1080/03758397.1957.10857370.

Baumgart, M., Unthan, S., Rückert, C., Sivalingam, J., Grünberger, A., Kalinowski, J., Bott, M., Noack, S. and Frunzke, J. (2013) 'Construction of a Prophage-Free Variant of *Corynebacterium glutamicum* ATCC 13032 for Use as a Platform Strain for Basic Research and Industrial Biotechnology', *Applied and Environmental Microbiology*, 79(19), pp. 6006-6015. doi: 10.1128/AEM.01634-13.

BBC Research (2015) *The Global Market for Carotenoids—FOD025E*. Available at: www.bccresearch.com/market-research/food-and-beverage/carotenoids-global-market-report-fod025e.html.

Bhosale, P. and Bernstein, P. S. (2005) 'Microbial xanthophylls', *Applied Microbiology and Biotechnology*, pp. 445-455. doi: 10.1007/s00253-005-0032-8.

Biswal, S. (2014) 'Oxidative stress and astaxanthin: The novel supernutrient carotenoid', *International Journal of Health & Allied Sciences*, 3(3), p. 147. doi: 10.4103/2278-344X.138587.

Bjerkeng, B. (2000) 'Carotenoid pigmentation of salmonid fishes—recent progress', *Avances en Nutrición Aculcola V. Memorias del V Simposium Internacional de Nutrición Acuícola.*, (19-22), pp. 71-89.

Blombach, B. and Eikmanns, B. J. (2011) 'Current knowledge on isobutanol production with *Escherichia coli*, *Bacillus subtilis* and *Corynebacterium glutamicum*.', *Bioengineered bugs*, 2(6), pp. 346-350. doi: 10.4161/bbug.2.6.17845.

Blombach, B. and Seibold, G. M. (2010) 'Carbohydrate metabolism in *Corynebacterium glutamicum* and applications for the metabolic engineering of l-lysine production strains', *Applied Microbiology and Biotechnology*, 86(5), pp. 1313-1322. doi: 10.1007/s00253-010-2537-z.

Börmann-El Kholy, E. R., Eikmanns, B. J., Gutmann, M. and Sahm, H. (1993) 'Glutamate dehydrogenase is not essential for glutamate formation by *Corynebacterium glutamicum*', *Applied and Environmental Microbiology*, 59(7), pp. 2329-2331.

Breitmaier, E. and Jung, G. (2012) 'Terpene', in *Organische Chemie: Grundlagen, Verbindungsklassen, Reaktionen, Konzepte, Molekülstruktur, Naturstoffe, Syntheseplanung, Nachhaltigkeit*. 7th edn. Thieme.

Britton, G., Liaaen-Jensen, S. and Pfander, H. (2008) *Carotenoids: Natural Functions*, Birkhauser Basel. doi: 10.1017/CBO09781107415324.004.

Bunch, P. K., Mat-Jan, F., Lee, N. and Clark, D. P. (1997) 'The ldhA gene encoding the fermentative lactate dehydrogenase of *Escherichia coli*.', *Microbiology*, 143 (Pt 1(1 997), pp. 187-195.

Burton, G. W. and Ingold, K. U. (1984) 'Beta-Carotene: An Unusual Type of Lipid Antioxidant', *Science* (New York, N.Y.), 224(4649), pp. 569-73. doi: 10.1126/science.6710156.

Byrne, J. (2014) *Global BioChem to put the brakes on lysine production*. Available at: www.feednavigator.com/Suppliers/Global-BioChem-to-put-the-brakes-on-lysine-production (Accessed: 28 Oct. 2016).

Campbell, N. A. and Reece, J. B. (2009a) 'Die Ernährung der Tiere', in *Biologie*. 8th edn. Pearson Studium, pp. 1211-1241.

Campbell, N. A. and Reece, J. B. (2009b) 'Neurone, Synapsen und Signalgebung', in *Biologie*. 8th edn. Pearson Studium, pp. 1410-1431.

Campbell, N. A. and Reece, J. B. (2009c) 'Photosynthese', in Biologie. 8th edn. München: Pearson Studium, pp. 251-278.

Campbell, N. A. and Reece, J. B. (2016) 'Proteine: Funktionsvielfalt durch Strukturvielfalt', in *Biologie*. 10th edn. Pearson Studium, pp. 94-123.

Choi, S. K., Harada, H., Matsuda, S. and Misawa, N. (2007) 'Characterization of two β-carotene ketolases, CrtO and CrtW, by complementation analysis in *Escherichia coli*', *Applied Microbiology and Biotechnology*, 75(6), pp. 1335-1341. doi: 10.1007/s00253-007-0967-z.

Choi, S. K., Matsuda, S., Hoshino, T., Peng, X. and Misawa, N. (2006) 'Characterization of bacterial β-carotene 3,3'-hydroxylases, CrtZ, and P450 in astaxanthin biosynthetic pathway and adonirubin production by gene combination in *Escherichia coli*', *Applied Microbiology and Biotechnology*, 72(6), pp. 1238-1246. doi: 10.1007/s00253-006-0426-2.

Coryneregnet (no date) OP_cg2672. Available at: coryneregnet.compbio.sdu.dk/v6e/CoryneRegNet/queryElement.php?operon=OP_cg2672 (Accessed: 6 Nov. 2016).

Cremer, J., Eggeling, L. and Sahm, H. (1991) 'Control of the lysine biosynthesis sequence in *Corynebacterium glutamicum* as analyzed by overexpression of the individual corresponding genes', *Applied and Environmental Microbiology*, 57(6), pp. 1746-1752.

Cunningham, F. X. and Gantt, E. (1998) 'GENES AND ENZYMES OF CAROTENOID BIOSYNTHESIS IN PLANTS', *Annu. Rev. Plant Physiol. Plant Mol. Biol*, 49, pp. 557-83. doi: 10.1146/annurev.arplant.49.1.557.

Cunningham, F. X., Pogson, B., Sun, Z., Mcdonald, K. A., Dellapenna, D. and Gantt, E. (1996) 'Functional Analysis of the B and E Lycopene Cyclase Enzymes of *Arabidopsis* Reveals a Mechanism for Control of Cyclic Carotenoid Formation', *The Plant Cell American Society of Plant Physiologists*, 8(September), pp. 1613-1626. doi: 10.1105/tpc.8.9.1613.

Eggeling, L. and Sahm, H. (1999) 'L-glutamate and L-lysine: Traditional products with impetuous developments', *Applied Microbiology and Biotechnology*, 52(2), pp. 146-153. doi: 10.1007/s002530051501.

Eikmanns, B. J., Metzger, M., Reinscheid, D., Kircher, M. and Sahm, H. (1991) 'Amplification of three threonine biosynthesis genes in *Corynebacterium glutamicum* and its influence on carbon flux in different strains', *Applied Microbiology and Biotechnology*, 34(5), pp. 617-622. doi: 10.1007/BF00167910.

Engels, V. and Wendisch, V. F. (2007) 'The DeoR-type regulator SugR represses expression of ptsG in *Corynebacterium glutamicum*', *Journal of Bacteriology*, 189(8), pp. 2955-2966. doi: 10.1128/JB.01596-06.

Fischer, E. (1906) 'Untersuchungen über Aminosäuren, Polypeptide und Proteine', *Berichte der deutschen chemischen Gesellschaft*, 39(1), pp. 530-610. doi: 10.1002/cber.19060390190.

Gassel, S., Schewe, H., Schmidt, I., Schrader, J. and Sandmann, G. (2013) 'Multiple improvement of astaxanthin biosynthesis in *Xanthophyllomyces dendrorhous* by a combination of conventional mutagenesis and metabolic pathway engineering', *Biotechnology Letters*, 35(4), pp. 565-569. doi: 10.1007/s10529-012-1103-4.

Georgi, T., Rittmann, D. and Wendisch, V. F. (2005) 'Lysine and glutamate production by *Corynebacterium glutamicum* on glucose, fructose and sucrose: Roles of malic enzyme and fructose-1,6-bisphosphatase', *Metabolic Engineering*, 7(4), pp. 291-301. doi: 10.1016/j.ymben.2005.05.001.

Giacometti, T. (1979) 'Free and Bound Glutamate in Natural Products', *Glutamic Acid: Advances in biochemistry and physiology*, pp. 25-34.

Global Market Insights (2015) *Beta Carotene Market Size, Industry Analysis Report, Regional Outlook, Application Development Potential, Price Trend, Competitive Market Share & Forecast*, 2016-2023. Available at: www.gminsights.com/industry-analysis/beta-carotene-market (Accessed: 9 Nov. 2016).

Global Market Insights (2016) *Glutamic Acid and Monosodium Glutamate (MSG) Market Size, Potential, Industry Outlook, Regional Analysis, Application Development, Competitive Landscape & Forecast*, 2016-2023. Available at: www.gminsights.com/industry-analysis/glutamic-acid-and-monosodium-glutamate-msg-market- (Accessed: 26 Oct. 2016).

Goldstein, J. L. and Brown, M. S. (1990) 'Regulation of the mevalonate pathway.', *Nature*, 343, pp. 425-430. doi: 10.1038/343425a0.

Goodwin, T. W., C. B. E. and F. R. S. (1980a) 'Biosynthesis of Carotenoids', in *The Biochemistry of the Carotenoids: Volume I Plants*. 2nd edn, pp. 33-76.

Goodwin, T. W., C. B. E. and F. R. S. (1980b) 'Nature and Properties', in *The Biochemistry of the Carotenoids: Volume I Plants*. II. Springer Netherlands, pp. 1-32. doi: 10.1007/978-94-009-5860-9.

Gopinath, V., Meiswinkel, T. M., Wendisch, V. F. and Nampoothiri, K. M. (2011) 'Amino acid production from rice straw and wheat bran hydrolysates by recombinant pentose-utilizing *Corynebacterium glutamicum*', *Applied Microbiology and Biotechnology*, 92(5), pp. 985-996. doi: 10.1007/s00253-011-3478-x.

Grand View Research (2015) *Global Amino Acids Market by Product (L-Glutamate, Lysine, Methionine, Threonine, Tryptophan, Leucine, Iso-Leucine, Valine, Glutamine, Arginine), By Source, By Application Expected to Reach USD 35.40 Billion By 2022*. Available at: www.grandviewresearch.com/press-release/global-amino-acids-market (Accessed: 26 Oct. 2016).

Guerin, M., Huntley, M. E. and Olaizola, M. (2003) '*Haematococcus* astaxanthin: Applications for human health and nutrition', *Trends in Biotechnology*, 21(5), pp. 210-216. doi: 10.1016/S0167-7799(03)00078-7.

Han, J. E. S. (1929) 'Monosodium Glutamate as a Chemical Condiment', *Industrial & Engineering Chemistry*, 21(10), pp. 984-987. doi: 10.1021/ie50238a023.

Harker, M. and Bramley, P. M. (1999) 'Expression of prokaryotic 1-deoxy-D-xylulose-5-phosphatases in *Escherichia coli* increases carotenoid and ubiquinone biosynthesis', *FEBS Lett.*, 448, pp. 115-119. Available at: dx.doi.org/10.1016/S0014-5793(99)00360-9.

Heider, S. A. E., Peters-Wendisch, P., Netzer, R., Stafnes, M., Brautaset, T. and Wendisch, V. F. (2014) 'Production and glucosylation of C50 and C40 carotenoids by metabolically engineered *Corynebacterium glutamicum*', *Applied Microbiology and Biotechnology*, 98(3), pp. 1223-1235. doi: 10.1007/s00253-013-5359-y.

Heider, S. a E., Wolf, N., Hofemeier, A., Peters-Wendisch, P. and Wendisch, V. F. (2014) 'Optimization of the IPP Precursor Supply for the Production of Lycopene, Decaprenoxanthin and Astaxanthin by *Corynebacterium glutamicum*.', *Frontiers in bioengineering and biotechnology*, 2(August), p. 28. doi: 10.3389/fbioe.2014.00028.

Henke, N. A., Heider, S. A. E., Peters-Wendisch, P. and Wendisch, V. F. (2016) 'Production of the marine carotenoid astaxanthin by metabolically engineered *Corynebacterium glutamicum*', *Marine Drugs*, 14(7), p. 124. doi: 10.3390/md14070124.

Hunter, W. N. (2007) 'The non-mevalonate pathway of isoprenoid precursor biosynthesis', *Journal of Biological Chemistry*, 282(30), pp. 21573-21577. doi: 10.1074/jbc.R700005200.

Inui, M., Murakami, S., Okino, S., Kawaguchi, H., Vertés, A. A. and Yukawa, H. (2004) 'Metabolic analysis of *Corynebacterium glutamicum* during lactate and succinate productions under oxygen deprivation conditions', *Journal of Molecular Microbiology and Biotechnology*, 7(4), pp. 182-196. doi: 10.1159/000079827.

Jager, W., Schafer, A., Puhler, A., Labes, G. and Wohlleben, W. (1992) 'Expression of the *Bacillus subtilis* sacB gene leads to sucrose sensitivity in the gram-positive bacterium *Corynebacterium glutamicum* but not in *Streptomyces lividans*', *Journal of Bacteriology*, 174(16), pp. 5462-5465. doi: 0021-9193/92/165462-04$02.00/0.

Kajiwara, S., Kakizono, T., Saito, T., Kondo, K., Ohtani, T., Nishio, N., Nagai, S. and Misawa, N. (1995) 'Isolation and functional identification of a novel cDNA for astaxanthin biosynthesis from *Haematococcus pluvialis*, and astaxanthin synthesis in *Escherichia coli*', *Plant Molecular Biology*, 29(2), pp. 343-352. doi: 10.1007/BF00043657.

Kalinowski, J., Bathe, B., Bartels, D., Bischoff, N., Bott, M., Burkovski, A., Dusch, N., Eggeling, L., Eikmanns, B. J., Gaigalat, L., Goesmann, A., Hartmann, M., Huthmacher, K., Krämer, R., Linke, B., McHardy, A. C., Meyer, F., Möckel, B., Pfefferle, W., Pühler, A., Rey, D. A., Rückert, C., Rupp, O., Sahm, H., Wendisch, V. F., Wiegräbe, I. and Tauch, A. (2003) 'The complete *Corynebacterium glutamicum* ATCC 13032 genome sequence and its impact on the production of L-aspartate-derived amino acids and vitamins', *Journal of Biotechnology*, pp. 5-25. doi: 10.1016/S0168-1656(03)00154-8.

Kalinowski, J., Cremer, J., Bachmann, B., Eggeling, L., Sahm, H. and Puhler, A. (1991) 'Genetic and biochemical analysis of the aspartokinase from *Corynebacterium glutamicum*', *Mol Microbiol*, 5(5), pp. 1197-1204. doi: 10.1111/j.1365-2958.1991.tb01893.x.

Kim, S.-W. and Keasling, J. D. (2001) 'Metabolic engineering of the nonmevalonate isopentenyl diphosphate synthesis pathway in *Escherichia coli* enhances lycopene production', *Biotechnol. Bioeng.*, 72, pp. 408-415. Available at: dx.doi.org/10.1002/1097-0290(20000220)72:4<408::AI D-BIT1003>3.0.CO\n2-H.

Kinoshita, S., KINOSHITA, S., UDAKA, S. and SHIMONO, M. (1957) 'Studies on the Amino Acid Fermentation', *The Journal of General and Applied Microbiology*, 3(3), pp. 193-205. doi: 10.2323/jgam.3.193.

Kinoshita, S., Nakayama, K. and Akita, S. (1958) 'Taxonomical Study of Glutamic Acid Accumulating Bacteria, *Micrococcus glutamicus* nov. sp.', *Bulletin of the Agricultural Chemical Society of Japan*, 22(3), pp. 176-185. doi: 10.1080/03758397.1958.10857463.

Kinoshita, S., Nakayama, K. and Kitada, S. (1958) 'L-LYSINE PRODUCTION USING AUXOTROPH (Preliminary report)', (2), pp. 2-3.

Kirby, J. and Keasling, J. D. (2009) 'Biosynthesis of plant isoprenoids: perspectives for microbial engineering', *Annu Rev Plant Biol*, 60, pp. 335-55. doi: 10.1146/annurev.arplant.043008.091955.

Kircher, M. and Pfefferle, W. (2001) 'The fermentative production of L-lysine as an animal feed additive', *Chemosphere*, 43(1), pp. 27-31. doi: 10.1016/S0045-6535(00)00320-9.

Koller, M., Muhr, A. and Braunegg, G. (2014) 'Microalgae as versatile cellular factories for valued products', *Algal Research*, 6(PA), pp. 52-63. doi: 10.1016/j.algal.2014.09.002.

Krubasik, P., Kobayashi, M. and Sandmann, G. (2001) 'Expression and functional analysis of a gene cluster involved in the synthesis of decaprenoxanthin reveals the mechanisms for C50 carotenoid formation', *European Journal of Biochemistry*, 268(13), pp. 3702-3708. doi: 10.1046/j.1432-1327.2001.02275.x.

Krubasik, P., Takaichi, S., Maoka, T., Kobayashi, M., Masamoto, K. and Sandmann, G. (2001) 'Detailed biosynthetic pathway to decaprenoxanthin diglucoside in *Corynebacterium glutamicum* and identification of novel intermediates', *Archives of Microbiology*, 176(3), pp. 217-223. doi: 10.1007/s002030100315.

Kurihara, K. (2009) 'Glutamate: From discovery as a food flavor to role as a basic taste (umami)', *American Journal of Clinical Nutrition*, 90(3), pp. 1-3. doi: 10.3945/ajcn.2009.27462D.

de la Fuente, J. L., Rodríguez-Sáiz, M., Schleissner, C., Diez, B., Peiro, E. and Barredo, J. L. (2010) 'High-titer production of astaxanthin by the semi-industrial fermentation of *Xanthophyllomyces dendrorhous*', *Journal of Biotechnology*, 148(2-3), pp. 144-146. doi: 10.1016/j.jbiotec.2010.05.004.

Leuchtenberger, W., Huthmacher, K. and Drauz, K. (2005) 'Biotechnological production of amino acids and derivatives: Current status and prospects', *Applied Microbiology and Biotechnology*, 69(1), pp. 1-8. doi: 10.1007/s00253-005-0155-y.

Li, J., Zhu, D., Niu, J., Shen, S. and Wang, G. (2011) 'An economic assessment of astaxanthin production by large scale cultivation of *Haematococcus pluvialis*', *Biotechnology Advances*, pp. 568-574. doi: 10.1016/j.biotechadv.2011.04.001.

Liebl, W. (2005) '*Corynebacterium* Taxonomy', in Eggeling, L. and Bott, M. (eds) *Handbook of Corynebacterium glutamicum*. Boca Raton, Fla.: CRC Press, pp. 9-34. doi: 10.1201/9781420039696.pt2.

Lorenz, R. T. and Cysewski, G. R. (2000) 'Commercial potential for Haematococcus microalgae as a natural source of astaxanthin', *Trends in Biotechnology*, 18(4), pp. 160-167. doi: 10.1016/S0167-7799(00)01433-5.

Lotan, T. and Hirschberg, J. (1995) 'Cloning and expression in *Escherichia coli* of the gene encoding β-C-4-oxygenase, that converts β-carotene to the ketocarotenoid canthaxanthin in *Haematococcus pluvialis*', *FEBS Letters*, 364(2), pp. 125-128. doi: 10.1016/0014-5793(95)00368-J.

Malin, G. M. and Bourd, G. I. (1991) 'Phosphotransferase-dependent glucose transport in *Corynebacterium glutamicum*', *Journal of Applied Bacteriology*. Wiley Online Library, 71(6), pp. 517-523. doi: 10.1111/j.1365-2672.1991.tb03826.x.

Mat-Jan, F., Alam, K. Y. and Clark, D. P. (1989) 'Mutants of *Escherichia coli* deficient in the fermentative lactic dehydrogenase', *J. Bacteriol.*, 171(1), pp. 342-348.

Mazur, R. H. (1984) 'Discovery of Aspartame', in Stegink, L. D. and Filer Jr., L. J. (eds) *Aspartame: Physiology and Biochemistry*. CRC Press, pp. 3-10.

Meiswinkel, T. M., Rittmann, D., Lindner, S. N. and Wendisch, V. F. (2013) 'Crude glycerol-based production of amino acids and putrescine by *Corynebacterium glutamicum*', *Bioresource Technology*, 145, pp. 254-258. doi: 10.1016/j.biortech.2013.02.053.

Meldrum, B. S. (2000) 'Glutamate as a neurotransmitter in the brain: review of physiology and pathology.', *The Journal of nutrition*, 130(4S Suppl), p. 1007S-15S. doi: 10736372.

Mimitsuka, T., Sawai, H., Hatsu, M. and Yamada, K. (2007) 'Metabolic engineering of *Corynebacterium glutamicum* for cadaverine fermentation', *Bioscience, Biotechnology, and Biochemistry*, 71(9), pp. 2130-2135. doi: 10.1271/bbb.60699.

Misawa, N., Kajiwara, S., Kondo, K., Yokoyama, A., Satomi, Y., Saito, T., Miki, W. and Ohtani, T. (1995) 'Canthaxanthin biosynthesis by the conversion of methylene to keto groups in a hydrocarbon beta-carotene by a single gene.', *Biochemical and biophysical research communications*, pp. 867-76. doi: 10.1006/bbrc.1995.1579.

Misawa, N., Satomi, Y., Kondo, K., Yokoyama, A., Kajiwara, S., Saito, T., Ohtani, T. and Miki, W. (1995) 'Structure and functional analysis of a marine bacterial carotenoid biosynthesis gene cluster and astaxanthin biosynthetic pathway proposed at the gene level', *Journal of Bacteriology*, 177(22), pp. 6575-6584.

Mortensen, A. and Skibsted, L. H. (1997) 'Importance of Carotenoid Structure in Radical-Scavenging Reactions', *Journal of Agricultural and Food Chemistry*, 45, pp. 2970-2977. doi: 10.1021/jf970010s.

Mortensen, A., Skibsted, L. H., Sampson, J., Rice-Evans, C. and Everett, S. A. (1997) 'Comparative mechanisms and rates of free radical scavenging by carotenoid antioxidants', *FEBS Letters*. Federation of European Biochemical Societies, 418(1-2), pp. 91-97. doi: 10.1016/S0014-5793(97)01355-0.

Mueller, U. and Huebner, S. (2003) 'Economic aspects of amino acids production.', *Advances in biochemical engineering/biotechnology*, 79, pp. 137-70. Available at: www.ncbi.nlm.nih.gov/pubmed/12523391.

Nakayama, K., Kitada, S. and Kinoshita, S. (1961) 'Studies on Lysine Fermentation I. the Control Mechanism on Lysine Accumulation By Homoserine and Threonine', *The Journal of General and Applied Microbiology*, 7(3), pp. 145-154. Available at: scholar.google.com/scholar?hl=en&btnG=Search&q=intite:J.+Gen.+V+Appl.#6.

Noguchi, N., Niki, E. and Papas, A. (1998) 'Chemistry of Active Oxygen Species and Antioxidants', in Papas, A. M. (ed.) *Antioxidant status, diet, nutrition, and . . .* Boca Raton, Fla.: CRC Press, pp. 3-20.

Norris, S. R., Barrette, T. R. and DellaPenna, D. (1995) 'Genetic dissection of carotenoid synthesis in *Arabidopsis* defines plastoquinone as an essential component of phytoene desaturation.', *The Plant cell*, 7(December), pp. 2139-2149. doi: 10.1105/tpc.7.12.2139.

Olaizola, M. and Huntley, M. E. (2003) 'Recent advances in commercial production of astaxanthin from microalgae', *Recent Advances in Marine Biotechnology. Volume 9: Biomaterials and Bioprocessing.*, 9(JANUARY), pp. 143-164.

Osborne, T. B. and Mendel, L. B. (1914) 'Amino-Acids in Nutrition and Growth', *Journal of Biological Chemistry*, 17, pp. 325-349.

Ovie, S. O. and Eze, S. S. (2011) 'Lysine Requirement and its Effect on the Body Composition of *Oreochromis niloticous* Fingerlings', *Fisheries and Aquatic Science*, 6(2), pp. 186-193. doi: 10.1146/annurev.ecolsys.110308.120220.

Pérez-García, F., Peters-Wendisch, P. and Wendisch, V. F. (2016) 'Engineering *Corynebacterium glutamicum* for fast production of l-lysine and l-pipecolic acid', *Applied Microbiology and Biotechnology*. Applied Microbiology and Biotechnology, 100(18), pp. 8075-8090. doi: 10.1007/s00253-016-7682-6.

Peters-Wendisch, P., Götker, S., Heider, S. A. E., Komati Reddy, G., Nguyen, A. Q., Stansen, K. C. and Wendisch, V. F. (2014) 'Engineering biotin prototrophic *Corynebacterium glutamicum* strains for amino acid, diamine and carotenoid production', *Journal of Biotechnology*. Elsevier B.V., 192(PB), pp. 346-354. doi: 10.1016/j.jbiotec.2014.01.023.

Pfefferle, W., Möckel, B., Bathe, B. and Marx, A. (2003) 'Biotechnological manufacture of lysine.', Advances in biochemical engineering/biotechnology, 79, pp. 59-112. doi: 10.1007/3-540-45989-8_3.

Pfeifer, E., Hünnefeld, M., Popa, O., Polen, T., Kohlheyer, D., Baumgart, M. and Frunzke, J. (2016) 'Silencing of cryptic prophages in *Corynebacterium glutamicum.*', *Nucleic acids research*, pp. 1-15. doi: 10.1093/nar/gkw692.

Porter, J. W. and Anderson, D. G. (1962) 'The biosynthesis of carotenes', *Archives of Biochemistry and Biophysics*, 97(3), pp. 520-528. doi: 10.1146/annurev.pp.18.060167.001213.

Radmacher, E., Stansen, K. C., Besra, G. S., Alderwick, L. J., Maughan, W. N., Hollweg, G., Sahm, H., Wendisch, V. F. and Eggeling, L. (2005) 'Ethambutol, a cell wall inhibitor of *Mycobacterium tuberculosis*, elicits L-glutamate efflux of *Corynebacterium glutamicum*', *Microbiology*, 151(5), pp. 1359-1368. doi: 10.1099/mic.0.27804-0.

Reardon, J. E. and Abeles, R. H. (1986) 'Mechanism of action of isopentenyl pyrophosphate isomerase: evidence for a carbonium ion intermediate.', Biochemistry, 25(19), pp. 5609-16. doi: 10.1021/bi00367a040.

Rodríguez-Concepción, M. and Boronat, A. (2002) 'Elucidation of the methylerythritol phosphate pathway for isoprenoid biosynthesis in bacteria and plastids. A metabolic milestone achieved through genomics.', *Plant physiology*, 130(3), pp. 1079-1089. doi: 10.1104/pp.007138.

Ronen, G., Cohen, M., Zamir, D. and Hirschberg, J. (1999) 'Regulation of carotenoid biosynthesis during tomato fruit development: expression of the gene for lycopene epsilon cyclase is down-regulated during ripening and is elevated in the mutant Delta.', *The Plant Journal*, 17(4), pp. 341-351. doi: 10.1046/j.1365-313X.1999.00381.x.

Sahm, H., Antranikian, G., Stahmann, K.-P. and Takors, R. (2013) 'Aminosäuren', in *Industrielle Mikrobiologie*. Springer Spektrum, pp. 109-126.

Sakai, S., Tsuchida, Y., Okino, S., Ichihashi, O., Kawaguchi, H., Watanabe, T., Inui, M. and Yukawa, H. (2007) 'Effect of lignocellulose-derived inhibitors on growth of and ethanol production by growth-arrested *Corynebacterium glutamicum* R', *Applied and Environmental Microbiology*, 73(7), pp. 2349-2353. doi: 10.1128/AEM.02880-06.

Sandmann, G. and Yukawa, H. (2005) 'Vitamin synthesis: carotenoids, biotin and pantothenate. In Handbook of *Corynebacterium glutamicum.*', in Eggeling, L. and Bott, M. (eds) *CRC express journal*. Boca Raton, Fla.: CRC Press, pp. 399-417.

Schäfer, A., Tauch, A., Jäger, W., Kalinowski, J., Thierbach, G. and Pühler, A. (1994) 'Small mobilizable multi-purpose cloning vectors derived from the *Escherichia coli* plasmids pK18 and pK19: selection of defined deletions in the chromosome of *Corynebacterium glutamicum*', Gene, 145(1), pp. 69-73. doi: 10.1016/0378-1119(94)90324-7.

Schneider, J. and Wendisch, V. F. (2010) 'Putrescine production by engineered *Corynebacterium glutamicum*', Applied Microbiology and Biotechnology, 88(4), pp. 859-868. doi: 10.1007/s00253-010-2778-x.

Schneider, J., Niermann, K., Wendisch, V. F., 2011. Production of the amino acids L-glutamate, L-lysine, L-ornithine and L-arginine from arabinose by recombinant *Corynebacterium glutamicum*. J. Biotechnol. 154 (2-3), 191-198. Schrumpf, B., Eggeling, L. and Sahm, H. (1992) 'Isolation and prominent characteristics of an L-lysine hyperproducing strain of *Corynebacterium glutamicum*', Applied Microbiology and Biotechnology, 37(5), pp. 566-571. doi: 10.1007/BF00240726.

Seibold, G., Auchter, M., Berens, S., Kalinowski, J. and Eikmanns, B. J. (2006) 'Utilization of soluble starch by a recombinant *Corynebacterium glutamicum* strain: Growth and lysine production', Journal of Biotechnology, 124(2), pp. 381-391. doi: 10.1016/j.jbiotec.2005.12.027.

Seibold, G. M., Wurst, M. and Eikmanns, B. J. (2009) 'Roles of maltodextrin and glycogen phosphorylases in maltose utilization and glycogen metabolism in *Corynebacterium glutamicum*', Microbiology, 155(2), pp. 347-358. doi: 10.1099/mic.0.023614-0.

Shiio, B. I., Otsuka, S. and Takahashi, M. (1962) 'Effect of Biotin on the Bacterial Formation of Glutamic Acid As the biotin concentration in the culture Effect of Biotin on Glutamate Formation medium increased, the amount of L-glutamate produced in the medium decreased, but the of glutamate in the ace', 51(1).

Simon, R., Priefer, U. and Puhler, A. (1983) 'A Broad Host Range Mobilization System for In Vivo Genetic Engineering: Transposon Mutagenesis in Gram Negative Bacteria', Nat Biotechnol, 1(9), pp. 784-789. doi: 10.1038/nbt1183-784.

Song, Y., Matsumoto, K., Tanaka, T., Kondo, A. and Taguchi, S. (2013) 'Single-step production of polyhydroxybutyrate from starch by using α-amylase cell-surface displaying system of *Corynebacterium glutamicum*', Seibutsu-kogaku Kaishi, 115(1), pp. 12-14. doi: 10.1016/j.jbiosc.2012.08.004.

Spektrum-Lexikon der Biochemie (1999) Astaxanthin. Available at: www.spektrum.de/lexikon/biochemie/astaxanthin/609 (Accessed: 18 Oct. 2016).

Spektrum-Lexikon der Biologie (1999a) Astaxanthin. Available at: www.spektrum.de/lexikon/biologie/astaxanthin/5587 (Accessed: 18 Oct. 2016).

Spektrum-Lexikon der Biologie (1999b) Lysin. Available at: www.spektrum.de/lexikon/biologie/lysin/40375 (Accessed: 31 Oct. 2016).

Spektrum-Lexikon der Biologie (1999c) Minimumgesetz. Available at: www.spektrum.de/lexikon/biologie/minimumgesetz/43184 (Accessed: 7 Nov. 2016).

Spektrum-Lexikon der Chemie (1998) Lysin. Available at: www.spektrum.de/lexikon/chemie/l-lysin/5499 (Accessed: 31 Oct. 2016).

Sutcliffe, J. G. (1979) 'Complete nucleotide sequence of the *Escherichia coli* plasmid pBR322', Cold Spring Harbor Symposia on Quantitative Biology, 43(1), pp. 77-90. doi: 10.1101/SQB.1979.043.01.013.

Thulasiram, H. V, Erickson, H. K. and Poulter, C. D. (2007) 'Chimeras of Two Isoprenoid Synthases in Isoprenoid Biosynthesis', Science, 73(2007), pp. 73-76. doi: 10.1126/science.1137786.

Tobias, A. V. and Arnold, F. H. (2006) 'Biosynthesis of novel carotenoid families based on unnatural carbon backbones: A model for diversification of natural product pathways', Biochimica et Biophysica Acta (BBA)—Molecular and Cell Biology of Lipids, 1761(2), pp. 235-246. doi: 10.1016/j.bbalip.2006.01.003.

Tsuchidate, T., Tateno, T., Okai, N., Tanaka, T., Ogino, C. and Kondo, A. (2011) 'Glutamate production from β-glucan using endoglucanase-secreting *Corynebacterium glutamicum*', Applied Microbiology and Biotechnology, 90(3), pp. 895-901. doi: 10.1007/s00253-011-3116-7.

Uhde, A., Youn, J. W., Maeda, T., Clermont, L., Matano, C., Krämer, R., Wendisch, V. F., Seibold, G. M. and Marin, K. (2013) 'Glucosamine as carbon source for amino acid-producing *Corynebacterium glutamicum*', Applied Microbiology and Biotechnology, 97(4), pp. 1679-1687. doi: 10.1007/s00253-012-4313-8.

Unthan, S., Baumgart, M., Radek, A., Herbst, M., Siebert, D., Brihl, N., Bartsch, A., Bott, M., Wiechert, W., Marin, K., Hans, S., Krämer, R., Seibold, G., Frunzke, J., Kalinowski, J., Rickert, C., Wendisch, V. F. and Noack, S. (2015) 'Chassis organism from *Corynebacterium glutamicum*—a top-down approach to identify and delete irrelevant gene clusters', Biotechnology Journal, 10(2), pp. 290-301. doi: 10.1002/biot.201400041.

Vershinin, A. (1999) 'Biological functions of carotenoids—diversity and evolution', BioFactors (Oxford, England), 10(2-3), pp. 99-104. doi: 10.1002/biof.5520100203.

Wendisch, V. F., Jorge, J. M., Perez-Garcia, F., Sgobba, E., 2016b. Updates on industrial production of amino acids using *Corynebacterium glutamicum*. World J. Microbiol. Biotechnol. 32 (6), 105.

Wink, M. (2011) 'Biokatalyse in der chemischen Industrie: Konzepte, Methoden und Anwendungen', in Molekulare Biotechnologie. 2nd edn. Weinheim: Wiley-VCH, pp. 481-504.

Wisniewska, A. and Subczynski, W. K. (1998) 'Effects of polar carotenoids on the shape of the hydrophobic barrier of phospholipid bilayers', Biochimica et Biophysica Acta—Biomembranes, 1368(2), pp. 235-246. doi: 10.1016/S0005-2736(97)00182-X.

Wu, G. (2009) 'Amino acids: Metabolism, functions, and nutrition', Amino Acids, 37(1), pp. 1-17. doi: 10.1007/s00726-009-0269-0.

Yokota, A. and Lindley, N. (2005) 'Central Metabolism: Sugar Uptake and Conversion.', in Eggeling, L. and Bott, M. (eds) Handbook of Corynebacterium glutamicum. Boca Raton, Fla.: CRC Press, pp. 215-240. doi: 10.1201/9781420039696.pt5.

The invnetion claimed is:

1. A process for the preparation of astaxanthin and lysine in recombinant *C. glutamicum*, wherein the genome of said recombinant *C. glutamicum* comprises a deletion in the endogenous crtR, crtY and crtEb genes, and wherein said recombinant *C. glutamicum* has been genetically modified to introduce crtE, crtB, and crtI genes from *C. glutamicum*, a crtY from *P. ananatis*, at least one recombinant gene encoding a crtZ-protein from *F. pelagi, B. bacteroides, S. astaxanthinifaciens*, or *B. vesicularis*, and at least one recombinant gene encoding a crtW-protein from *F. pelagi, B. aurantiaca, S. astaxanthinifaciens, B. bacteroides*, or *B. vesicularis*.

2. The process according to claim 1, wherein the gene encoding the crtZ-protein comprises a nucleic acid sequence selected from the group consisting of SEQ ID NO: 1, 13, 15 and 17, or
   wherein the crtZ-protein encoded by the gene encoding the crtZ-protein has an amino acid sequence selected from the group consisting of SEQ ID NO: 2, 14, 16 and 18.

3. The process according to claim 2, wherein the gene encoding the crtZ-protein comprises the nucleic acid sequence of SEQ ID NO: 1.

4. The process according to claim 1, wherein the gene encoding the crtW-protein comprises a nucleic acid sequence selected from the group consisting of SEQ ID NO: 3, 5, 7, 9, 11, 19 and 21.

5. The process according to claim 1, wherein the crtW-protein encoded by the gene encoding the crtW-protein comprises an amino acid sequence selected from the group consisting of SEQ ID NO: 4, 6, 8, 10, 12, 20 and 22.

6. The process according to claim 1, wherein said recombinant *C. glutamicum* comprises a first promoter which is operably linked to the gene encoding the crtZ-protein.

7. The process according to claim 6, wherein said recombinant *C. glutamicum* comprises a second promoter which is operably linked to the gene encoding the crtW-protein.

8. The process according to claim 7, wherein the first promoter is induced by a first inducing compound and the second promoter is induced by a second inducing compound, wherein the first and second inducing compounds are not the same inducing compound.

9. The process according to claim 7, wherein the second promoter is a constitutively expressing promoter.

10. The process according to claim 7, wherein induction of the first promoter and induction of the second promoter occur at different times.

11. The process according to claim 7, wherein induction of promoter activity of the first promoter occurs at the beginning of the cultivation, in the exponential growth phase within the first 6 hours.

12. The process according to claim 7, wherein the first promoter and the second promoter are constitutively expressing promoters.

13. The process according to claim 1, wherein said recombinant *C. glutamicum* has a deletion in the endogenous sugR and IdhA genes.

* * * * *

SEQUENCE LISTING

<160> NUMBER OF SEQ ID NOS: 91

<210> SEQ ID NO 1
<211> LENGTH: 540
<212> TYPE: DNA
<213> ORGANISM: Fulvimarina pelagi

<400> SEQUENCE: 1

```
atgacgatct ggactctcta ctacgtctgt ctcaccctcg tcacgatcgg tttgatggag      60
gtttatgcat ggtgggcgca caagttcatc atgcatggca aattcggttg gggctggcat     120
aagtcccacc acgaggaaac cgaagggtgg ttcgagaaga acgatctcta cgctgtcgtt     180
ttcgccggct tcgcgatagc gctgttcatg gtcggacatt tcctttctcc gaccctgctc     240
gccatcgcct ggggcatcac gctttacgga ttactctact cgttgcccca tgatggactt     300
gtccatcagc gctggccgtt caactacgtg ccgcatcgag gttatgcaaa acgcctggtt     360
caagctcatc gtctgcacca tgcggtggaa ggccgcgagc actgcgtctc gttcggcttt     420
ctctatgcgc cgccgattga aaagctgaag cgcgatttgc gtgagtccgg aattctcgaa     480
cgggagcgca tcgagcggtc tctggaccag caaggctccg cccacgcgcc ggttcggtaa     540
```

<210> SEQ ID NO 2
<211> LENGTH: 179
<212> TYPE: PRT
<213> ORGANISM: Fulvimarina pelagi

<400> SEQUENCE: 2

```
Met Thr Ile Trp Thr Leu Tyr Tyr Val Cys Leu Thr Leu Val Thr Ile
1               5                   10                  15

Gly Leu Met Glu Val Tyr Ala Trp Trp Ala His Lys Phe Ile Met His
            20                  25                  30

Gly Lys Phe Gly Trp Gly Trp His Lys Ser His His Glu Glu Thr Glu
        35                  40                  45

Gly Trp Phe Glu Lys Asn Asp Leu Tyr Ala Val Val Phe Ala Gly Phe
    50                  55                  60

Ala Ile Ala Leu Phe Met Val Gly His Phe Leu Ser Pro Thr Leu Leu
65                  70                  75                  80

Ala Ile Ala Trp Gly Ile Thr Leu Tyr Gly Leu Leu Tyr Phe Val Ala
                85                  90                  95

His Asp Gly Leu Val His Gln Arg Trp Pro Phe Asn Tyr Val Pro His
            100                 105                 110

Arg Gly Tyr Ala Lys Arg Leu Val Gln Ala His Arg Leu His His Ala
        115                 120                 125

Val Glu Gly Arg Glu His Cys Val Ser Phe Gly Phe Leu Tyr Ala Pro
    130                 135                 140

Pro Ile Glu Lys Leu Lys Arg Asp Leu Arg Glu Ser Gly Ile Leu Glu
145                 150                 155                 160

Arg Glu Arg Ile Glu Arg Ser Leu Asp Gln Gln Gly Ser Ala His Ala
                165                 170                 175

Pro Val Arg
```

<210> SEQ ID NO 3
<211> LENGTH: 789
<212> TYPE: DNA
<213> ORGANISM: Fulvimarina pelagi

<400> SEQUENCE: 3

```
atgaccctca gcccaacctc acgcctgatc ccggcaagtg cgttaccgcg atccacaccc    60
gccgactcac ccaaaatcag accctaccaa acgacgattg gcctgacgct ctgtgccgtg   120
ctgctggcat cgtggttcgc aatacacgtc tcagcgatat tcttcctcga catcaatttc   180
agcacgttgc ctctcgcacc attgatcacg gtgttccagt gctggttgac ggtgggggctt   240
ttcatcctgg ctcacgacgc catgcatggt tcgctggcgc cgggtcgaac gcgtttgaat   300
gccgtaatcg gcgggttcat cctgttcgtc tacgcggat ttgcgtggaa aaagatcaga   360
gatgctcact tcgcacacca cgacgcaccc ggtacaccgg ccgacccgga tttctacgca   420
gatgatccgg agaatttctg gccttggttc ggcaccttct tctcacgtta tttcggatgg   480
agatcggtcg cattcgtctc gaccgtcgtg acgttttatc tcgtcatact ggatgcatct   540
gtgacgaacg tggttctatt ttacggcttg ccgtcactgc tttcgtcatt gcagctcttc   600
tacttcggaa cctaccgccc gcatcgacac gaagaatcgg gcacctttgc cgacgcgcat   660
aacacacgtt cgagcgaatt cggttacgtg gcctcgctat tctcctgctt ccatttggc   720
taccaccatg agcaccattt ggcgccatgg acgccttggt gggctctgcc gcatactcgc   780
cagtcctaa                                                            789
```

<210> SEQ ID NO 4
<211> LENGTH: 262
<212> TYPE: PRT
<213> ORGANISM: Fulvimarina pelagi

<400> SEQUENCE: 4

```
Met Thr Leu Ser Pro Thr Ser Arg Leu Ile Pro Ala Ser Ala Leu Pro
1               5                   10                  15

Arg Ser Thr Pro Ala Asp Ser Pro Lys Ile Arg Pro Tyr Gln Thr Thr
                20                  25                  30

Ile Gly Leu Thr Leu Cys Ala Val Leu Leu Ala Ser Trp Phe Ala Ile
            35                  40                  45

His Val Ser Ala Ile Phe Phe Leu Asp Ile Asn Phe Ser Thr Leu Pro
        50                  55                  60

Leu Ala Pro Leu Ile Thr Val Phe Gln Cys Trp Leu Thr Val Gly Leu
65                  70                  75                  80

Phe Ile Leu Ala His Asp Ala Met His Gly Ser Leu Ala Pro Gly Arg
                85                  90                  95

Thr Arg Leu Asn Ala Val Ile Gly Gly Phe Ile Leu Phe Val Tyr Ala
                100                 105                 110

Gly Phe Ala Trp Lys Lys Ile Arg Asp Ala His Phe Ala His His Asp
            115                 120                 125

Ala Pro Gly Thr Pro Ala Asp Pro Asp Phe Tyr Ala Asp Asp Pro Glu
        130                 135                 140

Asn Phe Trp Pro Trp Phe Gly Thr Phe Phe Ser Arg Tyr Phe Gly Trp
145                 150                 155                 160

Arg Ser Val Ala Phe Val Ser Thr Val Val Thr Phe Tyr Leu Val Ile
                165                 170                 175

Leu Asp Ala Ser Val Thr Asn Val Val Leu Phe Tyr Gly Leu Pro Ser
            180                 185                 190

Leu Leu Ser Ser Leu Gln Leu Phe Tyr Phe Gly Thr Tyr Arg Pro His
        195                 200                 205

Arg His Glu Glu Ser Gly Thr Phe Ala Asp Ala His Asn Thr Arg Ser
    210                 215                 220

Ser Glu Phe Gly Tyr Val Ala Ser Leu Phe Ser Cys Phe His Phe Gly
```

```
225                 230                 235                 240
Tyr His His Glu His His Leu Ala Pro Trp Thr Pro Trp Trp Ala Leu
                245                 250                 255

Pro His Thr Arg Gln Ser
            260
```

<210> SEQ ID NO 5
<211> LENGTH: 714
<212> TYPE: DNA
<213> ORGANISM: Fulvimarina pelagi

<400> SEQUENCE: 5

```
atgagaccct accaaacgac gattggcctg acgctctgtg ccgtgctgct ggcatcgtgg    60
ttcgcaatac acgtctcagc gatattcttc ctcgacatca atttcagcac gttgcctctc   120
gcaccattga tcacggtgtt ccagtgctgg ttgacggtgg ggcttttcat cctggctcac   180
gacgccatgc atggttcgct ggcgccgggt cgaacgcgtt tgaatgccgt aatcggcggg   240
ttcatcctgt tcgtctacgc gggatttgcg tggaaaaaga tcagagatgc tcacttcgca   300
caccacgacg cacccggtac accggccgac ccggatttct acgcagatga tccggagaat   360
ttctggcctt ggttcggcac cttcttctca cgttatttcg gatggagatc ggtcgcattc   420
gtctcgaccg tcgtgacgtt ttatctcgtc atactggatg catctgtgac gaacgtggtt   480
ctattttacg gcttgccgtc actgctttcg tcattgcagc tcttctactt cggaacctac   540
cgcccgcatc gacacgaaga tcgggcacc tttgccgacg cgcataacac acgttcgagc   600
gaattcggtt acgtggcctc gctattctcc tgcttccatt ttggctacca ccatgagcac   660
catttggcgc catggacgcc ttggtgggct ctgccgcata tcgccagtc ctaa          714
```

<210> SEQ ID NO 6
<211> LENGTH: 237
<212> TYPE: PRT
<213> ORGANISM: Fulvimarina pelagi

<400> SEQUENCE: 6

```
Met Arg Pro Tyr Gln Thr Thr Ile Gly Leu Thr Leu Cys Ala Val Leu
1               5                   10                  15

Leu Ala Ser Trp Phe Ala Ile His Val Ser Ala Ile Phe Phe Leu Asp
            20                  25                  30

Ile Asn Phe Ser Thr Leu Pro Leu Ala Pro Leu Ile Thr Val Phe Gln
        35                  40                  45

Cys Trp Leu Thr Val Gly Leu Phe Ile Leu Ala His Asp Ala Met His
    50                  55                  60

Gly Ser Leu Ala Pro Gly Arg Thr Arg Leu Asn Ala Val Ile Gly Gly
65                  70                  75                  80

Phe Ile Leu Phe Val Tyr Ala Gly Phe Ala Trp Lys Lys Ile Arg Asp
                85                  90                  95

Ala His Phe Ala His His Asp Ala Pro Gly Thr Pro Ala Asp Pro Asp
            100                 105                 110

Phe Tyr Ala Asp Asp Pro Glu Asn Phe Trp Pro Trp Phe Gly Thr Phe
        115                 120                 125

Phe Ser Arg Tyr Phe Gly Trp Arg Ser Val Ala Phe Val Ser Thr Val
    130                 135                 140

Val Thr Phe Tyr Leu Val Ile Leu Asp Ala Ser Val Thr Asn Val Val
145                 150                 155                 160

Leu Phe Tyr Gly Leu Pro Ser Leu Leu Ser Ser Leu Gln Leu Phe Tyr
```

```
                165                 170                 175
Phe Gly Thr Tyr Arg Pro His Arg His Glu Glu Ser Gly Thr Phe Ala
            180                 185                 190

Asp Ala His Asn Thr Arg Ser Ser Glu Phe Gly Tyr Val Ala Ser Leu
            195                 200                 205

Phe Ser Cys Phe His Phe Gly Tyr His His Glu His Leu Ala Pro
    210                 215                 220

Trp Thr Pro Trp Trp Ala Leu Pro His Thr Arg Gln Ser
225                 230                 235

<210> SEQ ID NO 7
<211> LENGTH: 735
<212> TYPE: DNA
<213> ORGANISM: Brevundimonas aurantiaca

<400> SEQUENCE: 7
atgaccgccg ccgtcgccga gccacgcacc gtcccgcgcc agacctggat cggtctgacc     60
ctggcgggaa tgatcgtggc gggatgggcg gttctgcatg tctacggcgt ctatttcac    120 cgatggggc cgttgaccct ggtgatcgcc ccggcgatcg tggcggtcca gacctggttg    180
tcggtcggcc ttttcatcgt cgcccatgac gccatgcacg gctccctggc gccgggacgg    240
ccgcggctga acgccgcagt cggccggctg accctggggc tctatgcggg cttccgcttc    300
gatcggctga agacggcgca ccacgcccac acgccgcgcc ccggcacggc cgacgacccg    360
gattttcacg ccccggcgcc ccgcgccttc cttccctggt cctgaacttc tttcgcacc    420 tatttcggct ggcgcgagat ggcggtcctg accgccctgg tcctgatcgc cctcttcggc    480
ctgggggcgc ggccggccaa tctcctgacc ttctgggccg cgccggccct gctttcagcg    540
cttcagctct tcaccttcgg cacctggctg ccgcaccgcc acaccgacca gccgttcgcc    600
gacgcgcacc acgcccgcag cagcggctac ggccccgtgc tttccctgct cacctgtttc    660
cacttcggcc gccaccacga acaccatctg agccctggc ggccctggtg gcgtctgtgg    720
cgcggcgagt cttga                                                     735

<210> SEQ ID NO 8
<211> LENGTH: 244
<212> TYPE: PRT
<213> ORGANISM: Brevundimonas aurantiaca

<400> SEQUENCE: 8

Met Thr Ala Ala Val Ala Glu Pro Arg Thr Val Pro Arg Gln Thr Trp
1               5                   10                  15

Ile Gly Leu Thr Leu Ala Gly Met Ile Val Ala Gly Trp Ala Val Leu
            20                  25                  30

His Val Tyr Gly Val Tyr Phe His Arg Trp Gly Pro Leu Thr Leu Val
        35                  40                  45

Ile Ala Pro Ala Ile Val Ala Val Gln Thr Trp Leu Ser Val Gly Leu
    50                  55                  60

Phe Ile Val Ala His Asp Ala Met His Gly Ser Leu Ala Pro Gly Arg
65                  70                  75                  80

Pro Arg Leu Asn Ala Ala Val Gly Arg Leu Thr Leu Gly Leu Tyr Ala
                85                  90                  95

Gly Phe Arg Phe Asp Arg Leu Lys Thr Ala His His Ala His His Ala
            100                 105                 110

Ala Pro Gly Thr Ala Asp Asp Pro Asp Phe His Ala Pro Ala Pro Arg
        115                 120                 125
```

Ala Phe Leu Pro Trp Phe Leu Asn Phe Phe Arg Thr Tyr Phe Gly Trp
        130                 135                 140

Arg Glu Met Ala Val Leu Thr Ala Leu Val Leu Ile Ala Leu Phe Gly
145                 150                 155                 160

Leu Gly Ala Arg Pro Ala Asn Leu Leu Thr Phe Trp Ala Ala Pro Ala
                165                 170                 175

Leu Leu Ser Ala Leu Gln Leu Phe Thr Phe Gly Thr Trp Leu Pro His
            180                 185                 190

Arg His Thr Asp Gln Pro Phe Ala Asp Ala His His Ala Arg Ser Ser
        195                 200                 205

Gly Tyr Gly Pro Val Leu Ser Leu Leu Thr Cys Phe His Phe Gly Arg
    210                 215                 220

His His Glu His His Leu Ser Pro Trp Arg Pro Trp Trp Arg Leu Trp
225                 230                 235                 240

Arg Gly Glu Ser

<210> SEQ ID NO 9
<211> LENGTH: 750
<212> TYPE: DNA
<213> ORGANISM: Sphingomonas astaxanthinifaciens

<400> SEQUENCE: 9
atggccccca tgctcagtga cgcgcagcgc cgccgccagg cgatgatcgg gctcggcctc      60
gccgccgcga tcaccgccgc cttcgtcgcg ctgcatgtct ggtcggtctt cttcctgccg     120
ctcgagggcg cgggctggtg gctcgcgctg ccgatcgtcg cggtgcagac ctggctcagc     180
gtcggcctgt tcatcgtcgc gcatgacgcg atgcacggca gcctcgcgcc gggccgcccg     240
gcgaccaacc tcttctgggg gcggctgacg ctgctgctct acgcgggctt ctggttggac     300
cgccttttcg ccaagcattt cgaccaccac cgccatgtcg ggaccgagcg cgatcccgat     360
ttctcggtcg atcatccgac ccgcttctgg ccctggtatt atgccttcat gcggcgctat     420
ttcgggcttc gcgaatatct ggtgctgaac gcgctggtgc tggcctacgt gctggtgctg     480
aaggcgccgc tcggcaatct gctcctgttc tgggcgctgc cctcgatcct gtcctcgatc     540
cagctcttct atttcggcac ctaccttccg caccggcacg aggacgcgcc cttcgccgac     600
cagcacaatg cccgcagcaa cgactttccg gtctggctgt cgctgctgac ctgcttccac     660
ttcggctatc accgcgagca tcacctcagc cccggcaccc cctggtggca gctgccccgg     720
cggcggcgcg agcttgcgct tcccgcctaa                                      750

<210> SEQ ID NO 10
<211> LENGTH: 249
<212> TYPE: PRT
<213> ORGANISM: Sphingomonas astaxanthinifaciens

<400> SEQUENCE: 10

Met Ala Pro Met Leu Ser Asp Ala Gln Arg Arg Gln Ala Met Ile
1               5                   10                  15

Gly Leu Gly Leu Ala Ala Ala Ile Thr Ala Ala Phe Val Ala Leu His
            20                  25                  30

Val Trp Ser Val Phe Phe Leu Pro Leu Glu Gly Ala Gly Trp Trp Leu
        35                  40                  45

Ala Leu Pro Ile Val Ala Val Gln Thr Trp Leu Ser Val Gly Leu Phe
    50                  55                  60

Ile Val Ala His Asp Ala Met His Gly Ser Leu Ala Pro Gly Arg Pro

```
                65                  70                  75                  80
Ala Thr Asn Leu Phe Trp Gly Arg Leu Thr Leu Leu Tyr Ala Gly
                    85                  90                  95

Phe Trp Leu Asp Arg Leu Ser Pro Lys His Phe Asp His Arg His
                100                 105                 110

Val Gly Thr Glu Arg Asp Pro Asp Phe Ser Val Asp His Pro Thr Arg
            115                 120                 125

Phe Trp Pro Trp Tyr Tyr Ala Phe Met Arg Arg Tyr Phe Gly Leu Arg
        130                 135                 140

Glu Tyr Leu Val Leu Asn Ala Leu Val Leu Ala Tyr Val Leu Val Leu
145                 150                 155                 160

Lys Ala Pro Leu Gly Asn Leu Leu Phe Trp Ala Leu Pro Ser Ile
                165                 170                 175

Leu Ser Ser Ile Gln Leu Phe Tyr Phe Gly Thr Tyr Leu Pro His Arg
            180                 185                 190

His Glu Asp Ala Pro Phe Ala Asp Gln His Asn Ala Arg Ser Asn Asp
        195                 200                 205

Phe Pro Val Trp Leu Ser Leu Leu Thr Cys Phe His Phe Gly Tyr His
    210                 215                 220

Arg Glu His His Leu Ser Pro Gly Thr Pro Trp Trp Gln Leu Pro Arg
225                 230                 235                 240

Arg Arg Arg Glu Leu Ala Leu Pro Ala
                245
```

<210> SEQ ID NO 11
<211> LENGTH: 738
<212> TYPE: DNA
<213> ORGANISM: Brevundimonas bacteroides

<400> SEQUENCE: 11

```
atgacgcggg aacgccagac cgtcgtcggc ctgacgctgg ccgccgtcat cgtgggcggc      60
tggatgacgc tgcacgtctg gggcgtgttc tttcagccgc tgtcgggaac agcgctgttc     120
gtggtcccgc tgctgatcct gacccagagc tggctcggtg cgggcatgtt catcgtcgcc     180
catgacgcca tgcacggttc actggccccc ggtcgccccc gcctcaacgc cgtgatcggc     240
cagatctgcg tcggggccta tgcggccttc tcgtatcgca agctgaacgt ctgccaccac     300
cagcaccacc gcgcgccggg cacggccgag accccgact  tccatgccga gcggcccgag     360
gccttcctgc cgtggttcta tggcttcttc acccgatact tcggctggcg cgagttcacg     420
atcgtgacgg cggtgctgat cgcctatctg ctgatcgggg cgacggtggt gaacctgatc     480
ctgttctggg ccgtgcccgc ggtcctcagt gcgctccagc tgttcgtgtt cgggaccctgg    540
ctgccgcatc ggcatacggc gggcgacggg ttcgcggatc atcaccatgc gcggacgatc     600
ccgatgccgt gggtcgcgtc gcttctggcc tgcttccact cggaatgca  tcacgagcac     660
cacctgacgc agccgcgcc  ttggtggaga ctgcctgagg ttcgaaaggc tatgctggcg     720
cgtagcgaac gtctctaa                                                   738
```

<210> SEQ ID NO 12
<211> LENGTH: 245
<212> TYPE: PRT
<213> ORGANISM: Brevundimonas bacteroides

<400> SEQUENCE: 12

```
Met Thr Arg Glu Arg Gln Thr Val Val Gly Leu Thr Leu Ala Ala Val
1               5                   10                  15
```

Ile Val Gly Gly Trp Met Thr Leu His Val Trp Gly Val Phe Phe Gln
            20                  25                  30

Pro Leu Ser Gly Thr Ala Leu Phe Val Val Pro Leu Leu Ile Leu Thr
        35                  40                  45

Gln Ser Trp Leu Gly Ala Gly Met Phe Ile Val Ala His Asp Ala Met
 50                  55                  60

His Gly Ser Leu Ala Pro Gly Arg Pro Arg Leu Asn Ala Val Ile Gly
 65                  70                  75                  80

Gln Ile Cys Val Gly Ala Tyr Ala Ala Phe Ser Tyr Arg Lys Leu Asn
                 85                  90                  95

Val Cys His His Gln His Arg Ala Pro Gly Thr Ala Glu Asp Pro
            100                 105                 110

Asp Phe His Ala Glu Arg Pro Glu Ala Phe Leu Pro Trp Phe Tyr Gly
        115                 120                 125

Phe Phe Thr Arg Tyr Phe Gly Trp Arg Glu Phe Thr Ile Val Thr Ala
130                 135                 140

Val Leu Ile Ala Tyr Leu Leu Ile Gly Ala Thr Val Val Asn Leu Ile
145                 150                 155                 160

Leu Phe Trp Ala Val Pro Ala Val Leu Ser Ala Leu Gln Leu Phe Val
                165                 170                 175

Phe Gly Thr Trp Leu Pro His Arg His Thr Ala Gly Asp Gly Phe Ala
            180                 185                 190

Asp His His His Ala Arg Thr Ile Pro Met Pro Trp Val Ala Ser Leu
        195                 200                 205

Leu Ala Cys Phe His Phe Gly Met His His Glu His Leu Thr Pro
210                 215                 220

Ala Ala Pro Trp Trp Arg Leu Pro Glu Val Arg Lys Ala Met Leu Ala
225                 230                 235                 240

Arg Ser Glu Arg Leu
                245

<210> SEQ ID NO 13
<211> LENGTH: 504
<212> TYPE: DNA
<213> ORGANISM: Brevundimonas bacteroides

<400> SEQUENCE: 13
atgacgatcg tctggttcac cctgctgacg ctggccgtct tcttcctcat ggaaggggtc      60
gcctggacaa cgcaccgcta catcatgcat gggccgctcg gctggggctg caccgcgat     120 caccatgagc cgcacgacaa gaccttcgag gtcaacgacc tctatggcgt ggtcggggcc    180
gtggtcggga ccggtctgtt cgtcgtcgcc tggttgacgg acctttggtg ggtgcgggcg    240
accgcactgg gcgtcacgct gtacggcgtg gtctacgcct cgtgcacga cggcctggtg    300 caccagcgat ggccgttcca ctggatgccg aagaacggtt atgcgcggag ctggttcag    360 gcgcacaagc tgcatcacgc ggttcagacg cgcgatgggg ccgtgtcgtt cggcttcgtc    420
ttcgcgccaa accccagcg gctcagcgcc atcctgaagg cgcgccgggc agagcgcgcc    480
gcgacggaca tcccggccga gtaa                                           504

<210> SEQ ID NO 14
<211> LENGTH: 167
<212> TYPE: PRT
<213> ORGANISM: Brevundimonas bacteroides

<400> SEQUENCE: 14

```
Met Thr Ile Val Trp Phe Thr Leu Leu Thr Leu Ala Val Phe Phe Leu
1               5                   10                  15

Met Glu Gly Val Ala Trp Thr Thr His Arg Tyr Ile Met His Gly Pro
                20                  25                  30

Leu Gly Trp Gly Trp His Arg Asp His Glu Pro His Asp Lys Thr
            35                  40                  45

Phe Glu Val Asn Asp Leu Tyr Gly Val Gly Ala Val Val Gly Thr
    50                  55                  60

Gly Leu Phe Val Val Ala Trp Leu Thr Asp Leu Trp Trp Val Arg Ala
65                  70                  75                  80

Thr Ala Leu Gly Val Thr Leu Tyr Gly Val Tyr Ala Phe Val His
                85                  90                  95

Asp Gly Leu Val His Gln Arg Trp Pro Phe His Trp Met Pro Lys Asn
                100                 105                 110

Gly Tyr Ala Arg Arg Leu Val Gln Ala His Lys Leu His His Ala Val
            115                 120                 125

Gln Thr Arg Asp Gly Ala Val Ser Phe Gly Phe Val Phe Ala Pro Asn
130                 135                 140

Pro Gln Arg Leu Ser Ala Ile Leu Lys Ala Arg Arg Ala Glu Arg Ala
145                 150                 155                 160

Ala Thr Asp Ile Pro Ala Glu
                165
```

<210> SEQ ID NO 15
<211> LENGTH: 531
<212> TYPE: DNA
<213> ORGANISM: Sphingomonas astaxanthinifaciens

<400> SEQUENCE: 15

```
atgtcctggc ctgccggtct cgccctgttc gtatcgacgg tccttctgat ggagggcttc      60
gcctatgtcc tccaccgctt cgtgatgcac tcgcggctcg gctggaactg cacgaaagc     120
catcatcgcg cgcggaccgg ctggttcgag cggaacgacc tctatgccgt ggtcttcgct    180
ttgccctcga tcctgctgat ctggggcggg ctcaatggcg gctggggcga ctgggcgacg    240
tggatggggg ccggggtggc cttctacggg gtgatctatt cggctttca cgacgtcatc     300
gtccacggcc ggctgccgca ccggatcgtg ccgcgttcga cctatttcaa gcggatcgtc    360
caggcgcaca agctgcacca tgcggtcgag agccgcgacg gggcggtgag cttcggcttc    420
ctttacgccc cgccggtcga gcggctgaag caggcgctcc aggccagccg cgaggcgcag    480
ctcaggcgtg cgcggggcgg gtccacagcc cgtcacgagg agcgggccta a             531
```

<210> SEQ ID NO 16
<211> LENGTH: 176
<212> TYPE: PRT
<213> ORGANISM: Sphingomonas astaxanthinifaciens

<400> SEQUENCE: 16

```
Met Ser Trp Pro Ala Gly Leu Ala Leu Phe Val Ser Thr Val Leu Leu
1               5                   10                  15

Met Glu Gly Phe Ala Tyr Val Leu His Arg Phe Val Met His Ser Arg
                20                  25                  30

Leu Gly Trp Asn Trp His Glu Ser His His Arg Ala Arg Thr Gly Trp
            35                  40                  45

Phe Glu Arg Asn Asp Leu Tyr Ala Val Val Phe Ala Leu Pro Ser Ile
    50                  55                  60
```

Leu Leu Ile Trp Gly Gly Leu Asn Gly Gly Trp Asp Trp Ala Thr
65                  70                  75                  80

Trp Met Gly Ala Gly Val Ala Phe Tyr Gly Val Ile Tyr Phe Gly Phe
                85                  90                  95

His Asp Val Ile Val His Gly Arg Leu Pro His Arg Ile Val Pro Arg
            100                 105                 110

Ser Thr Tyr Phe Lys Arg Ile Val Gln Ala His Lys Leu His His Ala
            115                 120                 125

Val Glu Ser Arg Asp Gly Ala Val Ser Phe Gly Phe Leu Tyr Ala Pro
130                 135                 140

Pro Val Glu Arg Leu Lys Gln Ala Leu Gln Ala Ser Arg Glu Ala Gln
145                 150                 155                 160

Leu Arg Arg Ala Arg Gly Gly Ser Thr Ala Arg His Glu Glu Arg Ala
                165                 170                 175

<210> SEQ ID NO 17
<211> LENGTH: 486
<212> TYPE: DNA
<213> ORGANISM: Brevundimonas vesicularis

<400> SEQUENCE: 17
atgtcctggc cgacgatgat cctgctgttt ctcgccacct tcctggggat ggaggtcttc      60
gcctgggcga tgcatcgcta tgtcatgcac ggcctgctgt ggacctggca ccgtagccac     120
catgagccgc acgacgacgt gctggaaaag aacgacctgt tcgccgtggt gttcgccgcc     180
ccggccatca tcctcgtcgc cttgggcctg catctgtggc cttgggcgct gccgatcggc     240
ctgggcgtca cggcctatgg actggtctat ttcttcttcc acgacgggct ggtgcatcgc     300
cggttcccga cgggaatcgc gggccgctca gggttctgga cgcggcgcat tcaggcccac     360
cggctgcatc acgcggtgcg gacgcgtgag ggctgcgtgt cgttcggctt cctgtgggtg     420
cggtcggcgc gcgcgctgaa ggccgaactg tctcagaagc gcggcgcttc agcaacggc      480 gcctaa                                                               486

<210> SEQ ID NO 18
<211> LENGTH: 161
<212> TYPE: PRT
<213> ORGANISM: Brevundimonas vesicularis

<400> SEQUENCE: 18

Met Ser Trp Pro Thr Met Ile Leu Leu Phe Leu Ala Thr Phe Leu Gly
1               5                   10                  15

Met Glu Val Phe Ala Trp Ala Met His Arg Tyr Val Met His Gly Leu
            20                  25                  30

Leu Trp Thr Trp His Arg Ser His Glu Pro His Asp Asp Val Leu
        35                  40                  45

Glu Lys Asn Asp Leu Phe Ala Val Val Phe Ala Ala Pro Ala Ile Ile
    50                  55                  60

Leu Val Ala Leu Gly Leu His Leu Trp Pro Trp Ala Leu Pro Ile Gly
65                  70                  75                  80

Leu Gly Val Thr Ala Tyr Gly Leu Val Tyr Phe Phe Phe His Asp Gly
                85                  90                  95

Leu Val His Arg Arg Phe Pro Thr Gly Ile Ala Gly Arg Ser Gly Phe
            100                 105                 110

Trp Thr Arg Arg Ile Gln Ala His Arg Leu His His Ala Val Arg Thr
            115                 120                 125

-continued

```
Arg Glu Gly Cys Val Ser Phe Gly Phe Leu Trp Val Arg Ser Ala Arg
        130                 135                 140
Ala Leu Lys Ala Glu Leu Ser Gln Lys Arg Gly Ala Ser Ser Asn Gly
145                 150                 155                 160
Ala
```

<210> SEQ ID NO 19
<211> LENGTH: 780
<212> TYPE: DNA
<213> ORGANISM: Brevundimonas vesicularis

<400> SEQUENCE: 19

```
atgggcaag cgaacaggat gcttacgggg ccgcgatgcg ctaagtgtcg cgccatgttc    60
gccgtcacgc caatgtcacg ggtcgtcccg aaccaggccc tgatcggcct gacgctggct   120
ggcctgatcg ccgcggtctg gctgaccctg cacatctacg gcgtctattt tcatcgctgg   180
acgatctgga gcatcctgac cgttccgctg atcgtcgccc tccagacctg gtatccgtc    240
ggcctgttca tcgtcgccca cgacgccatg cacggctcgc tggccccggg acgcccacgg   300
ctgaacacgg cgatcggcag cctggcgctg gccctctacg ccggatttcg gttcgcgcct   360
ttgaagatcg cacaccacgc ccatcacgct gcgcctggta cggcggacga tcccgacttt   420
cacgccgacc cccgcgcgc tttcctgccc tggttctacg gcttttttccg cacctatttc   480
ggctggcgag aactggccgt tctgacggtg ctcgtggccg ttgcggtgct gatcctcggc   540
gcccgcgtgc caatcttct ggccttttgg gccgcgcccg ccctgctatc ggcgctacag   600
cttttcacat tcggaacctg gctgcctcac aggcataccg acgacgcttt ccccgaccac   660
cacaacgccc gcaccagccc cttcggcccg gtcctgtcgt tgctcacctg cttccacttc   720
ggccgccacc acgaacacct cctgacccc tggaagccct ggtggagttt gttcagctag   780
```

<210> SEQ ID NO 20
<211> LENGTH: 259
<212> TYPE: PRT
<213> ORGANISM: Brevundimonas vesicularis

<400> SEQUENCE: 20

```
Met Gly Gln Ala Asn Arg Met Leu Thr Gly Pro Arg Cys Ala Lys Cys
1               5                   10                  15
Arg Ala Met Phe Ala Val Thr Pro Met Ser Arg Val Val Pro Asn Gln
            20                  25                  30
Ala Leu Ile Gly Leu Thr Leu Ala Gly Leu Ile Ala Ala Val Trp Leu
        35                  40                  45
Thr Leu His Ile Tyr Gly Val Tyr Phe His Arg Trp Thr Ile Trp Ser
    50                  55                  60
Ile Leu Thr Val Pro Leu Ile Val Ala Val Gln Thr Trp Leu Ser Val
65                  70                  75                  80
Gly Leu Phe Ile Val Ala His Asp Ala Met His Gly Ser Leu Ala Pro
                85                  90                  95
Gly Arg Pro Arg Leu Asn Thr Ala Ile Gly Ser Leu Ala Leu Ala Leu
            100                 105                 110
Tyr Ala Gly Phe Arg Phe Ala Pro Leu Lys Ile Ala His His Ala His
        115                 120                 125
His Ala Ala Pro Gly Thr Ala Asp Asp Pro Asp Phe His Ala Asp Ala
    130                 135                 140
Pro Arg Ala Phe Leu Pro Trp Phe Tyr Gly Phe Phe Arg Thr Tyr Phe
```

```
                145                 150                 155                 160
Gly Trp Arg Glu Leu Ala Val Leu Thr Val Leu Val Ala Val Ala Val
                    165                 170                 175
Leu Ile Leu Gly Ala Arg Val Pro Asn Leu Leu Ala Phe Trp Ala Ala
                180                 185                 190
Pro Ala Leu Leu Ser Ala Leu Gln Leu Phe Thr Phe Gly Thr Trp Leu
            195                 200                 205
Pro His Arg His Thr Asp Asp Ala Phe Pro Asp His His Asn Ala Arg
        210                 215                 220
Thr Ser Pro Phe Gly Pro Val Leu Ser Leu Leu Thr Cys Phe His Phe
225                 230                 235                 240
Gly Arg His His Glu His Leu Leu Thr Pro Trp Lys Pro Trp Trp Ser
                    245                 250                 255
Leu Phe Ser

<210> SEQ ID NO 21
<211> LENGTH: 780
<212> TYPE: DNA
<213> ORGANISM: Brevundimonas vesicularis

<400> SEQUENCE: 21
atgcggcaag cgaacaggat gcttacgggg ccgcgatgcg ctaagtgtcg cgccatgttc      60
gccgtcacgc caatgtcacg ggtcgtcccg aaccaggccc tgatcggcct gacgctggct     120
ggcctgatcg ccgcggtctg gctgaccctg cacatctacg gcgtctattt tcatcgctgg     180
acgatctgga gcatcctgac cgttccgctg atcgtcgccg tccagacctg ctatccgtc      240 ggcctgttca tcgtcgccca cgacgccatg cacggctcgc tggccccggg acgccacgg      300 ctgaacacgg cgatcggcag cctggcgctg gccctctacg ccggatttcg gttcgcgcct     360
ttgaagatcg cacaccacgc ccatcacgct gcgcctggta cggcggacga tcccgacttt     420
cacgccgacg ccccgcgcgc tttcctgccc tggttctacg gcttttttccg cacctatttc     480 ggctggcgag aactggccgt tctgacggtg ctcgtggccg ttgcggtgct gatcctcggc     540
gcccgcgtgc ccaatcttct ggccttttgg gccgcgcccg ccctgctatc ggcgctacag     600
cttttcacat tcggaacctg gctgcctcac aggcataccg acgacgcttt ccccgaccac     660
cacaacgccc gcaccagccc cttcggcccg gtcctgtcgt tgctcacctg cttccacttc     720
ggccgccacc acgaacacct cctgaccccc tggaagccct ggtggagttt gttcagctag     780

<210> SEQ ID NO 22
<211> LENGTH: 259
<212> TYPE: PRT
<213> ORGANISM: Brevundimonas vesicularis

<400> SEQUENCE: 22

Met Arg Gln Ala Asn Arg Met Leu Thr Gly Pro Arg Cys Ala Lys Cys
1               5                   10                  15
Arg Ala Met Phe Ala Val Thr Pro Met Ser Arg Val Val Pro Asn Gln
            20                  25                  30
Ala Leu Ile Gly Leu Thr Leu Ala Gly Leu Ile Ala Ala Val Trp Leu
        35                  40                  45
Thr Leu His Ile Tyr Gly Val Tyr Phe His Arg Trp Thr Ile Trp Ser
    50                  55                  60
Ile Leu Thr Val Pro Leu Ile Val Ala Val Gln Thr Trp Leu Ser Val
65                  70                  75                  80
```

```
Gly Leu Phe Ile Val Ala His Asp Ala Met His Gly Ser Leu Ala Pro
                85                  90                  95

Gly Arg Pro Arg Leu Asn Thr Ala Ile Gly Ser Leu Ala Leu Ala Leu
            100                 105                 110

Tyr Ala Gly Phe Arg Phe Ala Pro Leu Lys Ile Ala His His Ala His
        115                 120                 125

His Ala Pro Gly Thr Ala Asp Asp Pro Asp Phe His Ala Asp Ala
    130                 135                 140

Pro Arg Ala Phe Leu Pro Trp Phe Tyr Gly Phe Arg Thr Tyr Phe
145                 150                 155                 160

Gly Trp Arg Glu Leu Ala Val Leu Thr Val Leu Val Ala Val Ala Val
                165                 170                 175

Leu Ile Leu Gly Ala Arg Val Pro Asn Leu Leu Ala Phe Trp Ala Ala
            180                 185                 190

Pro Ala Leu Leu Ser Ala Leu Gln Leu Phe Thr Phe Gly Thr Trp Leu
        195                 200                 205

Pro His Arg His Thr Asp Asp Ala Phe Pro Asp His His Asn Ala Arg
    210                 215                 220

Thr Ser Pro Phe Gly Pro Val Leu Ser Leu Leu Thr Cys Phe His Phe
225                 230                 235                 240

Gly Arg His His Glu His Leu Leu Thr Pro Trp Lys Pro Trp Trp Ser
                245                 250                 255

Leu Phe Ser

<210> SEQ ID NO 23
<211> LENGTH: 450
<212> TYPE: DNA
<213> ORGANISM: Corynebacterium glutamicum

<400> SEQUENCE: 23
ttgatcccta tcatcgatat ttcacaaaat gagcaagata gcgatatttt tatggccttt      60
atttatctag gtactctcct agttctcatt gggtgcatgg ctttgtgcga ccaccgttgg     120
aagctagcgt tcttccgcca tccgttacga gcaattcttt cggtaggtgc tgcatatatt     180
ggatttcttt tatgggatat atttggcatt attactggca cttttttatcg cggagactca     240 gcgtttatgt ccggtattaa ccttgcaccc catatgccca ttgaagaact ttttttctta     300
ttcttcctct gctacatcac cctcaacctt acctcggcag cagcattatg gcttaaagca     360
ccactgccta aaaaacccgg taaaaagtct cccctcacac cacagcgcga tactttccaa     420
ccaactacca ctcccgaggt tgaaccatga                                      450

<210> SEQ ID NO 24
<211> LENGTH: 149
<212> TYPE: PRT
<213> ORGANISM: Corynebacterium glutamicum

<400> SEQUENCE: 24

Met Ile Pro Ile Ile Asp Ile Ser Gln Asn Glu Gln Asp Ser Asp Ile
1               5                   10                  15

Phe Met Ala Phe Ile Tyr Leu Gly Thr Leu Leu Val Leu Ile Gly Cys
            20                  25                  30

Met Ala Leu Cys Asp His Arg Trp Lys Leu Ala Phe Phe Arg His Pro
        35                  40                  45

Leu Arg Ala Ile Leu Ser Val Gly Ala Ala Tyr Ile Gly Phe Leu Leu
    50                  55                  60
```

```
Trp Asp Ile Phe Gly Ile Ile Thr Gly Thr Phe Tyr Arg Gly Asp Ser
 65                  70                  75                  80

Ala Phe Met Ser Gly Ile Asn Leu Ala Pro His Met Pro Ile Glu Glu
                 85                  90                  95

Leu Phe Phe Leu Phe Phe Leu Cys Tyr Ile Thr Leu Asn Leu Thr Ser
            100                 105                 110

Ala Ala Ala Leu Trp Leu Lys Ala Pro Leu Pro Lys Lys Pro Gly Lys
        115                 120                 125

Lys Ser Pro Leu Thr Pro Gln Arg Asp Thr Phe Gln Pro Thr Thr Thr
    130                 135                 140

Pro Glu Val Glu Pro
145

<210> SEQ ID NO 25
<211> LENGTH: 393
<212> TYPE: DNA
<213> ORGANISM: Corynebacterium glutamicum

<400> SEQUENCE: 25
atgacttata tttttataag cattccttt ttagcaatag ccatggtcct atttgtctta      60
aagctgcagt ctggaacacc taaactttta ccaatcaccg ctgtcagtgc ccttacccta    120
tgttccctaa ctatcatatt tgataacctc atggtttggg ctgatctctt tggatatggc    180
gatacccagc accttggcat ttggctcggt ttaatccccc tagaggatct tttctatccg    240
ctcttcgcag tacttctgat tcctgcccta tggttgcctg aaatatgtt taaacgcagg     300 aaaaaacgtc cacaccattc cttacccacc atcgccaatg aagcatcac tactagatcc     360 accaccacgc aatctgagcc agaaaagccg tag                                 393

<210> SEQ ID NO 26
<211> LENGTH: 82
<212> TYPE: PRT
<213> ORGANISM: Corynebacterium glutamicum

<400> SEQUENCE: 26

Met Thr Tyr Ile Phe Ile Ser Ile Pro Phe Leu Ala Ile Ala Met Val
  1               5                  10                  15

Leu Phe Val Leu Lys Leu Gln Ser Gly Thr Pro Lys Leu Leu Pro Ile
                 20                  25                  30

Thr Ala Val Ser Ala Leu Thr Leu Cys Ser Leu Thr Ile Ile Phe Asp
             35                  40                  45

Asn Leu Met Val Trp Ala Asp Leu Phe Gly Tyr Gly Asp Thr Gln His
 50                  55                  60

Leu Gly Ile Trp Leu Gly Leu Ile Pro Leu Glu Asp Leu Phe Tyr Pro
 65                  70                  75                  80

Leu Phe

<210> SEQ ID NO 27
<211> LENGTH: 864
<212> TYPE: DNA
<213> ORGANISM: Corynebacterium glutamicum

<400> SEQUENCE: 27
atgatggaaa aaataagact aattctattg tcatctcgcc ccattagctg atcaatacc      60 gcctacccct tggtctggc ctacctatta aatgcaggag agattgactg gctgttttgg    120
ctaggcatcg tattttttct tatcccgtat aacatcgcca tgtatggtat caacgatgtt   180
```

```
tttgattacg aatctgatat gcgtaatccc cgcaaaggcg gcgtcgaggg ggccgtgcta      240
ccgaaaagtt cccacagcac actgttatgg gcctcggcta tctcaacaat tccttcccta      300
gttattcttt tcatatttgg cacctggatg tcgtctttat ggctgacact ctcagtgcta      360
gcagtgattg cttattcagc accgaaattg cgttttaaag aacgcccctt tatcgatgct      420
ctaacatctt ctactcactt cacttcacct gcattaatcg gtgcaacgat cactggaaca      480
tctccttcag cagcgatgtg gatagcactg gatccttttt tcttgtgggg catggccagt      540
cagatccttg gagcagtaca ggatgttaat gcagaccggg aagctaatct gagctcaatt      600
gccactgtaa ttggggcgcg tggagccatt cggctttcag tagtacttta tttactagct      660
gctgtgttag tcactacttt gcctaatccg gcgtggatca tcgggattgc gattctaact      720
tacgtattta atgccgcacg attttggaac attacagatg ccagttgtga acaggctaat      780
cgcagttgga aagttttcct gtggctgaac tactttgttg gtgctgtgat aacgatactg      840
ctaatagcaa ttcatcagat ataa                                             864
```

```
<210> SEQ ID NO 28
<211> LENGTH: 287
<212> TYPE: PRT
<213> ORGANISM: Corynebacterium glutamicum

<400> SEQUENCE: 28

Met Met Glu Lys Ile Arg Leu Ile Leu Leu Ser Ser Arg Pro Ile Ser
1               5                   10                  15

Trp Ile Asn Thr Ala Tyr Pro Phe Gly Leu Ala Tyr Leu Leu Asn Ala
            20                  25                  30

Gly Glu Ile Asp Trp Leu Phe Trp Leu Gly Ile Val Phe Phe Leu Ile
        35                  40                  45

Pro Tyr Asn Ile Ala Met Tyr Gly Ile Asn Asp Val Phe Asp Tyr Glu
    50                  55                  60

Ser Asp Met Arg Asn Pro Arg Lys Gly Gly Val Glu Gly Ala Val Leu
65                  70                  75                  80

Pro Lys Ser Ser His Ser Thr Leu Leu Trp Ala Ser Ala Ile Ser Thr
                85                  90                  95

Ile Pro Phe Leu Val Ile Leu Phe Ile Phe Gly Thr Trp Met Ser Ser
            100                 105                 110

Leu Trp Leu Thr Leu Ser Val Leu Ala Val Ile Ala Tyr Ser Ala Pro
        115                 120                 125

Lys Leu Arg Phe Lys Glu Arg Pro Phe Ile Asp Ala Leu Thr Ser Ser
    130                 135                 140

Thr His Phe Thr Ser Pro Ala Leu Ile Gly Ala Thr Ile Thr Gly Thr
145                 150                 155                 160

Ser Pro Ser Ala Ala Met Trp Ile Ala Leu Gly Ser Phe Phe Leu Trp
                165                 170                 175

Gly Met Ala Ser Gln Ile Leu Gly Ala Val Gln Asp Val Asn Ala Asp
            180                 185                 190

Arg Glu Ala Asn Leu Ser Ser Ile Ala Thr Val Ile Gly Ala Arg Gly
        195                 200                 205

Ala Ile Arg Leu Ser Val Val Leu Tyr Leu Leu Ala Ala Val Leu Val
    210                 215                 220

Thr Thr Leu Pro Asn Pro Ala Trp Ile Ile Gly Ile Ala Ile Leu Thr
225                 230                 235                 240

Tyr Val Phe Asn Ala Ala Arg Phe Trp Asn Ile Thr Asp Ala Ser Cys
                245                 250                 255
```

Glu Gln Ala Asn Arg Ser Trp Lys Val Phe Leu Trp Leu Asn Tyr Phe
              260                 265                 270

Val Gly Ala Val Ile Thr Ile Leu Leu Ile Ala Ile His Gln Ile
          275                 280                 285

<210> SEQ ID NO 29
<211> LENGTH: 200
<212> TYPE: DNA
<213> ORGANISM: Corynebacterium glutamicum

<400> SEQUENCE: 29
tggccgttac cctgcgaatg tccacagggt agctggtagt ttgaaaatca acgccgttgc      60
ccttaggatt cagtaactgg cacattttgt aatgcgctag atctgtgtgc tcagtcttcc     120
aggctgctta tcacagtgaa agcaaaacca attcgtggct gcgaaagtcg tagccaccac     180
gaagtccagg aggacataca                                                 200

<210> SEQ ID NO 30
<211> LENGTH: 1119
<212> TYPE: DNA
<213> ORGANISM: Corynebacterium glutamicum

<400> SEQUENCE: 30
atggacaatg gcatgacaat caccacagaa cattcaactc atcctgatct tgatttcaat      60
gatgagattt atcgggaact aaaccgcatc tgcgcttcgc tatctcaaca gtgcagcaca     120
tatcaaccag agttccgtac ctgcctagat gctgctttcc aagctttgcg aggtggcaag     180
ttaatccgcc ctcgaatgct actggggcta caacacgc ttgtagacga tgacattgag      240
gtcaaactca acaccgtttt acaggtagca gtggctttag aactactgca ttttccctt      300 ttggttcatg acgatgttat tgacggagac ctctatcgcc gaggcaaact taattttatt     360
gggcagattc tcatgcatcg cacacctgaa agttttgcac aaatccagcg cgatccagag     420
catctagatt gggcacaatc taatggactg cttatgggaa atcttttct tgctgccacc     480 catcaaatct tcgcgcgcct tgaccttcca tcatccaac gggttcgact tttagattta      540
ctcaaccaca cgataaatga cactattgtg ggtgagtttc ttgatgtggg attaagcagc     600
aaagccatca gccccaatat ggacattgct ctagaaatga gtcggctaaa acagccaca     660 tacacttttg aacttccaat gagagcagcg gcaattctcg cggaactacc tcaggagatt     720
gaaacaaaga taggtgagat aggcacaaac ttgggcatcg cttatcaatt gcaggacgat     780
tacttatcta cttttggtga cgcagccgaa cacggcaaaa atgccttttc tgaccttcga     840
gaaggaaaag aaactacaat tatcgccttc gctcgagata ctgctaaatg gactgatatt     900
caagacaact tcggctccgc agatctgagc acctctcagg cagagcgaat tcaacatctt     960
ctcatacagt gtggagcaaa gaatcactcc ttgaatgcca tctccgacca cttaaatatc    1020
tgccgttcga tgatcaaaac actaagcccc caggtagatc ccaaggctca aaatttatta    1080
cttaaacaag ttgagcaact agccagccgc aaatcttag                            1119

<210> SEQ ID NO 31
<211> LENGTH: 372
<212> TYPE: PRT
<213> ORGANISM: Corynebacterium glutamicum

<400> SEQUENCE: 31

Met Asp Asn Gly Met Thr Ile Thr Thr Glu His Ser Thr His Pro Asp
1               5                   10                  15

Leu Asp Phe Asn Asp Glu Ile Tyr Arg Glu Leu Asn Arg Ile Cys Ala
                20                  25                  30

Ser Leu Ser Gln Gln Cys Ser Thr Tyr Gln Pro Glu Phe Arg Thr Cys
            35                  40                  45

Leu Asp Ala Ala Phe Gln Ala Leu Arg Gly Gly Lys Leu Ile Arg Pro
        50                  55                  60

Arg Met Leu Leu Gly Leu Tyr Asn Thr Leu Val Asp Asp Ile Glu
65                  70                  75                  80

Val Lys Leu Asn Thr Val Leu Gln Val Ala Val Ala Leu Glu Leu Leu
                85                  90                  95

His Phe Ser Leu Leu Val His Asp Val Ile Asp Gly Asp Leu Tyr
            100                 105                 110

Arg Arg Gly Lys Leu Asn Phe Ile Gly Gln Ile Leu Met His Arg Thr
            115                 120                 125

Pro Glu Ser Phe Ala Gln Ile Gln Arg Asp Pro Glu His Leu Asp Trp
        130                 135                 140

Ala Gln Ser Asn Gly Leu Leu Met Gly Asn Leu Phe Leu Ala Ala Thr
145                 150                 155                 160

His Gln Ile Phe Ala Arg Leu Asp Leu Pro His His Gln Arg Val Arg
                165                 170                 175

Leu Leu Asp Leu Leu Asn His Thr Ile Asn Asp Thr Ile Val Gly Glu
            180                 185                 190

Phe Leu Asp Val Gly Leu Ser Ser Lys Ala Ile Ser Pro Asn Met Asp
        195                 200                 205

Ile Ala Leu Glu Met Ser Arg Leu Lys Thr Ala Thr Tyr Thr Phe Glu
210                 215                 220

Leu Pro Met Arg Ala Ala Ala Ile Leu Ala Glu Leu Pro Gln Glu Ile
225                 230                 235                 240

Glu Thr Lys Ile Gly Glu Ile Gly Thr Asn Leu Gly Ile Ala Tyr Gln
                245                 250                 255

Leu Gln Asp Asp Tyr Leu Ser Thr Phe Gly Asp Ala Ala Glu His Gly
            260                 265                 270

Lys Asp Ala Phe Ser Asp Leu Arg Glu Gly Lys Glu Thr Thr Ile Ile
        275                 280                 285

Ala Phe Ala Arg Asp Thr Ala Lys Trp Thr Asp Ile Gln Asp Asn Phe
290                 295                 300

Gly Ser Ala Asp Leu Ser Thr Ser Gln Ala Glu Arg Ile Gln His Leu
305                 310                 315                 320

Leu Ile Gln Cys Gly Ala Lys Asn His Ser Leu Asn Ala Ile Ser Asp
                325                 330                 335

His Leu Asn Ile Cys Arg Ser Met Ile Lys Thr Leu Ser Pro Gln Val
            340                 345                 350

Asp Pro Lys Ala Gln Asn Leu Leu Leu Lys Gln Val Glu Gln Leu Ala
        355                 360                 365

Ser Arg Lys Ser
        370

<210> SEQ ID NO 32
<211> LENGTH: 915
<212> TYPE: DNA
<213> ORGANISM: Corynebacterium glutamicum

<400> SEQUENCE: 32
atgacacacc aaaattcgcc tctcttcctt aaaagtgcac tgagacttta caatcgggcc    60

```
tcattcaagg cttcacataa agtgatcgaa gaatattcga cgagcttcag tctgtctacg    120
tggttgctat ccccacgcat acgaaatgac atacgaaatc tctatgcagt agttcgtatc    180
gccgatgaga ttgtcgacgg cactgcacat gccgctggtt gctcaactgc aaaatcgaa    240 gagattctcg atgcctatga aattgcggtt cttgcagcac cacaacaacg cttcaacaca    300
gatcttgttt tacaagctta tggtgaaact gcccgacgct gtgatttcga caagagcat     360 gtaatagcct tctttgcatc aatgcgtaag gacctcaaag ctaatacaca cgacccagat    420
agcttcacaa cgtatgtcta tggctccgcg gaagttatag gcctgctttg tctcagcgtt    480
ttcaaccaag gtagaacgat tagcaaaaaa cggctagaga ttatgcaaaa cggagcccgc    540
tcattgggag cggcattcca gaaaattaac tttctccgtg acttggcaga agatcagcaa    600
aatttgggcc gatttatttt ccccaaaacc agccaaggaa ctcttactaa agaacaaaaa    660
gaagatctca tcgctgatat ccgtcaagac ctagcaattg cccacgatgc atttccagaa    720
ataccagtgc aggctcgcat cggagtgatc tctgcttatt tgctctttca aaaactcact    780
gaccgaattg aggctactcc taccgccgat ttattgcggg agcgaatcag agttccactt    840
catatcaaac tctctacact cgctagagcc acgatgaaag gtctatctat gagcatctac    900
agaaagaatt cgtga                                                     915

<210> SEQ ID NO 33
<211> LENGTH: 304
<212> TYPE: PRT
<213> ORGANISM: Corynebacterium glutamicum

<400> SEQUENCE: 33

Met Thr His Gln Asn Ser Pro Leu Phe Leu Lys Ser Ala Leu Arg Leu
1               5                   10                  15

Tyr Asn Arg Ala Ser Phe Lys Ala Ser His Lys Val Ile Glu Glu Tyr
            20                  25                  30

Ser Thr Ser Phe Ser Leu Ser Thr Trp Leu Leu Ser Pro Arg Ile Arg
        35                  40                  45

Asn Asp Ile Arg Asn Leu Tyr Ala Val Val Arg Ile Ala Asp Glu Ile
    50                  55                  60

Val Asp Gly Thr Ala His Ala Ala Gly Cys Ser Thr Ala Lys Ile Glu
65                  70                  75                  80

Glu Ile Leu Asp Ala Tyr Glu Ile Ala Val Leu Ala Ala Pro Gln Gln
                85                  90                  95

Arg Phe Asn Thr Asp Leu Val Leu Gln Ala Tyr Gly Glu Thr Ala Arg
            100                 105                 110

Arg Cys Asp Phe Glu Gln Glu His Val Ile Ala Phe Ala Ser Met
            115                 120                 125

Arg Lys Asp Leu Lys Ala Asn Thr His Asp Pro Asp Ser Phe Thr Thr
    130                 135                 140

Tyr Val Tyr Gly Ser Ala Glu Val Ile Gly Leu Leu Cys Leu Ser Val
145                 150                 155                 160

Phe Asn Gln Gly Arg Thr Ile Ser Lys Lys Arg Leu Glu Ile Met Gln
                165                 170                 175

Asn Gly Ala Arg Ser Leu Gly Ala Ala Phe Gln Lys Ile Asn Phe Leu
            180                 185                 190

Arg Asp Leu Ala Glu Asp Gln Gln Asn Leu Gly Arg Phe Tyr Phe Pro
        195                 200                 205

Lys Thr Ser Gln Gly Thr Leu Thr Lys Glu Gln Lys Glu Asp Leu Ile
```

```
                210                 215                 220
Ala Asp Ile Arg Gln Asp Leu Ala Ile Ala His Asp Ala Phe Pro Glu
225                 230                 235                 240

Ile Pro Val Gln Ala Arg Ile Gly Val Ile Ser Ala Tyr Leu Leu Phe
                245                 250                 255

Gln Lys Leu Thr Asp Arg Ile Glu Ala Thr Pro Thr Ala Asp Leu Leu
            260                 265                 270

Arg Glu Arg Ile Arg Val Pro Leu His Ile Lys Leu Ser Thr Leu Ala
        275                 280                 285

Arg Ala Thr Met Lys Gly Leu Ser Met Ser Ile Tyr Arg Lys Asn Ser
    290                 295                 300

<210> SEQ ID NO 34
<211> LENGTH: 1650
<212> TYPE: DNA
<213> ORGANISM: Corynebacterium glutamicum

<400> SEQUENCE: 34
gtgatgaagg tctcgactaa aactccacgc tcctcaggta ccgccgtagt cataggcgca      60
ggtgttgctg gtttagccac ttctgcactt ttagcacgtg atggctggca agtaactgtt     120
ttggaaaaaa atactgatgt cggtggccga gctggatcgc ttgaaatatc aggctttcct     180
ggctttcgat gggataccgg accttcttgg tacctcatgc ccgaggcctt tgaccatttc     240
ttcgcacttt ttggtgcatg tacttctgat tatctcgatt tggtagaatt aacgcctggt     300
tatcgagttt tttctggcac acatgacgct gtcgatgtcc ccactgggcg tgaagaagca     360
attgcgctat tcgaatccat cgaacccggc gcgggtgcaa aactaggaaa ttatcttgat     420
agcgcggcag acgcctatga cattgccatt gatagattcc tttataataa tttctccacg     480
ttaggcccgc tgcttcaccg ggatgtactg acccgagctg ccgactgtt ttctctactg      540
acccgttctt tacaaaagta cgtaaatagt caattcagta gcccggtgtt gcgccagatc     600
ctaacctatc cagcagtctt cctgtcttcc cgacccacta ctacccatc gatgtaccac      660
ttgatgagtc ataccgattt ggtgcaggga gtgaaatacc ctataggtgg ttttactgca     720
gtggttaacg ctctgcatca gttagcgctg gaaaacgggg ttgagtttca actcgattct     780
gaggtcattt ccatcaacac tgcttcatcg aggggcaaca aagcgccac aggtgtgagc      840
ttgcttcaca acagaaaagt gcaaaatcta gatgcggatc ttgtggtttc agcaggcgac     900
ctacaccata cagaaaataa tctgcttccc cgggaacttc gaacctatcc cgaacgatat     960
tggtccaatc gcaatcctgg aattggagcg gtattaatcc tcctgggcgt aaaaggagag    1020
ttaccccagc tcgaccatca caaccttttc ttcagtgaag attggacaga tgattttgct    1080
gtagtttcg acgggcctca acttacccgc ccccacaatg catcaaattc catttatgtc    1140
tccaagcctt caacgtccga agacggcgtt gcacctgctg gatacgaaaa ccttttttgtt   1200
ttaattccga ccaaggcctc tagcagcatc ggccacggtg atgcgtatat gcagtcggct    1260
tcagcatccg tggaaacaat cgcgtcacat gcaatcaatc aaattgctac gcaagccggc    1320
atccctgacc tcactgaccg aattgtggtc aaacgcacca ttggccctgc ggattttgag    1380
caccgctacc attcatgggt aggcagtgcg ctgggtccag cacatacccct cagacagtcc   1440
gctttcttaa gagggcgcaa tagctcccgc aaggtcaata acctcttcta ttccggtgcc    1500
accaccgtcc cgggtgtagg aatacccatg tgtttaattt ctgccgagaa tattattaag    1560
cgtttacatg ccgataccag tgcaggacca ctgcccgaac cattgccgcc taaaacgaca    1620
```
ccatctcaaa agacctcata cgatcattaa          1650

<210> SEQ ID NO 35
<211> LENGTH: 549
<212> TYPE: PRT
<213> ORGANISM: Corynebacterium glutamicum

<400> SEQUENCE: 35

| | | | | | | | | | | | | | | |
|---|---|---|---|---|---|---|---|---|---|---|---|---|---|---|
| Met | Met | Lys | Val | Ser | Thr | Lys | Thr | Pro | Arg | Ser | Ser | Gly | Thr | Ala | Val |
| 1 | | | | 5 | | | | | 10 | | | | | 15 | |
| Val | Ile | Gly | Ala | Gly | Val | Ala | Gly | Leu | Ala | Thr | Ser | Ala | Leu | Leu | Ala |
| | | | 20 | | | | | 25 | | | | | 30 | | |
| Arg | Asp | Gly | Trp | Gln | Val | Thr | Val | Leu | Glu | Lys | Asn | Thr | Asp | Val | Gly |
| | | 35 | | | | | 40 | | | | | 45 | | | |
| Gly | Arg | Ala | Gly | Ser | Leu | Glu | Ile | Ser | Gly | Phe | Pro | Gly | Phe | Arg | Trp |
| | 50 | | | | | 55 | | | | | 60 | | | | |
| Asp | Thr | Gly | Pro | Ser | Trp | Tyr | Leu | Met | Pro | Glu | Ala | Phe | Asp | His | Phe |
| 65 | | | | | 70 | | | | | 75 | | | | | 80 |
| Phe | Ala | Leu | Phe | Gly | Ala | Cys | Thr | Ser | Asp | Tyr | Leu | Asp | Leu | Val | Glu |
| | | | | 85 | | | | | 90 | | | | | 95 | |
| Leu | Thr | Pro | Gly | Tyr | Arg | Val | Phe | Ser | Gly | Thr | His | Asp | Ala | Val | Asp |
| | | | 100 | | | | | 105 | | | | | 110 | | |
| Val | Pro | Thr | Gly | Arg | Glu | Glu | Ala | Ile | Ala | Leu | Phe | Glu | Ser | Ile | Glu |
| | | | 115 | | | | | 120 | | | | | 125 | | |
| Pro | Gly | Ala | Gly | Ala | Lys | Leu | Gly | Asn | Tyr | Leu | Asp | Ser | Ala | Ala | Asp |
| | 130 | | | | | 135 | | | | | 140 | | | | |
| Ala | Tyr | Asp | Ile | Ala | Ile | Asp | Arg | Phe | Leu | Tyr | Asn | Asn | Phe | Ser | Thr |
| 145 | | | | | 150 | | | | | 155 | | | | | 160 |
| Leu | Gly | Pro | Leu | Leu | His | Arg | Asp | Val | Leu | Thr | Arg | Ala | Gly | Arg | Leu |
| | | | | 165 | | | | | 170 | | | | | 175 | |
| Phe | Ser | Leu | Leu | Thr | Arg | Ser | Leu | Gln | Lys | Tyr | Val | Asn | Ser | Gln | Phe |
| | | | 180 | | | | | 185 | | | | | 190 | | |
| Ser | Ser | Pro | Val | Leu | Arg | Gln | Ile | Leu | Thr | Tyr | Pro | Ala | Val | Phe | Leu |
| | | 195 | | | | | 200 | | | | | 205 | | | |
| Ser | Ser | Arg | Pro | Thr | Thr | Thr | Pro | Ser | Met | Tyr | His | Leu | Met | Ser | His |
| | 210 | | | | | 215 | | | | | 220 | | | | |
| Thr | Asp | Leu | Val | Gln | Gly | Val | Lys | Tyr | Pro | Ile | Gly | Gly | Phe | Thr | Ala |
| 225 | | | | | 230 | | | | | 235 | | | | | 240 |
| Val | Val | Asn | Ala | Leu | His | Gln | Leu | Ala | Leu | Glu | Asn | Gly | Val | Glu | Phe |
| | | | | 245 | | | | | 250 | | | | | 255 | |
| Gln | Leu | Asp | Ser | Glu | Val | Ile | Ser | Ile | Asn | Thr | Ala | Ser | Ser | Arg | Gly |
| | | | 260 | | | | | 265 | | | | | 270 | | |
| Asn | Thr | Ser | Ala | Thr | Gly | Val | Ser | Leu | Leu | His | Asn | Arg | Lys | Val | Gln |
| | | 275 | | | | | 280 | | | | | 285 | | | |
| Asn | Leu | Asp | Ala | Asp | Leu | Val | Val | Ser | Ala | Gly | Asp | Leu | His | His | Thr |
| | 290 | | | | | 295 | | | | | 300 | | | | |
| Glu | Asn | Asn | Leu | Leu | Pro | Arg | Glu | Leu | Arg | Thr | Tyr | Pro | Glu | Arg | Tyr |
| 305 | | | | | 310 | | | | | 315 | | | | | 320 |
| Trp | Ser | Asn | Arg | Asn | Pro | Gly | Ile | Gly | Ala | Val | Leu | Ile | Leu | Leu | Gly |
| | | | | 325 | | | | | 330 | | | | | 335 | |
| Val | Lys | Gly | Glu | Leu | Pro | Gln | Leu | Asp | His | His | Asn | Leu | Phe | Phe | Ser |
| | | | 340 | | | | | 345 | | | | | 350 | | |
| Glu | Asp | Trp | Thr | Asp | Asp | Phe | Ala | Val | Val | Phe | Asp | Gly | Pro | Gln | Leu |
| | | | | 355 | | | | | 360 | | | | | 365 | |

```
Thr Arg Pro His Asn Ala Ser Asn Ser Ile Tyr Val Ser Lys Pro Ser
    370                 375                 380
Thr Ser Glu Asp Gly Val Ala Pro Ala Gly Tyr Glu Asn Leu Phe Val
385                 390                 395                 400
Leu Ile Pro Thr Lys Ala Ser Ser Ile Gly His Gly Asp Ala Tyr
            405                 410                 415
Met Gln Ser Ala Ser Ala Ser Val Glu Thr Ile Ala Ser His Ala Ile
            420                 425                 430
Asn Gln Ile Ala Thr Gln Ala Gly Ile Pro Asp Leu Thr Asp Arg Ile
            435                 440                 445
Val Val Lys Arg Thr Ile Gly Pro Ala Asp Phe Glu His Arg Tyr His
    450                 455                 460
Ser Trp Val Gly Ser Ala Leu Gly Pro Ala His Thr Leu Arg Gln Ser
465                 470                 475                 480
Ala Phe Leu Arg Gly Arg Asn Ser Ser Arg Lys Val Asn Asn Leu Phe
            485                 490                 495
Tyr Ser Gly Ala Thr Thr Val Pro Gly Val Gly Ile Pro Met Cys Leu
            500                 505                 510
Ile Ser Ala Glu Asn Ile Ile Lys Arg Leu His Ala Asp Thr Ser Ala
            515                 520                 525
Gly Pro Leu Pro Glu Pro Leu Pro Pro Lys Thr Thr Pro Ser Gln Lys
    530                 535                 540
Thr Ser Tyr Asp His
545
```

<210> SEQ ID NO 36
<211> LENGTH: 3921
<212> TYPE: DNA
<213> ORGANISM: artificial
<220> FEATURE:
<223> OTHER INFORMATION: Ptuf-crtEBI refers to a nucleic acid sequence
      encoding an artificial operon, consisting of the nucleic acid
      sequences Tuf, crtE, crtB and crtI (see, e.g., SEQ ID NOs: 29, 30,
      32 and 34).

<400> SEQUENCE: 36

```
tggccgttac cctgcgaatg tccacagggt agctggtagt ttgaaaatca acgccgttgc    60
ccttaggatt cagtaactgg cacattttgt aatgcgctag atctgtgtgc tcagtcttcc   120
aggctgctta tcacagtgaa agcaaaacca attcgtggct gcgaaagtcg tagccaccac   180
gaagtccagg aggacataca atggacaatg catgacaat caccacagaa cattcaactc    240
atcctgatct tgatttcaat gatgagattt atcgggaact aaaccgcatc tgcgcttcgc   300
tatctcaaca gtgcagcaca tatcaaccag agttccgtac ctgcctagat gctgctttcc   360
aagctttgcg aggtggcaag ttaatccgcc ctcgaatgct actggggcta tacaacacgc   420
ttgtagacga tgacattgag gtcaaactca caccgttttt acaggtagca gtggctttag   480
aactactgca ttttttccctt ttggttcatg acgatgttat tgacggagac ctctatcgcc   540
gaggcaaact taatttttatt gggcagattc tcatgcatcg cacacctgaa agttttgcac   600
aaatccagcg cgatccagag catctagatt gggcacaatc taatggactg cttatgggaa   660
atctttttct tgctgccacc catcaaatct tcgcgcgcct tgaccttcca catcaccaac   720
gggttcgact tttagattta ctcaaccaca cgataaatga cactattgtg ggtgagtttc   780
ttgatgtggg attaagcagc aaagccatca gccccaatat ggacattgct ctagaaatga   840
gtcggctaaa aacagccaca tacacttttg aacttccaat gagagcagcg gcaattctcg   900
```

```
cggaactacc tcaggagatt gaaacaaaga taggtgagat aggcacaaac ttgggcatcg      960
cttatcaatt gcaggacgat tacttatcta cttttggtga cgcagccgaa cacggcaaag     1020
atgccttttc tgaccttcga gaaggaaaag aaactacaat tatcgccttc gctcgagata     1080
ctgctaaatg gactgatatt caagacaact tcggctccgc agatctgagc acctctcagg     1140
cagagcgaat tcaacatctt ctcatacagt gtggagcaaa gaatcactcc ttgaatgcca     1200
tctccgacca cttaaatatc tgccgttcga tgatcaaaac actaagcccc caggtagatc     1260
ccaaggctca aaatttatta cttaaacaag ttgagcaact agccagccgc aaatcttagc     1320
tgcaggtcga ctctagagga tccgaaagga ggcccttcag atgacacacc aaaattcgcc     1380
tctcttcctt aaaagtgcac tgagacttta caatcgggcc tcattcaagg cttcacataa     1440
agtgatcgaa gaatattcga cgagcttcag tctgtctacg tggttgctat ccccacgcat     1500
acgaaatgac atacgaaatc tctatgcagt agttcgtatc gccgatgaga ttgtcgacgg     1560
cactgcacat gccgctggtt gctcaactgc caaaatcgaa gagattctcg atgcctatga     1620
aattgcggtt cttgcagcac cacaacaacg cttcaacaca gatcttgttt tacaagctta     1680
tggtgaaact gcccgacgct gtgatttcga acaagagcat gtaatagcct tctttgcatc     1740
aatgcgtaag gacctcaaag ctaatacaca cgacccagat agcttcacaa cgtatgtcta     1800
tggctccgcg gaagttatag gcctgctttg tctcagcgtt ttcaaccaag gtagaacgat     1860
tagcaaaaaa cggctagaga ttatgcaaaa cggagcccgc tcattgggag cggcattcca     1920
gaaaattaac tttctccgtg acttggcaga agatcagcaa aatttgggcc gatttttatt     1980
ccccaaaacc agccaaggaa ctcttactaa agaacaaaaa gaagatctca tcgctgatat     2040
ccgtcaagac ctagcaattg cccacgatgc atttccagaa ataccagtgc aggctcgcat     2100
cggagtgatc tctgcttatt tgctctttca aaaactcact gaccgaattg aggctactcc     2160
taccgccgat ttattgcggg agcgaatcag agttccactt catatcaaac tctctacact     2220
cgctagagcc acgatgaaag gtctatctat gagcatctac agaaagaatt cgtgatgaag     2280
gtctcgacta aaactccacg ctcctcaggt accgccgtag tcataggcgc aggtgttgct     2340
ggtttagcca cttctgcact tttagcacgt gatggctggc aagtaactgt tttggaaaaa     2400
aatactgatg tcggtggccg agctggatcg cttgaaatat caggcttttcc tggctttcga     2460
tgggataccg gaccttcttg gtacctcatg cccgaggcct ttgaccatttt cttcgcactt     2520
tttggtgcat gtacttctga ttatctcgat ttggtagaat taacgcctgg ttatcgagtt     2580
ttttctggca cacatgacgc tgtcgatgtc cccactgggc gtgaagaagc aattgcgcta     2640
ttcgaatcca tcgaacccgg cgcgggtgca aaactaggaa attatcttga tagcgcggca     2700
gacgcctatg acattgccat tgatagattc ctttataata atttctccac gttaggcccg     2760
ctgcttcacc gggatgtact gacccgagct ggccgactgt tttctctact gacccgttct     2820
ttacaaaagt acgtaaatag tcaattcagt agcccggtgt tgcgccagat cctaacctat     2880
ccagcagtct tcctgtcttc ccgacccact actaccccat cgatgtacca cttgatgagt     2940
cataccgatt tggtgcaggg agtgaaatac cctataggtg gttttactgc agtggttaac     3000
gctctgcatc agttagcgct ggaaaacggg gttgagtttc aactcgattc tgaggtcatt     3060
tccatcaaca ctgcttcatc gagggcaac acaagcgcca caggtgtgag cttgcttcac     3120
aacagaaaag tgcaaaatct agatgcggat cttgtggttt cagcaggcga cctacaccat     3180
acagaaaata atctgcttcc ccgggaactt cgaacctatc ccgaacgata ttggtccaat     3240
cgcaatcctg gaattggagc ggtattaatc ctcctgggcg taaaaggaga gttaccccag     3300
```

```
ctcgaccatc acaacctttt cttcagtgaa gattggacag atgattttgc tgtagttttc    3360
gacgggcctc aacttacccg cccccacaat gcatcaaatt ccatttatgt ctccaagcct    3420
tcaacgtccg aagacggcgt tgcacctgct ggatacgaaa accttttgt tttaattccg     3480 accaaggcct ctagcagcat cggccacggt gatgcgtata tgcagtcggc ttcagcatcc    3540
gtggaaacaa tcgcgtcaca tgcaatcaat caaattgcta cgcaagccgg catccctgac    3600
ctcactgacc gaattgtggt caaacgcacc attggccctg cggattttga gcaccgctac    3660
cattcatggg taggcagtgc gctgggtcca gcacataccc tcagacagtc cgctttctta    3720
agagggcgca atagctcccg caaggtcaat aacctcttct attccggtgc caccaccgtc    3780
ccgggtgtag gaatacccat gtgtttaatt tctgccgaga atattattaa gcgtttacat    3840
gccgatacca gtgcaggacc actgcccgaa ccattgccgc ctaaaacgac accatctcaa    3900
aagacctcat acgatcatta a                                               3921
```

<210> SEQ ID NO 37
<211> LENGTH: 588
<212> TYPE: DNA
<213> ORGANISM: Corynebacterium glutamicum

<400> SEQUENCE: 37

```
atgctgaata tgcaggaacc agataaaatc catccggcag aacctacact tcgtaatatt      60
tatgacgtta aaactagtga tcccaaaagt gaattagttg atcgttctgg catgtcggaa     120
gaagacattg cgcaaattgg gcggctaatg aaatcgttgg ccagtcttcg cgatgtggaa     180
cgtagtattg gtgaagcctc ggcacgttat atggagctaa gtgcccctga tatgcgagct     240
ttgcactatt tgattgtggc gggcaatgcg ggcgaagtgg tgactccagg aatgcttgga     300
gctcacctta gctttccccc ggcatctgta acaaagacgc ttaataggct agaaaaaggt     360
gggcatattg ttcgtaatgt gcaccccgtc gaccgcaggg ctttcgccct catggtcact     420
gatgccactc gtggagaggc gatgcggacg cttggtaagc atcaggcgcg tcgttttgat     480
gctgctaaac gattaactcc acaagagcgt gaagtggtta tccgattcct tcaggatatg     540
gcacaggagt tatcccttaa taatgcacca tggctcaaca cggagtag                  588
```

<210> SEQ ID NO 38
<211> LENGTH: 195
<212> TYPE: PRT
<213> ORGANISM: Corynebacterium glutamicum

<400> SEQUENCE: 38

```
Met Leu Asn Met Gln Glu Pro Asp Lys Ile His Pro Ala Glu Pro Thr
1               5                   10                  15

Leu Arg Asn Ile Tyr Asp Val Lys Thr Ser Asp Pro Lys Ser Glu Leu
            20                  25                  30

Val Asp Arg Ser Gly Met Ser Glu Glu Asp Ile Ala Gln Ile Gly Arg
        35                  40                  45

Leu Met Lys Ser Leu Ala Ser Leu Arg Asp Val Glu Arg Ser Ile Gly
    50                  55                  60

Glu Ala Ser Ala Arg Tyr Met Glu Leu Ser Ala Pro Asp Met Arg Ala
65                  70                  75                  80

Leu His Tyr Leu Ile Val Ala Gly Asn Ala Gly Glu Val Val Thr Pro
                85                  90                  95

Gly Met Leu Gly Ala His Leu Lys Leu Ser Pro Ala Ser Val Thr Lys
            100                 105                 110
```

```
       Thr Leu Asn Arg Leu Glu Lys Gly Gly His Ile Val Arg Asn Val His
               115                 120                 125

Pro Val Asp Arg Arg Ala Phe Ala Leu Met Val Thr Asp Ala Thr Arg
           130                 135                 140

Gly Glu Ala Met Arg Thr Leu Gly Lys His Gln Ala Arg Arg Phe Asp
       145                 150                 155                 160

Ala Ala Lys Arg Leu Thr Pro Gln Glu Arg Glu Val Val Ile Arg Phe
                       165                 170                 175

Leu Gln Asp Met Ala Gln Glu Leu Ser Leu Asn Asn Ala Pro Trp Leu
                   180                 185                 190

Asn Thr Glu
               195

<210> SEQ ID NO 39
<211> LENGTH: 1149
<212> TYPE: DNA
<213> ORGANISM: Pantoea ananatis

<400> SEQUENCE: 39
atgcaaccgc attatgatct gattctcgtg ggggctggac tcgcgaatgg ccttatcgcc      60
ctgcgtcttc agcagcagca acctgatatg cgtatttttgc ttatcgacgc cgcacccag     120 gcgggcggga tcatacgtg gtcatttcac cacgatgatt tgactgagag ccaacatcgt     180
tggatagctt cgctggtggt tcatcactgg cccgactatc aggtacgctt tcccacacgc    240
cgtcgtaagc tgaacagcgg ctacttctgt attacttctc agcgtttcgc tgaggtttta    300
cagcgacagt ttggcccgca cttgtggatg gataccgcgg tcgcagaggt taatgcggaa    360
tctgttcggt tgaaaaaggg tcaggttatc ggtgcccgcg cggtgattga cgggcgggt     420 tatgcggcaa actcagcact gagcgtgggc ttccaggcgt ttattggcca ggaatggcga    480
ttgagccacc cgcatggttt atcgtctccc attatcatgg atgccacggt cgatcagcaa    540
aatggttatc gcttcgtgta cagcctgccg ctctcgccga ccagattgtt aattgaagac    600
acgcactata tcgataatgc gacattagat cctgaacgcg cgcggcaaaa tatttgcgac    660
tatgccgcgc aacagggttg gcagcttcag acattgctgc gtgaagaaca gggcgcctta    720
cccatcaccc tgtcgggcaa tgccgaggca ttctggcagc agcgccccct ggcctgtagt    780
ggattacgtg ccggtctgtt ccatcctacc accggctatt cactgccgct ggcggttgcc    840
gtggccgacc gcctgagcgc acttgatgtc tttacgtcgg cctcaattca ccaggctatt    900
aggcattttg cccgcgagcg ctggcagcag cagcgctttt tccgcatgct gaatcgcatg    960
ctgtttttag ccggacccgc cgattcacgc tggcgggtta tgcagcgttt ttatggttta   1020
cctgaagatt taattgcccg ttttatgcg ggaaaactca cgctgaccga tcggctacgt    1080
attctgagcg gcaagccgcc tgttccggta ttagcagcat tgcaagccat tatgacgact   1140
catcgttaa                                                            1149

<210> SEQ ID NO 40
<211> LENGTH: 1397
<212> TYPE: DNA
<213> ORGANISM: Pantoea ananatis

<400> SEQUENCE: 40
tggccgttac cctgcgaatg tccacagggt agctggtagt ttgaaaatca acgccgttgc     60
ccttaggatt cagtaactgg cacattttgt aatgcgctag atctgtgtgc tcagtcttcc    120
```

-continued

```
aggctgctta tcacagtgaa agcaaaacca attcgtggct gcgaaagtcg tagccaccac    180
gaagtccagg aggacataca aagcttgcat gcctgcaggt cgactctaga ggaaaggagg    240
cccttcagat gcaaccgcat tatgatctga ttctcgtggg ggctggactc gcgaatggcc    300
ttatcgccct gcgtcttcag cagcagcaac ctgatatgcg tattttgctt atcgacgccg    360
caccccaggc gggcgggaat catacgtggt catttcacca cgatgatttg actgagagcc    420
aacatcgttg gatagcttcg ctggtggttc atcactggcc cgactatcag gtacgctttc    480
ccacacgccg tcgtaagctg aacagcggct acttctgtat tacttctcag cgtttcgctg    540
aggttttaca gcgacagttt ggcccgcact tgtggatgga taccgcggtc gcagaggtta    600
atgcggaatc tgttcggttg aaaaagggtc aggttatcgg tgcccgcgcg gtgattgacg    660 ggcgggtta tgcggcaaac tcagcactga gcgtgggctt ccaggcgttt attggccagg    720
aatggcgatt gagccacccg catggtttat cgtctcccat tatcatggat gccacggtcg    780
atcagcaaaa tggttatcgc ttcgtgtaca gcctgccgct ctcgccgacc agattgttaa    840
ttgaagacac gcactatatc gataatgcga cattagatcc tgaacgcgcg cggcaaaata    900
tttgcgacta tgccgcgcaa cagggttggc agcttcagac attgctgcgt gaagaacagg    960
gcgccttacc catcaccctg tcgggcaatg ccgaggcatt ctggcagcag cgcccctgg   1020 cctgtagtgg attacgtgcc ggtctgttcc atcctaccac cggctattca ctgccgctgg   1080
cggttgccgt ggccgaccgc ctgagcgcac ttgatgtctt tacgtcggcc tcaattcacc   1140
aggctattag gcattttgcc cgcgagcgct ggcagcagca gcgcttttc cgcatgctga   1200 atcgcatgct gttttagcc ggacccgccg attcacgctg gcgggttatg cagcgttttt   1260
atggtttacc tgaagattta attgcccgtt tttatgcggg aaaactcacg ctgaccgatc   1320
ggctacgtat tctgagcggc aagccgcctg ttccggtatt agcagcattg caagccatta   1380
tgacgactca tcgttaa                                                   1397
```

<210> SEQ ID NO 41
<211> LENGTH: 18
<212> TYPE: DNA
<213> ORGANISM: artificial
<220> FEATURE:
<223> OTHER INFORMATION: Oligonucleotides. Sequences used to amplify genes

<400> SEQUENCE: 41

```
gcgcgaagat ttgatggg                                                     18
```

<210> SEQ ID NO 42
<211> LENGTH: 20
<212> TYPE: DNA
<213> ORGANISM: artificial
<220> FEATURE:
<223> OTHER INFORMATION: Oligonucleotides. Sequences used to amplify genes. Sequence in italics = linker sequence for hybridization

<400> SEQUENCE: 42

```
acttgtcacc acagcactac                                                   20
```

<210> SEQ ID NO 43
<211> LENGTH: 20
<212> TYPE: DNA
<213> ORGANISM: artificial
<220> FEATURE:
<223> OTHER INFORMATION: Oligonucleotide sequence used to amplify genes.

<400> SEQUENCE: 43

```
tcgcaccatc tacgacaacc                                              20

<210> SEQ ID NO 44
<211> LENGTH: 20
<212> TYPE: DNA
<213> ORGANISM: artificial
<220> FEATURE:
<223> OTHER INFORMATION: Oligonucleotide sequence used to amplify genes.

<400> SEQUENCE: 44
ctacgaagct gacgccgaag                                              20

<210> SEQ ID NO 45
<211> LENGTH: 42
<212> TYPE: DNA
<213> ORGANISM: artificial
<220> FEATURE:
<223> OTHER INFORMATION: Oligonucleotide sequence used to amplify genes.

<400> SEQUENCE: 45
cccatccact aaacttaaac agattgtcat gccattgtcc at                     42

<210> SEQ ID NO 46
<211> LENGTH: 48
<212> TYPE: DNA
<213> ORGANISM: artificial
<220> FEATURE:
<223> OTHER INFORMATION: Oligonucleotide sequence used to amplify genes.

<400> SEQUENCE: 46
aaaactgcag gaaaggaggc ccttcagatg gacaatggca tgacaatc               48

<210> SEQ ID NO 47
<211> LENGTH: 20
<212> TYPE: DNA
<213> ORGANISM: artificial
<220> FEATURE:
<223> OTHER INFORMATION: Oligonucleotide sequence used to amplify genes.

<400> SEQUENCE: 47
gtggtgctcg agaacataag                                              20

<210> SEQ ID NO 48
<211> LENGTH: 20
<212> TYPE: DNA
<213> ORGANISM: artificial
<220> FEATURE:
<223> OTHER INFORMATION: Oligonucleotide sequence used to amplify genes.

<400> SEQUENCE: 48
cggtcacccg taacaatcag                                              20

<210> SEQ ID NO 49
<211> LENGTH: 20
<212> TYPE: DNA
<213> ORGANISM: artificial
<220> FEATURE:
<223> OTHER INFORMATION: Oligonucleotide sequence used to amplify genes.

<400> SEQUENCE: 49
ttgcacctgc tggatacgaa                                              20

<210> SEQ ID NO 50
<211> LENGTH: 18
<212> TYPE: DNA
```

```
<213> ORGANISM: artificial
<220> FEATURE:
<223> OTHER INFORMATION: Oligonucleotide sequence used to amplify genes.

<400> SEQUENCE: 50
aaaacaatgc gcagcgca                                                 18

<210> SEQ ID NO 51
<211> LENGTH: 20
<212> TYPE: DNA
<213> ORGANISM: artificial
<220> FEATURE:
<223> OTHER INFORMATION: Oligonucleotide sequence used to amplify genes.

<400> SEQUENCE: 51
accggctcca gatttatcag                                               20

<210> SEQ ID NO 52
<211> LENGTH: 18
<212> TYPE: DNA
<213> ORGANISM: artificial
<220> FEATURE:
<223> OTHER INFORMATION: Oligonucleotide sequence used to amplify genes.

<400> SEQUENCE: 52
atcttctctc atccgcca                                                 18

<210> SEQ ID NO 53
<211> LENGTH: 20
<212> TYPE: DNA
<213> ORGANISM: artificial
<220> FEATURE:
<223> OTHER INFORMATION: Oligonucleotide sequence used to amplify genes.

<400> SEQUENCE: 53
aatacgcaaa ccgcctctcc                                               20

<210> SEQ ID NO 54
<211> LENGTH: 20
<212> TYPE: DNA
<213> ORGANISM: artificial
<220> FEATURE:
<223> OTHER INFORMATION: Oligonucleotide sequence used to amplify genes.

<400> SEQUENCE: 54
tactgccgcc aggcaaattc                                               20

<210> SEQ ID NO 55
<211> LENGTH: 42
<212> TYPE: DNA
<213> ORGANISM: artificial
<220> FEATURE:
<223> OTHER INFORMATION: Primer used for sequencing to confirm deletion
      of crtR.

<400> SEQUENCE: 55
gcaggtcgac tctagaggat ccccgcgcga agatttgatg gg                      42

<210> SEQ ID NO 56
<211> LENGTH: 44
<212> TYPE: DNA
<213> ORGANISM: artificial
<220> FEATURE:
<223> OTHER INFORMATION: Primer used for sequencing to confirm deletion
      of crtR.

<400> SEQUENCE: 56
```

```
ccagtgaatt cgagctcggt accccttgtc accacagcac tact        44
```

<210> SEQ ID NO 57
<211> LENGTH: 57
<212> TYPE: DNA
<213> ORGANISM: artificial
<220> FEATURE:
<223> OTHER INFORMATION: Primer used to amplify crtYPa.

<400> SEQUENCE: 57

```
ctgcaggtcg actctagagg aaaggaggcc cttcagatgc aaccgcatta tgatctg    57
```

<210> SEQ ID NO 58
<211> LENGTH: 38
<212> TYPE: DNA
<213> ORGANISM: artificial
<220> FEATURE:
<223> OTHER INFORMATION: Primers used to amplify crtYPa.

<400> SEQUENCE: 58

```
cggtacccgg ggatcttaac gatgagtcgt cataatgg        38
```

<210> SEQ ID NO 59
<211> LENGTH: 945
<212> TYPE: DNA
<213> ORGANISM: Corynebacterium glutamicum

<400> SEQUENCE: 59

```
atgaaagaaa ccgtcggtaa caagattgtc ctcattggcg caggagatgt tggagttgca    60
tacgcatacg cactgatcaa ccagggcatg gcagatcacc ttgcgatcat cgacatcgat   120
gaaaagaaac tcgaaggcaa cgtcatggac ttaaaccatg gtgttgtgtg ggccgattcc   180
cgcacccgcg tcaccaaggg cacctacgct gactgcgaag acgcagccat ggttgtcatt   240
tgtgccggcg cagcccaaaa gccaggcgag acccgcctcc agctggtgga caaaaacgtc   300
aagattatga atccatcgt cggcgatgtc atggacagcg gattcgacgg catcttcctc   360
gtggcgtcca acccagtgga tatcctgacc tacgcagtgt ggaaattctc cggcttggaa   420
tggaaccgcg tgatcggctc cggaactgtc ctggactccg ctcgattccg ctacatgctg   480
ggcgaactct acgaagtggc accaagctcc gtccacgcct acatcatcgg cgaacacggc   540
gacactgaac ttccagtcct gtcctccgcg ccatcgcag gcgtatcgct tagccgaatg   600
ctggacaaag acccagagct tgagggccgt ctagagaaaa ttttcgaaga cacccgcgac   660
gctgcctatc acattatcga cgccaagggc tccacttcct acggcatcgg catgggtctt   720
gctcgcatca cccgcgcaat cctgcagaac aagacgttg cagtcccagt ctctgcactg   780
ctccacggtg aataccggtga ggaagacatc tacatcggca ccccagctgt ggtgaaccgc   840
cgaggcatcc gccgcgttgt cgaactagaa atcaccgacc acgagatgga acgcttcaag   900
cattccgcaa ataccctgcg cgaaattcag aagcagttct tctaa                   945
```

<210> SEQ ID NO 60
<211> LENGTH: 314
<212> TYPE: PRT
<213> ORGANISM: Corynebacterium glutamicum

<400> SEQUENCE: 60

```
Met Lys Glu Thr Val Gly Asn Lys Ile Val Leu Ile Gly Ala Gly Asp
1               5                   10                  15

Val Gly Val Ala Tyr Ala Tyr Ala Leu Ile Asn Gln Gly Met Ala Asp
```

```
            20                  25                  30
His Leu Ala Ile Ile Asp Ile Asp Glu Lys Lys Leu Glu Gly Asn Val
         35                  40                  45

Met Asp Leu Asn His Gly Val Val Trp Ala Asp Ser Arg Thr Arg Val
 50                  55                  60

Thr Lys Gly Thr Tyr Ala Asp Cys Glu Asp Ala Ala Met Val Val Ile
 65                  70                  75                  80

Cys Ala Gly Ala Ala Gln Lys Pro Gly Glu Thr Arg Leu Gln Leu Val
                 85                  90                  95

Asp Lys Asn Val Lys Ile Met Lys Ser Ile Val Gly Asp Val Met Asp
                100                 105                 110

Ser Gly Phe Asp Gly Ile Phe Leu Val Ala Ser Asn Pro Val Asp Ile
            115                 120                 125

Leu Thr Tyr Ala Val Trp Lys Phe Ser Gly Leu Glu Trp Asn Arg Val
        130                 135                 140

Ile Gly Ser Gly Thr Val Leu Asp Ser Ala Arg Phe Arg Tyr Met Leu
145                 150                 155                 160

Gly Glu Leu Tyr Glu Val Ala Pro Ser Ser Val His Ala Tyr Ile Ile
                165                 170                 175

Gly Glu His Gly Asp Thr Glu Leu Pro Val Leu Ser Ser Ala Thr Ile
            180                 185                 190

Ala Gly Val Ser Leu Ser Arg Met Leu Asp Lys Asp Pro Glu Leu Glu
        195                 200                 205

Gly Arg Leu Glu Lys Ile Phe Glu Asp Thr Arg Asp Ala Ala Tyr His
    210                 215                 220

Ile Ile Asp Ala Lys Gly Ser Thr Ser Tyr Gly Ile Gly Met Gly Leu
225                 230                 235                 240

Ala Arg Ile Thr Arg Ala Ile Leu Gln Asn Gln Asp Val Ala Val Pro
                245                 250                 255

Val Ser Ala Leu Leu His Gly Glu Tyr Gly Glu Glu Asp Ile Tyr Ile
            260                 265                 270

Gly Thr Pro Ala Val Val Asn Arg Arg Gly Ile Arg Arg Val Val Glu
        275                 280                 285

Leu Glu Ile Thr Asp His Glu Met Glu Arg Phe Lys His Ser Ala Asn
    290                 295                 300

Thr Leu Arg Glu Ile Gln Lys Gln Phe Phe
305                 310
```

<210> SEQ ID NO 61
<211> LENGTH: 780
<212> TYPE: DNA
<213> ORGANISM: Corynebacterium glutamicum

<400> SEQUENCE: 61

```
atgtacgcag aggagcgccg tcgacagatt gcctcattaa cggcagttga gggacgtgta      60
aatgtcacag aattagcggg ccgattcgat gtcactgcag agacgattcg acgagacctt     120
gcggtgctag accgcgaggg aattgttcac cgcgttcacg gtggcgcagt agccacccaa     180
tctttccaaa ccacagagtt gagctggat actcgtttca ggtctgcatc gtcagcaaag      240
tactccattg ccaaggcagc gatgcagttc ctgcccgctg agcatggcgg actgttcctc     300
gatgcgggaa ctactgttac tgctttggcc gatctcattt ctgagcatcc tagctccaag     360
cagtggtcga tcgtgaccaa ctgcctcccc atcgcactta atctggccaa cgccgggctt     420
gatgatgtcc agctgcttgg aggaagcgtt cgcgcgatca cccaggctgt tgtgggtgac     480
```

```
actgcgcttc gtactctcgc gctgatgcgt gcggatgtag tgttcatcgg caccaacgcg      540
ttgacgttgg atcacggatt gtctacggcc gattcccaag aggctgccat gaaatctgcg      600
atgatcacca acgcccacaa ggtggtggtg ttgtgtgact ccaccaagat gggcaccgac      660
tacctcgtga gctttggcgc aatcagcgat atcgatgtgg tggtcaccga tgcgggtgca      720
ccagcaagtt tcgttgagca gttgcgagaa cgcgatgtag aagttgtgat tgcagaatga      780
```

<210> SEQ ID NO 62
<211> LENGTH: 259
<212> TYPE: PRT
<213> ORGANISM: Corynebacterium glutamicum

<400> SEQUENCE: 62

```
Met Tyr Ala Glu Glu Arg Arg Gln Ile Ala Ser Leu Thr Ala Val
1               5                   10                  15

Glu Gly Arg Val Asn Val Thr Glu Leu Ala Gly Arg Phe Asp Val Thr
                20                  25                  30

Ala Glu Thr Ile Arg Arg Asp Leu Ala Val Leu Asp Arg Glu Gly Ile
                35                  40                  45

Val His Arg Val His Gly Gly Ala Val Ala Thr Gln Ser Phe Gln Thr
        50                  55                  60

Thr Glu Leu Ser Leu Asp Thr Arg Phe Arg Ser Ala Ser Ser Ala Lys
65                  70                  75                  80

Tyr Ser Ile Ala Lys Ala Ala Met Gln Phe Leu Pro Ala Glu His Gly
                85                  90                  95

Gly Leu Phe Leu Asp Ala Gly Thr Thr Val Thr Ala Leu Ala Asp Leu
                100                 105                 110

Ile Ser Glu His Pro Ser Ser Lys Gln Trp Ser Ile Val Thr Asn Cys
            115                 120                 125

Leu Pro Ile Ala Leu Asn Leu Ala Asn Ala Gly Leu Asp Asp Val Gln
    130                 135                 140

Leu Leu Gly Gly Ser Val Arg Ala Ile Thr Gln Ala Val Val Gly Asp
145                 150                 155                 160

Thr Ala Leu Arg Thr Leu Ala Leu Met Arg Ala Asp Val Val Phe Ile
                165                 170                 175

Gly Thr Asn Ala Leu Thr Leu Asp His Gly Leu Ser Thr Ala Asp Ser
                180                 185                 190

Gln Glu Ala Ala Met Lys Ser Ala Met Ile Thr Asn Ala His Lys Val
            195                 200                 205

Val Val Leu Cys Asp Ser Thr Lys Met Gly Thr Asp Tyr Leu Val Ser
    210                 215                 220

Phe Gly Ala Ile Ser Asp Ile Asp Val Val Thr Asp Ala Gly Ala
225                 230                 235                 240

Pro Ala Ser Phe Val Glu Gln Leu Arg Glu Arg Asp Val Glu Val Val
                245                 250                 255

Ile Ala Glu
```

<210> SEQ ID NO 63
<211> LENGTH: 27
<212> TYPE: DNA
<213> ORGANISM: artificial
<220> FEATURE:
<223> OTHER INFORMATION: oligonucleotide primer

<400> SEQUENCE: 63
aaaaggatcc agtcggcttc agcatcc					27

<210> SEQ ID NO 64
<211> LENGTH: 28
<212> TYPE: DNA
<213> ORGANISM: artificial
<220> FEATURE:
<223> OTHER INFORMATION: oligonucleotide primer

<400> SEQUENCE: 64
aaaacccggg atgtgtggga ggcttcgc					28

<210> SEQ ID NO 65
<211> LENGTH: 41
<212> TYPE: DNA
<213> ORGANISM: artificial
<220> FEATURE:
<223> OTHER INFORMATION: oligonucleotide primer

<400> SEQUENCE: 65
gaagtccagg aggacataca atgcaaccgc attatgatct g					41

<210> SEQ ID NO 66
<211> LENGTH: 47
<212> TYPE: DNA
<213> ORGANISM: artificial
<220> FEATURE:
<223> OTHER INFORMATION: oligonucleotide primer

<400> SEQUENCE: 66
tcttactact tgcgctaggt acagttaacg atgagtcgtc ataatgg					47

<210> SEQ ID NO 67
<211> LENGTH: 20
<212> TYPE: DNA
<213> ORGANISM: artificial
<220> FEATURE:
<223> OTHER INFORMATION: oligonucleotide primer

<400> SEQUENCE: 67
tggccgttac cctgcgaatg					20

<210> SEQ ID NO 68
<211> LENGTH: 30
<212> TYPE: DNA
<213> ORGANISM: artificial
<220> FEATURE:
<223> OTHER INFORMATION: oligonucleotide primer

<400> SEQUENCE: 68
ttttgagctc ttaagtccga tccacactgt					30

<210> SEQ ID NO 69
<211> LENGTH: 18
<212> TYPE: DNA
<213> ORGANISM: artificial
<220> FEATURE:
<223> OTHER INFORMATION: oligonucleotide primer

<400> SEQUENCE: 69
gcgcgaagat ttgatggg					18

<210> SEQ ID NO 70
<211> LENGTH: 20
<212> TYPE: DNA
<213> ORGANISM: artificial

```
<220> FEATURE:
<223> OTHER INFORMATION: oligonucleotide primer

<400> SEQUENCE: 70
acttgtcacc acagcactac                                              20

<210> SEQ ID NO 71
<211> LENGTH: 20
<212> TYPE: DNA
<213> ORGANISM: artificial
<220> FEATURE:
<223> OTHER INFORMATION: oligonucleotide primer

<400> SEQUENCE: 71
tcgcaccatc tacgacaacc                                              20

<210> SEQ ID NO 72
<211> LENGTH: 20
<212> TYPE: DNA
<213> ORGANISM: artificial
<220> FEATURE:
<223> OTHER INFORMATION: oligonucleotide primer

<400> SEQUENCE: 72
ctacgaagct gacgccgaag                                              20

<210> SEQ ID NO 73
<211> LENGTH: 42
<212> TYPE: DNA
<213> ORGANISM: artificial
<220> FEATURE:
<223> OTHER INFORMATION: oligonucleotide primer

<400> SEQUENCE: 73
cccatccact aaacttaaac agattgtcat gccattgtcc at                     42

<210> SEQ ID NO 74
<211> LENGTH: 48
<212> TYPE: DNA
<213> ORGANISM: artificial
<220> FEATURE:
<223> OTHER INFORMATION: oligonucleotide primer

<400> SEQUENCE: 74
aaaactgcag gaaaggaggc ccttcagatg gacaatggca tgacaatc               48

<210> SEQ ID NO 75
<211> LENGTH: 20
<212> TYPE: DNA
<213> ORGANISM: artificial
<220> FEATURE:
<223> OTHER INFORMATION: oligonucleotide primer

<400> SEQUENCE: 75
gtggtgctcg agaacataag                                              20

<210> SEQ ID NO 76
<211> LENGTH: 20
<212> TYPE: DNA
<213> ORGANISM: artificial
<220> FEATURE:
<223> OTHER INFORMATION: oligonucleotide primer

<400> SEQUENCE: 76
cggtcacccg taacaatcag                                              20
```

-continued

```
<210> SEQ ID NO 77
<211> LENGTH: 20
<212> TYPE: DNA
<213> ORGANISM: artificial
<220> FEATURE:
<223> OTHER INFORMATION: oligonucleotide primer

<400> SEQUENCE: 77
ttgcacctgc tggatacgaa                                              20

<210> SEQ ID NO 78
<211> LENGTH: 18
<212> TYPE: DNA
<213> ORGANISM: artificial
<220> FEATURE:
<223> OTHER INFORMATION: oligonucleotide primer

<400> SEQUENCE: 78
aaaacaatgc gcagcgca                                                18

<210> SEQ ID NO 79
<211> LENGTH: 20
<212> TYPE: DNA
<213> ORGANISM: artificial
<220> FEATURE:
<223> OTHER INFORMATION: oligonucleotide primer

<400> SEQUENCE: 79
accggctcca gatttatcag                                              20

<210> SEQ ID NO 80
<211> LENGTH: 18
<212> TYPE: DNA
<213> ORGANISM: artificial
<220> FEATURE:
<223> OTHER INFORMATION: oligonucleotide primer

<400> SEQUENCE: 80
atcttctctc atccgcca                                                18

<210> SEQ ID NO 81
<211> LENGTH: 20
<212> TYPE: DNA
<213> ORGANISM: artificial
<220> FEATURE:
<223> OTHER INFORMATION: oligonucleotide primer

<400> SEQUENCE: 81
aatacgcaaa ccgcctctcc                                              20

<210> SEQ ID NO 82
<211> LENGTH: 20
<212> TYPE: DNA
<213> ORGANISM: artificial
<220> FEATURE:
<223> OTHER INFORMATION: oligonucleotide primer

<400> SEQUENCE: 82
tactgccgcc aggcaaattc                                              20

<210> SEQ ID NO 83
<211> LENGTH: 42
<212> TYPE: DNA
<213> ORGANISM: artificial
<220> FEATURE:
<223> OTHER INFORMATION: oligonucleotide primer
```

<210> SEQ ID NO 84
<211> LENGTH: 44
<212> TYPE: DNA
<213> ORGANISM: artificial
<220> FEATURE:
<223> OTHER INFORMATION: oligonucleotide primer

<400> SEQUENCE: 84
ccagtgaatt cgagctcggt accccttgtc accacagcac tact        44

<210> SEQ ID NO 85
<211> LENGTH: 57
<212> TYPE: DNA
<213> ORGANISM: artificial
<220> FEATURE:
<223> OTHER INFORMATION: oligonucleotide primer

<400> SEQUENCE: 85
ctgcaggtcg actctagagg aaaggaggcc cttcagatgc aaccgcatta tgatctg        57

<210> SEQ ID NO 86
<211> LENGTH: 38
<212> TYPE: DNA
<213> ORGANISM: artificial
<220> FEATURE:
<223> OTHER INFORMATION: oligonucleotide primer

<400> SEQUENCE: 86
cggtacccgg ggatcttaac gatgagtcgt cataatgg        38

<210> SEQ ID NO 87
<211> LENGTH: 566
<212> TYPE: PRT
<213> ORGANISM: Escherichia Coli

<400> SEQUENCE: 87

Met Ala Ile Ala Ile Gly Leu Asp Phe Gly Ser Asp Ser Val Arg Ala
1               5                   10                  15

Leu Ala Val Asp Cys Ala Thr Gly Glu Glu Ile Ala Thr Ser Val Glu
                20                  25                  30

Trp Tyr Pro Arg Trp Gln Lys Gly Gln Phe Cys Asp Ala Pro Asn Asn
            35                  40                  45

Gln Phe Arg His His Pro Arg Asp Tyr Ile Glu Ser Met Glu Ala Ala
        50                  55                  60

Leu Lys Thr Val Leu Ala Glu Leu Ser Val Gln Arg Ala Ala Val
65                  70                  75                  80

Val Gly Ile Gly Val Asp Ser Thr Gly Ser Thr Pro Ala Pro Ile Asp
                85                  90                  95

Ala Asp Gly Asn Val Leu Ala Leu Arg Pro Glu Phe Ala Glu Asn Pro
            100                 105                 110

Asn Ala Met Phe Val Leu Trp Lys Asp His Thr Ala Val Glu Glu Ala
        115                 120                 125

Glu Glu Ile Thr Arg Leu Cys His Ala Pro Gly Asn Val Asp Tyr Ser
    130                 135                 140

Arg Tyr Ile Gly Gly Ile Tyr Ser Ser Glu Trp Phe Trp Ala Lys Ile
145                 150                 155                 160

-continued

```
Leu His Val Thr Arg Gln Asp Ser Ala Val Ala Gln Ser Ala Ala Ser
                165                 170                 175

Trp Ile Glu Leu Cys Asp Trp Val Pro Ala Leu Leu Ser Gly Thr Thr
            180                 185                 190

Arg Pro Gln Asp Ile Arg Arg Gly Arg Cys Ser Ala Gly His Lys Ser
        195                 200                 205

Leu Trp His Glu Ser Trp Gly Gly Leu Pro Pro Ala Ser Phe Phe Asp
    210                 215                 220

Glu Leu Asp Pro Ile Leu Asn Arg His Leu Pro Ser Pro Leu Phe Thr
225                 230                 235                 240

Asp Thr Trp Thr Ala Asp Ile Pro Val Gly Thr Leu Cys Pro Glu Trp
                245                 250                 255

Ala Gln Arg Leu Gly Leu Pro Glu Ser Val Val Ile Ser Gly Gly Ala
            260                 265                 270

Phe Asp Cys His Met Gly Ala Val Gly Ala Gly Ala Gln Pro Asn Ala
        275                 280                 285

Leu Val Lys Val Ile Gly Thr Ser Thr Cys Asp Ile Leu Ile Ala Asp
    290                 295                 300

Lys Gln Ser Val Gly Glu Arg Ala Val Lys Gly Ile Cys Gly Gln Val
305                 310                 315                 320

Asp Gly Ser Val Val Pro Gly Phe Ile Gly Leu Glu Ala Gly Gln Ser
                325                 330                 335

Ala Phe Gly Asp Ile Tyr Ala Trp Phe Gly Arg Val Leu Gly Trp Pro
            340                 345                 350

Leu Glu Gln Leu Ala Ala Gln His Pro Glu Leu Lys Thr Gln Ile Asn
        355                 360                 365

Ala Ser Gln Lys Gln Leu Leu Pro Ala Leu Thr Glu Ala Trp Ala Lys
    370                 375                 380

Asn Pro Ser Leu Asp His Leu Pro Val Val Leu Asp Trp Phe Asn Gly
385                 390                 395                 400

Arg Arg Thr Pro Asn Ala Asn Gln Arg Leu Lys Gly Val Ile Thr Asp
                405                 410                 415

Leu Asn Leu Ala Thr Asp Ala Pro Leu Leu Phe Gly Gly Leu Ile Ala
            420                 425                 430

Ala Thr Ala Phe Gly Ala Arg Ala Ile Met Glu Cys Phe Thr Asp Gln
        435                 440                 445

Gly Ile Ala Val Asn Asn Val Met Ala Leu Gly Gly Ile Ala Arg Lys
    450                 455                 460

Asn Gln Val Ile Met Gln Ala Cys Cys Asp Val Leu Asn Arg Pro Leu
465                 470                 475                 480

Gln Ile Val Ala Ser Asp Gln Cys Cys Ala Leu Gly Ala Ala Ile Phe
                485                 490                 495

Ala Ala Val Ala Ala Lys Val His Ala Asp Ile Pro Ser Ala Gln Gln
            500                 505                 510

Lys Met Ala Ser Ala Val Glu Lys Thr Leu Gln Pro Cys Ser Glu Gln
        515                 520                 525

Ala Gln Arg Phe Glu Gln Leu Tyr Arg Arg Tyr Gln Gln Trp Ala Met
    530                 535                 540

Ser Ala Glu Gln His Tyr Leu Pro Thr Ser Ala Pro Ala Gln Ala Ala
545                 550                 555                 560

Gln Ala Val Ala Thr Leu
                565
```

<210> SEQ ID NO 88
<211> LENGTH: 500
<212> TYPE: PRT
<213> ORGANISM: Escherichia coli

<400> SEQUENCE: 88

```
Met Thr Ile Phe Asp Asn Tyr Glu Val Trp Phe Val Ile Gly Ser Gln
1               5                   10                  15

His Leu Tyr Gly Pro Glu Thr Leu Arg Gln Val Thr Gln His Ala Glu
            20                  25                  30

His Val Val Asn Ala Leu Asn Thr Glu Ala Lys Leu Pro Cys Lys Leu
        35                  40                  45

Val Leu Lys Pro Leu Gly Thr Thr Pro Asp Glu Ile Thr Ala Ile Cys
    50                  55                  60

Arg Asp Ala Asn Tyr Asp Asp Arg Cys Ala Gly Leu Val Val Trp Leu
65                  70                  75                  80

His Thr Phe Ser Pro Ala Lys Met Trp Ile Asn Gly Leu Thr Met Leu
                85                  90                  95

Asn Lys Pro Leu Leu Gln Phe His Thr Gln Phe Asn Ala Ala Leu Pro
            100                 105                 110

Trp Asp Ser Ile Asp Met Asp Phe Met Asn Leu Asn Gln Thr Ala His
        115                 120                 125

Gly Gly Arg Glu Phe Gly Phe Ile Gly Ala Arg Met Arg Gln Gln His
    130                 135                 140

Ala Val Val Thr Gly His Trp Gln Asp Lys Gln Ala His Glu Arg Ile
145                 150                 155                 160

Gly Ser Trp Met Arg Gln Ala Val Ser Lys Gln Asp Thr Arg His Leu
                165                 170                 175

Lys Val Cys Arg Phe Gly Asp Asn Met Arg Glu Val Ala Val Thr Asp
            180                 185                 190

Gly Asp Lys Val Ala Ala Gln Ile Lys Phe Gly Phe Ser Val Asn Thr
        195                 200                 205

Trp Ala Val Gly Asp Leu Val Gln Val Val Asn Ser Ile Ser Asp Gly
    210                 215                 220

Asp Val Asn Ala Leu Val Asp Glu Tyr Glu Ser Cys Tyr Thr Met Thr
225                 230                 235                 240

Pro Ala Thr Gln Ile His Gly Lys Lys Arg Gln Asn Val Leu Glu Ala
                245                 250                 255

Ala Arg Ile Glu Leu Gly Met Lys Arg Phe Leu Glu Gln Gly Gly Phe
            260                 265                 270

His Ala Phe Thr Thr Thr Phe Glu Asp Leu His Gly Leu Lys Gln Leu
        275                 280                 285

Pro Gly Leu Ala Val Gln Arg Leu Met Gln Gly Tyr Gly Phe Ala
    290                 295                 300

Gly Glu Gly Asp Trp Lys Thr Ala Ala Leu Leu Arg Ile Met Lys Val
305                 310                 315                 320

Met Ser Thr Gly Leu Gln Gly Gly Thr Ser Phe Met Glu Asp Tyr Thr
                325                 330                 335

Tyr His Phe Glu Lys Gly Asn Asp Leu Val Leu Gly Ser His Met Leu
            340                 345                 350

Glu Val Cys Pro Ser Ile Ala Ala Glu Glu Lys Pro Ile Leu Asp Val
        355                 360                 365

Gln His Leu Gly Ile Gly Gly Lys Asp Asp Pro Ala Arg Leu Ile Phe
    370                 375                 380
```

```
Asn Thr Gln Thr Gly Pro Ala Ile Val Ala Ser Leu Ile Asp Leu Gly
385                 390                 395                 400

Asp Arg Tyr Arg Leu Leu Val Asn Cys Ile Asp Thr Val Lys Thr Pro
            405                 410                 415

His Ser Leu Pro Lys Leu Pro Val Ala Asn Ala Leu Trp Lys Ala Gln
            420                 425                 430

Pro Asp Leu Pro Thr Ala Ser Glu Ala Trp Ile Leu Ala Gly Gly Ala
            435                 440                 445

His His Thr Val Phe Ser His Ala Leu Asn Leu Asn Asp Met Arg Gln
            450                 455                 460

Phe Ala Glu Met His Asp Ile Glu Ile Thr Val Ile Asp Asn Asp Thr
465                 470                 475                 480

Arg Leu Pro Ala Phe Lys Asp Ala Leu Arg Trp Asn Glu Val Tyr Tyr
            485                 490                 495

Gly Phe Arg Arg
            500

<210> SEQ ID NO 89
<211> LENGTH: 231
<212> TYPE: PRT
<213> ORGANISM: Escherichia coli

<400> SEQUENCE: 89

Met Leu Glu Asp Leu Lys Arg Gln Val Leu Glu Ala Asn Leu Ala Leu
1               5                   10                  15

Pro Lys His Asn Leu Val Thr Leu Thr Trp Gly Asn Val Ser Ala Val
            20                  25                  30

Asp Arg Glu Arg Gly Val Phe Val Ile Lys Pro Ser Gly Val Asp Tyr
            35                  40                  45

Ser Val Met Thr Ala Asp Asp Met Val Val Ser Ile Glu Thr Gly
    50                  55                  60

Glu Val Val Glu Gly Thr Lys Lys Pro Ser Ser Asp Thr Pro Thr His
65                  70                  75                  80

Arg Leu Leu Tyr Gln Ala Phe Pro Ser Ile Gly Gly Ile Val His Thr
                85                  90                  95

His Ser Arg His Ala Thr Ile Trp Ala Gln Ala Gly Gln Ser Ile Pro
            100                 105                 110

Ala Thr Gly Thr Thr His Ala Asp Tyr Phe Tyr Gly Thr Ile Pro Cys
            115                 120                 125

Thr Arg Lys Met Thr Asp Ala Glu Ile Asn Gly Glu Tyr Glu Trp Glu
130                 135                 140

Thr Gly Asn Val Ile Val Glu Thr Phe Glu Lys Gln Gly Ile Asp Ala
145                 150                 155                 160

Ala Gln Met Pro Gly Val Leu Val His Ser His Gly Pro Phe Ala Trp
            165                 170                 175

Gly Lys Asn Ala Glu Asp Ala Val His Asn Ala Ile Val Leu Glu Glu
            180                 185                 190

Val Ala Tyr Met Gly Ile Phe Cys Arg Gln Leu Ala Pro Gln Leu Pro
            195                 200                 205

Asp Met Gln Gln Thr Leu Leu Asp Lys His Tyr Leu Arg Lys His Gly
            210                 215                 220

Ala Lys Ala Tyr Tyr Gly Gln
225                 230

<210> SEQ ID NO 90
```

```
<211> LENGTH: 446
<212> TYPE: PRT
<213> ORGANISM: Xanthomonas campestris

<400> SEQUENCE: 90

Met Ser Asn Thr Val Phe Ile Gly Ala Lys Glu Tyr Phe Pro Gly Ile
1               5                   10                  15

Gly Lys Ile Gly Phe Glu Gly Arg Asp Ser Asp Asn Pro Leu Ala Phe
            20                  25                  30

Lys Val Tyr Asp Ala Asn Lys Gln Val Ala Gly Lys Ser Met Ala Glu
        35                  40                  45

His Leu Arg Phe Ala Val Ala Tyr Trp His Ser Phe Cys Gly Asn Gly
    50                  55                  60

Ala Asp Pro Phe Gly Pro Gly Thr Arg Ala Tyr Pro Trp Asp Val Gly
65                  70                  75                  80

Asn Thr Ala Leu Ala Arg Ala Glu Ala Lys Ser Asp Ala Ala Phe Glu
                85                  90                  95

Phe Phe Thr Lys Leu Gly Val Pro Tyr Tyr Cys Phe His Asp Ile Asp
            100                 105                 110

Leu Ala Pro Asp Ala Asp Asp Ile Gly Glu Tyr Glu Asn Asn Leu Lys
        115                 120                 125

His Met Val Arg Ile Ala Lys Gln Arg Gln Ala Asp Thr Gly Val Lys
    130                 135                 140

Leu Leu Trp Gly Thr Ala Asn Leu Phe Ser His Pro Arg Tyr Met Asn
145                 150                 155                 160

Gly Ala Ser Thr Asn Pro Asp Phe Asn Val Val Ala Arg Ala Ala Val
                165                 170                 175

Gln Val Lys Ala Ala Ile Asp Ala Thr Val Glu Leu Gly Gly Glu Asn
            180                 185                 190

Tyr Val Phe Trp Gly Gly Arg Glu Gly Tyr Ala Cys Leu His Asn Thr
        195                 200                 205

Gln Met Lys Arg Glu Gln Asp Asn Met Ala Arg Phe Leu Thr Leu Ala
    210                 215                 220

Arg Asp Tyr Gly Arg Ala Ile Gly Phe Thr Gly Asn Phe Leu Ile Glu
225                 230                 235                 240

Pro Lys Pro Met Glu Pro Met Lys His Gln Tyr Asp Phe Asp Ser Ala
                245                 250                 255

Thr Val Ile Gly Phe Leu His Gln His Gly Leu Asp Gln Asp Phe Lys
            260                 265                 270

Leu Asn Ile Glu Ala Asn His Ala Thr Leu Ser Gly His Ser Phe Glu
        275                 280                 285

His Asp Leu Gln Val Ala Ser Asp Ala Gly Leu Leu Gly Ser Ile Asp
    290                 295                 300

Ala Asn Arg Gly Asn Pro Gln Asn Gly Trp Asp Thr Asp Gln Phe Pro
305                 310                 315                 320

Thr Asp Leu Tyr Asp Thr Val Gly Ala Met Leu Val Val Leu Arg Gln
                325                 330                 335

Gly Gly Leu Ala Pro Gly Gly Leu Asn Phe Asp Ala Lys Val Arg Arg
            340                 345                 350

Glu Ser Ser Asp Pro Gln Asp Leu Phe Leu Ala His Ile Gly Gly Met
        355                 360                 365

Asp Ala Phe Ala Arg Gly Leu Glu Val Ala Asp Ala Leu Leu Thr Ser
    370                 375                 380

Ser Pro Leu Glu Thr Trp Arg Ala Gln Arg Tyr Ala Ser Phe Asp Ser
```

```
                385                 390                 395                 400
Gly Ala Gly Ala Asp Phe Ala Asn Gly Thr Ser Thr Leu Ala Asp Leu
            405                 410                 415
Ala Lys Tyr Ala Ala Gly Arg Gly Glu Pro Thr Gln Val Ser Gly Arg
            420                 425                 430
Gln Glu Ala Tyr Glu Asn Leu Ile Asn Gln Tyr Leu Thr Arg
            435                 440                 445
```

<210> SEQ ID NO 91
<211> LENGTH: 460
<212> TYPE: PRT
<213> ORGANISM: Corynebacterium glutamicum

<400> SEQUENCE: 91

```
Met Ala Leu Val Leu Gly Ile Asp Ser Ser Thr Gln Ser Cys Lys Ala
 1               5                  10                  15
Leu Leu Val Asp Ala Ala Thr Gly Gln Val Ile Asp Glu Gly Arg Ala
            20                  25                  30
Ser His Pro Ser Gly Ser Glu Val Asp Pro Arg Ala Trp Ile Ala Ala
        35                  40                  45
Leu Asp Gln Ala Thr Glu Gly Leu Leu Glu Arg Ala Asp Ala Val Ser
    50                  55                  60
Ile Ala Gly Gln Gln His Gly Met Val Ala Leu Asp Glu Asn Asp Glu
65                  70                  75                  80
Ile Val Arg Pro Ala Leu Leu Trp Asn Asp Thr Arg Ser Ala Gln Ala
                85                  90                  95
Ala Leu Asp Leu Asn Glu Glu Ile Gly Gly Asp Gln Ala Ala Val Asp
            100                 105                 110
Ala Thr Gly Ser Val Tyr Val Ala Ser Leu Thr Ala Thr Lys Met Arg
        115                 120                 125
Trp Met Arg Asp His Glu Pro Glu Asn Ala Ala Arg Thr Ala Ser Val
    130                 135                 140
Met Leu Pro His Asp Phe Leu Thr Trp His Leu Met Gly Arg Gly Arg
145                 150                 155                 160
Lys Val Thr Asp His Gly Asp Ala Ser Gly Thr Gly Tyr Tyr Ser Thr
                165                 170                 175
Arg Asp Arg Ala Trp Arg Thr Asp Leu Ala Ala Leu Ala Leu Gly His
            180                 185                 190
Glu Val Glu Leu Pro Glu Leu Leu Ala Pro Asn Ala Ile Ala Gly Thr
        195                 200                 205
Thr Pro Gly Gly Val Lys Val Ala Gly Thr Gly Asp Asn Ala Ala
    210                 215                 220
Ala Ala Leu Gly Leu Asp Leu Gln Pro Gly Asp Val Ser Val Ser Ile
225                 230                 235                 240
Gly Thr Ser Gly Val Ala Gly Met Thr Val Gln His Ser Val His Asp
                245                 250                 255
Pro Ser Gly Leu Val Thr Gly Phe Ala Asp Ala Thr Gly Ala Tyr Phe
            260                 265                 270
Pro Leu Ala Cys Thr Leu Asn Gly Ala Pro Val Leu Glu Phe Gly Arg
        275                 280                 285
Arg Ile Leu Gly Val Glu Trp Glu Glu Phe Asp Ala Leu Ala Leu Ala
    290                 295                 300
Ala Gln Pro Gly Ser Gly Gly Val Thr Leu Gln Pro Tyr Leu Glu Gly
305                 310                 315                 320
```

-continued

```
Glu Arg Thr Pro Asn Arg Pro Ala Ala Arg Gly Val Leu Ala Gly Leu
                325                 330                 335

Asn Cys Ala Thr Thr Arg Glu Asp Phe Ala Arg Ala Thr Val Glu Gly
            340                 345                 350

Leu Leu Leu Ala Leu Asp Asp Ala Val Thr Ala Leu Val Glu Ala Thr
        355                 360                 365

Gly Val Pro Val Gln Arg Ile Gln Leu Ile Gly Gly Gly Ala Arg Ser
    370                 375                 380

Gln Ala Val Arg Glu Ile Ala Pro Glu Ile Phe Gly His Glu Ile Val
385                 390                 395                 400

Val Pro Glu Pro Ala Glu Tyr Val Ala Leu Gly Ala Ala Arg Gln Ala
                405                 410                 415

Ala Trp Ala Leu Ser Gly Glu Ala Thr Pro Pro Gln Trp Pro Thr Pro
                420                 425                 430

Gly Ser Asp Pro His Arg Ala Pro Lys Asn Thr Glu Leu Ser Thr Arg
            435                 440                 445

Tyr Ala Lys Leu Arg Ala Ala Thr Gln Gly Trp Tyr
450                 455                 460
```